United States Patent
Hung et al.

(10) Patent No.: US 11,332,490 B1
(45) Date of Patent: May 17, 2022

(54) COMPOUNDS AND METHODS FOR TREATING OSTEOARTHRITIS

(71) Applicant: Academia Sinica, Taipei (TW)

(72) Inventors: Shang-Cheng Hung, Taipei (TW); Chi-Huey Wong, Taipei (TW); Ting-Jen Cheng, New Taipei (TW)

(73) Assignee: ACADEMIA SINICA, Taipei (TW)

( * ) Notice: Subject to any disclaimer, the term of this patent is extended or adjusted under 35 U.S.C. 154(b) by 0 days.

(21) Appl. No.: 17/182,156

(22) Filed: Feb. 22, 2021

(51) Int. Cl.
  *C07H 7/02* (2006.01)

(52) U.S. Cl.
  CPC ...................................... *C07H 7/02* (2013.01)

(58) Field of Classification Search
  None
  See application file for complete search history.

(56) References Cited

PUBLICATIONS

Chiu et al., Journal of the American Chemical Society, Feb. 21, 2020, vol. 142, pp. 5285-5292. (Year: 2020).*
Tatai et al., Tetrahedron, vol. 64(42), 2008, pp. 9865-9873. (Year: 2008).*
Chiu et al., "Trisaccharide Sulfate and Its Sulfonamide as an Effective Substrate and Inhibitor of Human Endo-O-sulfatase-1", Feb. 21, 2020, Journal of the American Chemical Society, vol. 142, pp. 5285-5292.

* cited by examiner

*Primary Examiner* — Traviss C McIntosh, III

(57) ABSTRACT

Disclosed herein are substrates and/or inhibitors of endo-O-sulfatase 1 (Sulf-1). According to some embodiments, the substrates and/or inhibitors of Sulf-1 are compounds of formula (I) or (II),

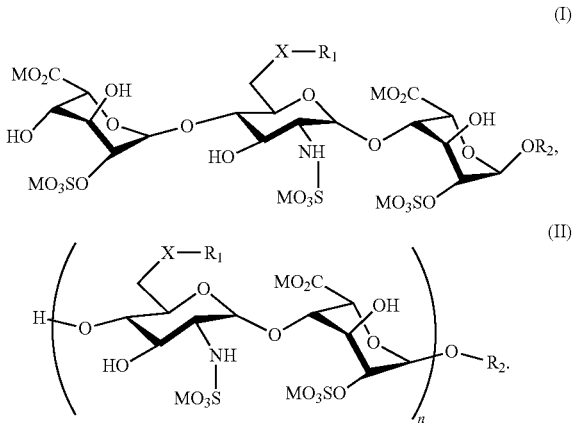

In formula (I) or (II), n is 2 or 3; X is methylene, O, or N; $R_1$ is $-SO_3M$, or $-SO_2NH_2$; $R_2$ is $C_{1-6}$ alkyl or $C_{1-6}$ alkylamine; and M is a monovalent cation selected from the group consisting of lithium, sodium, potassium, and ammonium. Also encompasses herein are methods of identifying and treating a subject having or suspected of having osteoarthritis. The method includes steps of (a) mixing a urine sample of the subject with 4-methylumbelliferyl sulfate (4-MUS) and a Sulf-1 inhibitor of formula (I) or (II); (b) determining a fluorescence intensity of the mixture of the step (a); and (c) treating the subject with an analgesic, a non-steroidal anti-inflammatory drug (NSAID), or a corticosteroid when the determined fluorescence intensity of the step (b) is smaller than that of a control sample, which is a mixture of the urine sample and 4-MUS.

12 Claims, 5 Drawing Sheets

COMPOUNDS AND METHODS FOR TREATING OSTEOARTHRITIS

STATEMENT REGARDING PRIOR DISCLOSURES BY THE INVENTOR OR A JOINT INVENTOR UNDER 37 C.F.R. 1.77(B)(6)

Part of the subject matter of the invention described in the present application was published by the inventors, Chi-Huey Wong, Shang-Cheng Hung, Ting-Jen Cheng in an article titled "Trisaccharide Sulfate and Its Sulfonamide". The article was published on Feb. 21, 2020 in Journal of American Chemistry Society, vol. 142, pages 5285-5292. The publication was made by and/or originated from 3 members of the inventive entity of the present invention, and the entirety of this article is incorporated herein by reference. A copy of the article is provided in a concurrently filed Information Disclosure Statement pursuant to the guidance of 78 Fed. Reg. 11076 (Feb. 14, 2013)."

BACKGROUND OF THE INVENTION

1. Field of the Invention

The present disclosure in general relates to novel endo-O-sulfatase-1 (Sulf-1) substrates and inhibitors, and uses thereof.

2. Description of Related Art

Osteoarthritis (OA) is an aging disease that does not immediately endanger life but would seriously affects the quality of life. With the aging of the population, more and more countries have been classified as elderly societies (such as Japan), thereby increases the cost of maintaining the quality of life.

For the diagnosis of OA, there are no golden rule to define the stage of OA clinically. The diagnosis of OA can only be made by pathological diagnosis (such as pain) and imaging diagnosis (X-ray and MRI). Imaging diagnosis is mainly made in accordance with joint space narrowing (JSN) and osteophytes (Kellgrn-Lawrence Grading Scale). Not only do these evaluation methods not sensitive enough to detect the changes in early OA, but also cannot accurately assess the difference between graders and scorers. For example, for the grade 1 of JSN, the cartilage volume loss is about 11-13%, which cannot be judged by radiography or knee pain assessment. Based on these traditional insensitive detection methods, it often misses the golden time for warning, prevention and treatment of osteoarthritis. To this end, it is necessary to develop new methods for the diagnosis and prediction of OA.

In the clinical, the image diagnosis can only judge the third and fourth stages of OA. Research on biomarkers of OA is very popular. Cartilage matrix is mainly composed of collagens, hyaluronic acid and glycoproteins. Collagen protein is in the form of long strips of fibers, which are interwoven in the cartilage matrix to form a three-dimensional main framework. The area in the middle of the grid is filled with hyaluronic acid and glycoprotein. Chondroitin sulfate (CS) is the main component of glycoprotein. These cartilage matrix-specific proteins, intermediate products produced during synthesis or decomposition, are usually used as the biomarkers of OA.

Currently, there are about 18 biomarkers in the biomarker database of FNIH (Foundation for the National Institutes of Health) and OARSI (Osteoarthritis Research Society International) that have the potential to judge degenerative arthritis. The specimen sources for monitoring these biomarkers are mainly divided into local: synovial fluid, cartilage tissue and whole body: blood, etc., all of which need to be obtained by invasive methods. These biomarkers mainly monitor the synthesis, catabolism of the cartilage matrix or inflammation. Although osteoarthritis is an inflammatory disease, but used as a biomarker of inflammation indicators, they are easily affected by inflammation in other parts of the body. For cartilage matrix metabolism, ADAMTS (a disintegrin and metalloproteins with thrombospondin motifs), MMPs (matrix metalloproteinase) are the main monitoring targets. The cytokines, such as NOS-2 (nitric oxide synthase 2), produced by high oxidative stress and the degrading *intermedia* particles from the cartilage-specific protein, such as Col II (type II collagen) are also the main monitoring objects. These OA biomarkers mainly monitor the cartilage matrix degradation in the middle or late stages of osteoarthritis. For the early stages of osteoarthritis, their effective detection rate is very low.

Sulfatases are enzymes of the esterase class that cleave sulfate esters in biological systems. It regulates the sulfation states that determine the function of many physiological molecules involving developmental cell signaling, pathogenesis, hormone regulation and degradation of extracellular matrix. However, the mechanisms of sulfatases affect the cartilage homeostasis and chondrogenesis remains unclear.

We found that the expression of sulfatase 1 (sulf1) in the OA lesion was higher than that in far lesion parts. The sulf1 was also induced after immunological stimulators. Changes in the ratio of CS-6:CS-4 were found in the urine and cartilage of OA patients. In adulthood, CS-6 is much more than in childhood, but for patients with osteoarthritis, the expression of CS-6 was decreased. Sulfatases 1 (Sulf1) cleaves 6-O-sulfate groups from heparin sulfate, keratin sulfate, and chondroitin sulfate. We hypothesize that sulfatase 1 (Sulf-1), which cleaves the 6-O-sulfate groups to change the structural stability of CS, plays a key role in the degradation of extracellular matrix in osteoarthritis. The unstable extracellular matrix of cartilage will induce matrix degradation and OA processes. Accordingly, sulfatase 1 will be a good candidate for the diagnosis and treatment of OA.

There exist in the related art a need of an improved method for identifying and treating a subject having or suspected of having OA.

SUMMARY OF THE INVENTION

In view of above, the present disclosure provides novel endo-O-sulfatase 1 (Sulf-1) substrates and inhibitors, as well as methods for identifying and treating a subject having OA.

Accordingly, the first aspect of the present disclosure is directed to a compound of formula (I) or a solvate thereof,

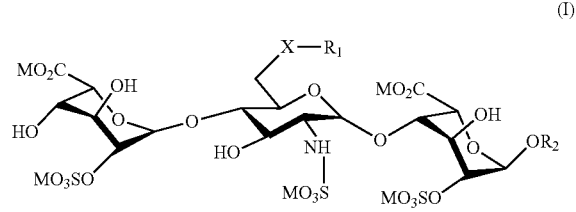

wherein:

X is methylene, O, or N;

$R_1$ is —$SO_3M$, or —$SO_2NH_2$;

$R_2$ is $C_{1-6}$ alkyl or $C_{1-6}$ alkylamine; and

M is H or a monovalent cation selected from the group consisting of lithium, sodium, potassium, and ammonium.

According to some embodiments of the present disclosure, the compound is a human endo-O-sulfatase 1 (Sulf-1) inhibitor selected from the group consisting of

[Structures 46, 46-1, 60, 61, 62, 63, 64, 65, 66, 67, and 68 depicting various sulfated oligosaccharide compounds]

According to further embodiments of the present disclosure, the compound of formula (I) is a substrate of Sulf-1, in which X is O, $R_1$ is —$SO_3M$, $R_2$ is —$(CH_2)_5NH_2$, and M is sodium.

The second aspect of the present disclosure is directed to a compound of formula (II) or a solvate thereof,

[Structure of formula (II)]

wherein:

n is 2 or 3;

X is methylene, O, or N;

$R_1$ is —$SO_3M$, or —$SO_2NH_2$;

$R_2$ is $C_{1-6}$ alkyl or $C_{1-6}$ alkylamine; and

M is a monovalent cation selected from the group consisting of lithium, sodium, potassium, and ammonium.

According to some embodiments of the present disclosure, the compound of formula (II) is a human endo-O- sulfatase 1 (Sulf-1) inhibitor, in which n is 2, X is O, $R_1$ is —$SO_2NH_2$, $R_2$ is —$(CH_2)_5NH_2$, and M is sodium.

According to further embodiments of the present disclosure, the compound of formula (II) is a substrate of Sulf-1, in which n is 2, X is O, $R^1$ is —$SO_3M$, $R_2$ is —$(CH_2)_5NH_2$, and M is sodium.

According to still further embodiments of the present disclosure, the compound of formula (II) is a substrate of Sulf-1, in which n is 3, X is O, $R^1$ is —$SO_3M$, $R_2$ is —$(CH_2)_5NH_2$, and M is sodium.

The third aspect of the present disclosure is directed to a method for identifying and treating a subject having osteoarthritis. The method comprises steps of, (a) mixing a urine sample of the subject with 4-methylumbelliferyl sulfate (4-MUS) and a Sulf-1 inhibitor of formula (I) or (II) described above;

(b) determining a fluorescence intensity of the mixture of the step (a); and (c) treating the subject with an analgesic, a non-steroidal anti-inflammatory drug (NSAID), or a corticosteroid when the determined fluorescence intensity of the step (b) is smaller than that of a control sample, which is a mixture of the urine sample and 4-MUS.

According to some embodiments of the present disclosure, the Sulf-1 inhibitor of formula (I) or (II) is labeled with a tag molecule and coated on a surface of a membrane, and the 4-MUS is coated at one end of the membrane in the form of a line.

Examples of analgesic suitable for use in the present method include, but are not limited to, acetaminophen, codeine and the like.

Examples of NSAID suitable for use in the present method include, but are not limited to, aspirin, ibuprofen, naproxen, diclofenac, celecoxib, piroxicam, indomethacin, meloxicam, ketoprofen, sulindac, diflunisal, nabumetone, oxaprozin, tolmetin, salsalate, etodolac, fenoprofen, flurbiprofen, ketorolac, meclofenamate, and mefenamic acid.

Example of corticosteroid suitable for use in the present method includes, but is not limited to, cortisol.

The details of one or more embodiments of this disclosure are set forth in the accompanying description below. Other features and advantages of the invention will be apparent from the detail descriptions, and from claims.

It is to be understood that both the foregoing general description and the following detailed description are by examples, and are intended to provide further explanation of the invention as claimed.

BRIEF DESCRIPTION OF THE DRAWINGS

The accompanying drawings, which are incorporated in and constitute a part of the specification, illustrate various example systems, methods and other exemplified embodiments of various aspects of the invention. The present description will be better understood from the following detailed description read in light of the accompanying drawings, where.

DETAILED DESCRIPTION OF THE PREFERRED EMBODIMENTS

Figure 1:
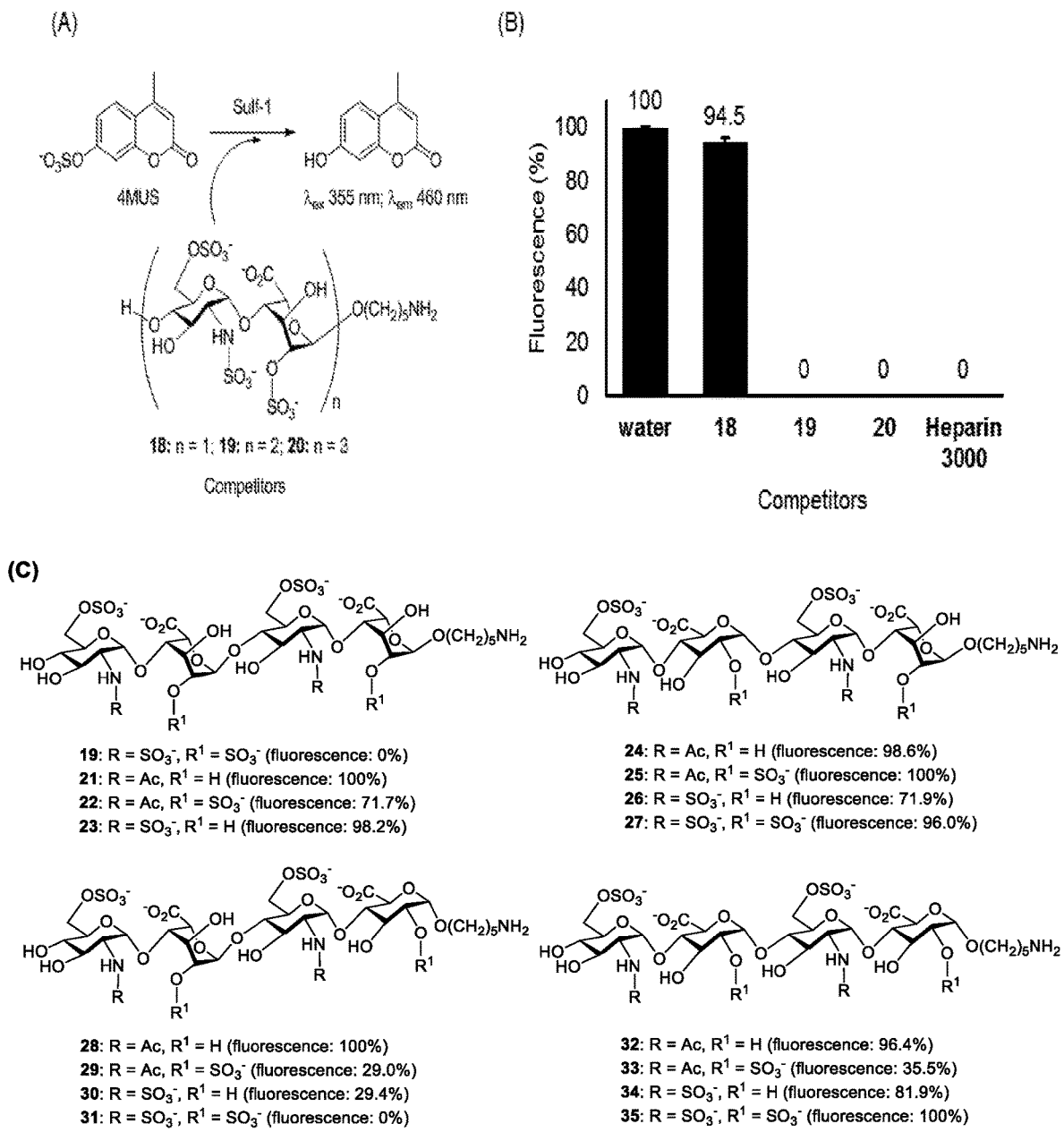
FIG. 1 depicts the screening of Sulf-1 substrate based on competition assay with 4-MUS, in which (A) is fluorogenic assay of 4-MUS and competitors as Sulf-1 substrates, (B) is fluorescence intensities of the disaccharide 18, tetrasaccharide 19, hexasaccharide and heparin 3000 at 320 µM as competitors in the hydrolysis of 4-MUS (4.35 mM) with Sulf-1. The intensity of 4-MUS (4.35 mM) with Sulf-1 in pure water was set as 100%; (C) Fluorogenic screening of various sulfonated tetrasaccharides 21-35 at 0.32 mM as competing substrates for Sulf-1.
Figure 2A:
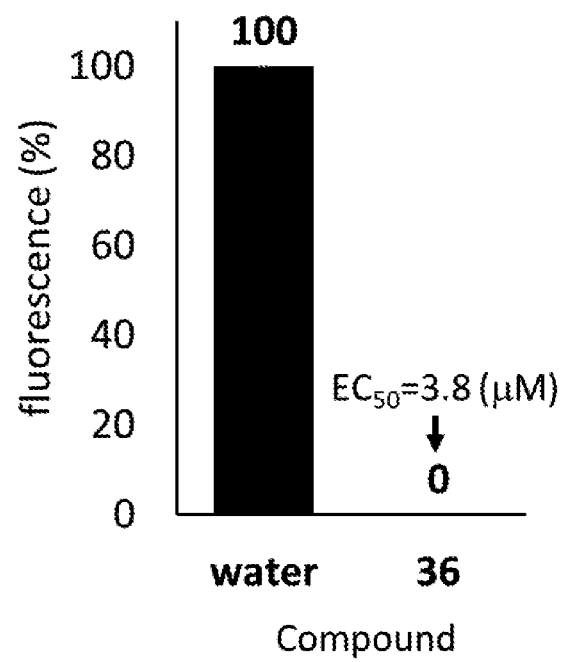
FIG. 2A depicts fluorescence intensities of the trisaccharide 36 at 320 µM as a competing substrate in the hydrolysis of 4-MUS at 4.35 mM with Sulf-1, in which the intensity of 4-MUS (4.35 mM) with Sulf-1 in pure water was set to 100%.
Figure 2B:
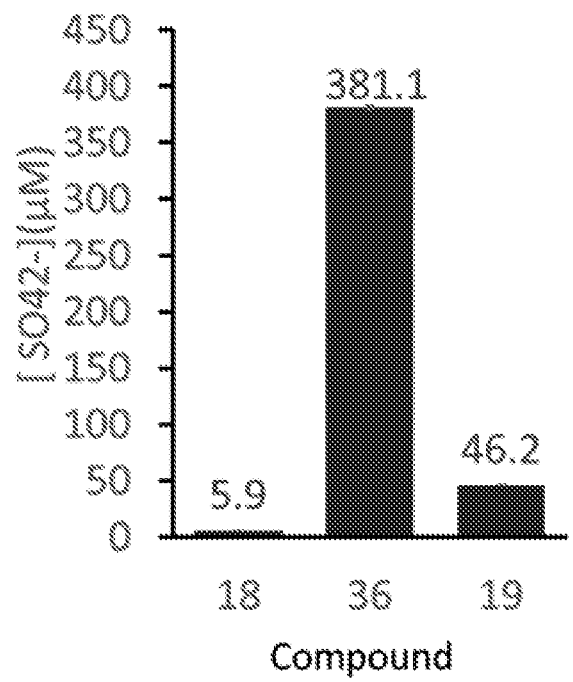
FIG. 2B is the determination of the substrate specificity of 36, 18 or 19 (480 µM) towards Sulf-1 via HPLC measurement of sulfate amount.
Figure 2C:
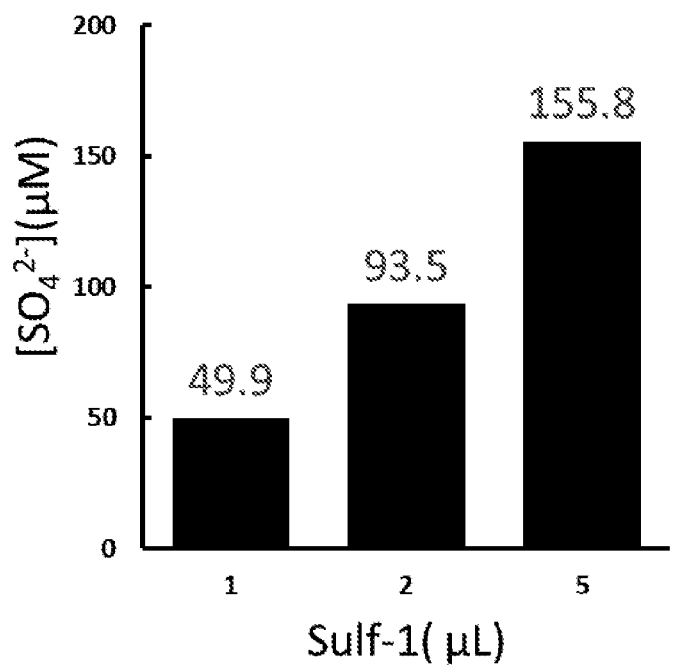
FIG. 2C depicts the concentration-dependent release of $SO_4^{2-}$ of 36 at 480 µM with human Sulf-1.
Figure 2D:
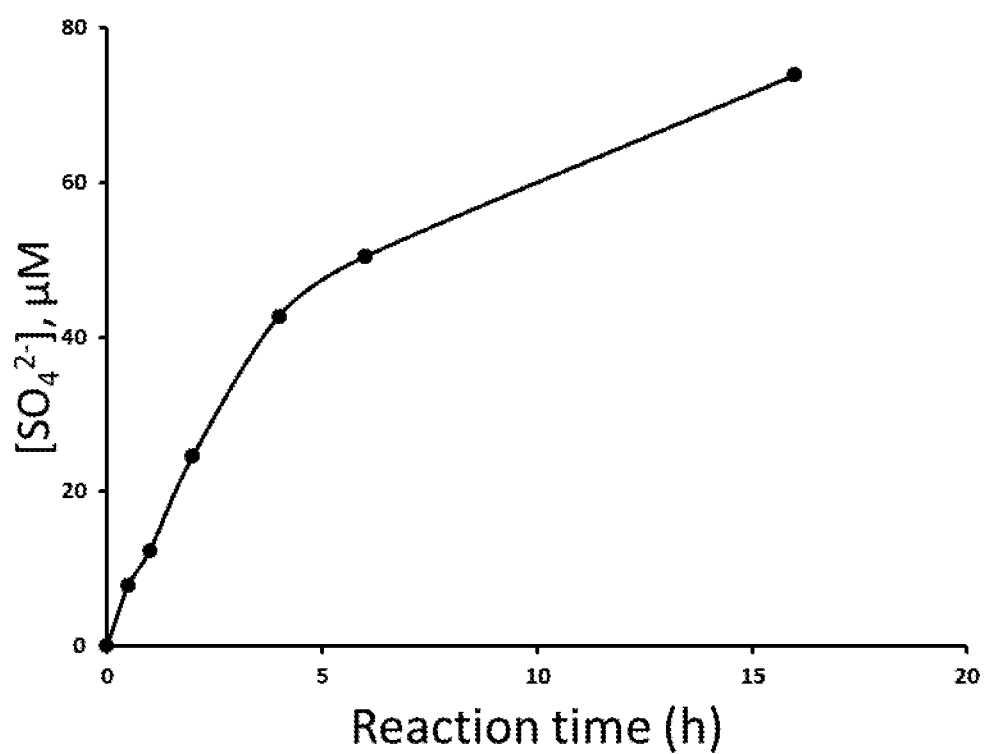
FIG. 2D depicts the time-dependent release of $SO_4^{2-}$ of 36 at 480 µM with human Sulf-1.
Figure 2E:
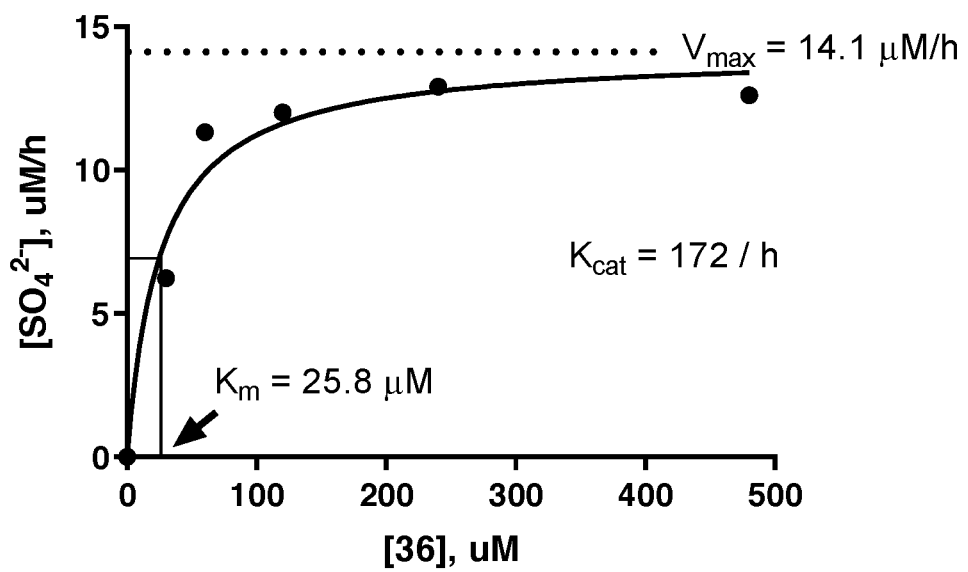
FIG. 2E depicts the determination of kinetic parameters of 36 towards human Sulf-1.

The detailed description provided below in connection with the appended drawings is intended as a description of the present disclosure and is not intended to represent the only forms in which the present disclosure may be constructed or utilized.

1. Definitions

Unless otherwise indicated, the term "patient" or "subject" may be used interchangeably in the present disclosure, and refers to any animal. The animal can be a human subject, or a non-human subject. The subject may be a human, but can also be a mammal in need of veterinary treatment, e.g., domestic animals or game animals, farm animals, and laboratory animals (e.g., rats, mice, guinea pigs, primates, and the like). Usually the animal is a non-human mammal, such as a non-human primate. Non-human primates include chimpanzees, cynomolgous monkeys, spider monkeys, and macaques, e.g., Rhesus or Pan. Domestic animals and game animals include cows, horses, pigs, sheep, deer, bison, buffalo, mink, felines (e.g., domestic cats, canines (e.g., dogs)), wolf and fox, avian species (e.g., chicken, turkey, and ostrich), and fish (e.g., trout, catfish, and salmon). A subject can be one that is not yet being identified by an agent described herein (e.g., a Sulf-1 inhibitor of the present disclosure) as suffering or having a risk of developing osteoarthritis, thus has not yet received treatment therefor.

Unless otherwise indicated, the terms "treat," "treating" and "treatment" contemplate an action that occurs while a patient is suffering from the specified disease or disorder, which reduces the severity of the disease or disorder, or one or more of its symptoms, or retards or slows the progression of the disease or disorder.

Solvates of the compounds of the present invention are also contemplated herein. The term "solvate" must be understood to mean a complex of variable stoichiometry formed by a solute (e.g., the compound of formula (I) or (II)) and a solvent. Examples of suitable solvent include, but are not limited to, water, acetone, methanol, ethanol, and acetic acid. Preferably, the solvent used is a pharmaceutically acceptable solvent. Examples of suitable pharmaceutically acceptable solvents include water, ethanol and acetic acid. Most preferably, the solvent is water. The preparation of salts or solvates can be carried out by means of methods known in the art. It must be noted that non-pharmaceutically acceptable salts or solvates are also within the scope of the invention since they can be useful in the preparation of pharmaceutically acceptable salts, solvates or prodrugs.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The singular forms "a", "and", and "the" are used herein to include plural referents unless the context clearly dictates otherwise.

2. The Compounds of the Present Invention

Aspects of the present disclosure relate to the findings that certain sulfated oligosaccharides are substrates of human endo-O-sulfatases, particularly, Sulf-1; and their sulfonamides are inhibitors of Sulf-1, thus these oligosaccharide sulfonamides may be used for identifying a subject having or suspected of having osteoarthritis, so that suitable treatment or preventive measure may be deployed timely to such subject. Examples of the sulfated oligosaccharides and their sulfonamides are described herein.

In one aspect, the present invention relates to a sulfated trisaccharide of formula (I), or a pharmaceutically acceptable solvate thereof:

(I)

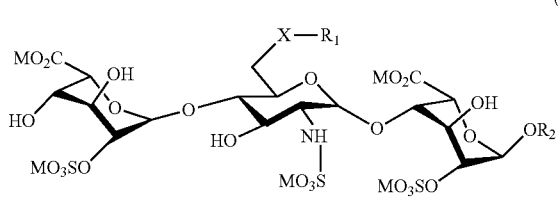

In the formula (I), X is methylene, O, or N; $R_1$ is —$SO_3M$, or —$SO_2NH_2$; $R_2$ is $C_{1-6}$ alkyl or $C_{1-6}$ alkylamine; and M is a monovalent cation selected from the group consisting of lithium, sodium, potassium, and ammonium.

According to preferred embodiments of the present disclosure, the trisaccharide of formula (I) is a Sulf-1 inhibitor selected from the group consisting of

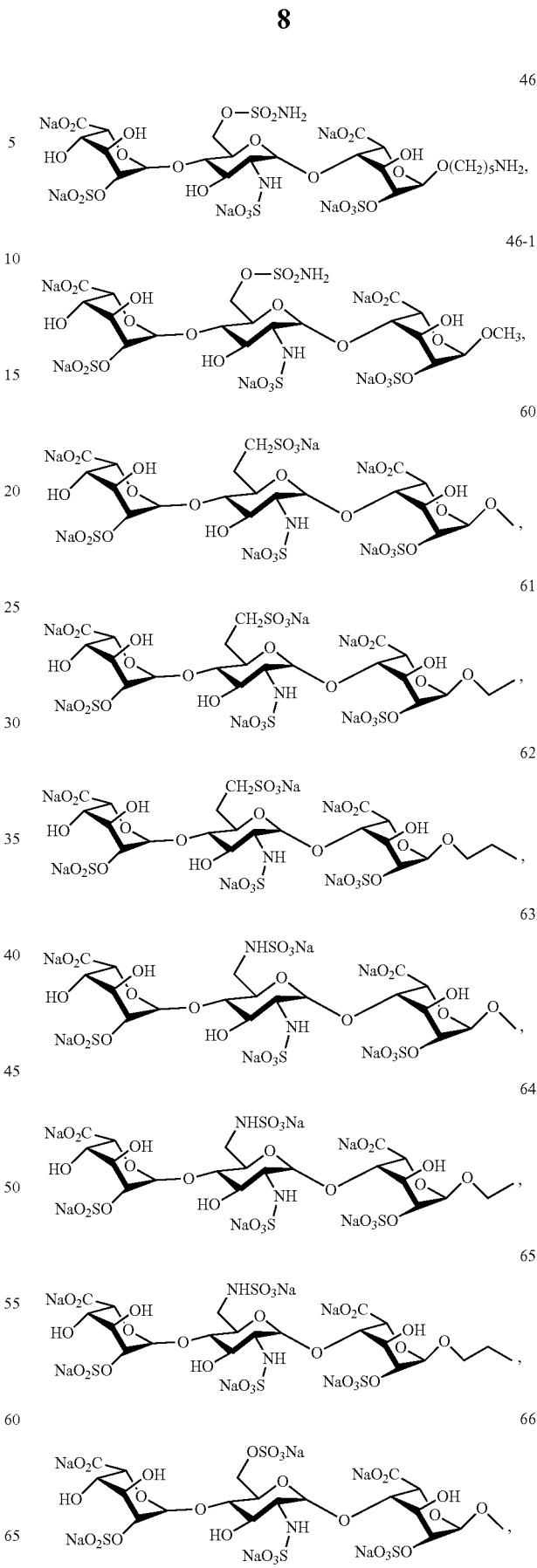

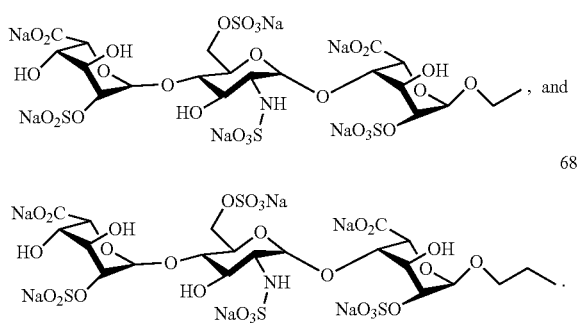

According to some embodiments of the present disclosure, the trisaccharide of formula (I) is a substrate of Sulf-1, in which X is O, $R_1$ is —$SO_3M$, $R_2$ is —$(CH_2)_5NH_2$, and M is sodium.

In another aspect, the present disclosure is directed to an oligosaccharide of formula (II) or as a pharmaceutically acceptable solvate thereof,

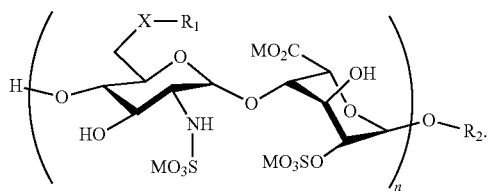

In the formula (II), n is 2 or 3; X is methylene, O, or N; $R_1$ is —$SO_3M$, or —$SO_2NH_2$; $R_2$ is $C_{1-6}$ alkyl or $C_{1-6}$ alkylamine; and M is a monovalent cation selected from the group consisting of lithium, sodium, potassium, and ammonium.

According to preferred embodiments of the present disclosure, the oligosaccharide of formula (II) is a Sulf-1 inhibitor, in which n is 2, X is O, $R_1$ is —$SO_2NH_2$, $R_2$ is —$(CH_2)_5NH_2$, and M is sodium.

According to some embodiments of the present disclosure, the oligosaccharide of formula (II) is a substrate of Sulf-1, in which n is 2, X is O, $R^1$ is —$SO_3M$, $R_2$ is —$(CH_2)_5NH_2$, and M is sodium.

According to further embodiments of the present disclosure, the oligosaccharide of formula (II) is a substrate of Sulf-1, in which n is 3, X is O, $R^1$ is —$SO_3M$, $R_2$ is —$(CH_2)_5NH_2$, and M is sodium.

The sulfated trisaccharides or oligosaccharides and their sulfonamides of the present disclosure (i.e., the compounds of formula (I) or (II)) may be prepared in accordance with procedures described in the working examples. All stereoisomers of the present compounds, such as those which may exist due to asymmetric carbons on the substituents of the compound of formula (I) or (II) including enantiomeric and diastereomeric forms, are contemplated within the scope of this invention. Individual stereoisomers of the compounds of the invention may, for example, be substantially free of other isomers, or may be admixed, for example, as racenates or with all other, or other selected, stereoisomers. The chiral centers of the present invention can have the S or R configuration as defined by the IUPAC 1974 Recommendations.

3. Method of Use

Another aspect of the present disclosure lies in providing methods for identifying and treating subjects having or suspected of having osteoarthritis. To this purpose, embodiments of the present disclosure are directed to the measurement of the level of Sulf-1 in a biological sample derived from an OA subject via measuring a change in fluorescence in a competitor assay, in which the present oligosaccharide sulfonamide(s) competes with a Sulf-1 substrate (i.e., 4-methylumbelliferyl sulfate (4-MUS)), which gives rise to a fluorescent product (i.e., 4-methylumbelliferone, (4-MU)) after being cleaved by Sulf-1. Accordingly, if the present oligosaccharide sulfonamide(s) of formula (I) or (II) did suppress the activity of Sulf-1, then a decrease in fluorescence should be observed, as compared with that of the control.

The present invention thus encompasses a method of identifying and treating subjects having or suspected of having osteoarthritis. The method includes, steps of, (a) mixing a urine sample of the subject with 4-methylumbelliferyl sulfate (4-MUS) and a Sulf-1 inhibitor of formula (I) or (II) of the present disclosure;

(b) determining a fluorescence intensity of the mixture of the step (a); and (c) treating the subject with an analgesic, a non-steroidal anti-inflammatory drug (NSAID), or a corticosteroid when the determined fluorescence intensity of the step (b) is smaller than that of a control sample, which is a mixture of the urine sample and 4-MUS.

Examples of the Sulf-1 inhibitor of formula (I) or (II) suitable for use in the present disclosure include, but are not limited to,

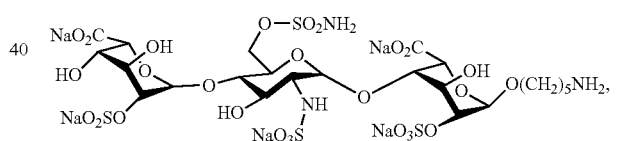

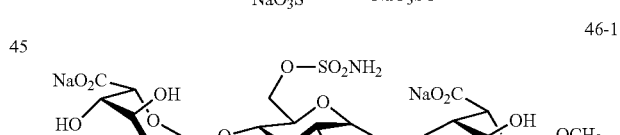

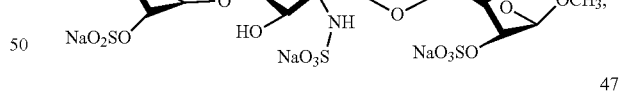

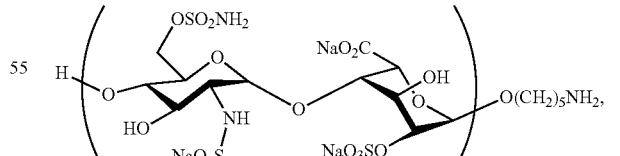

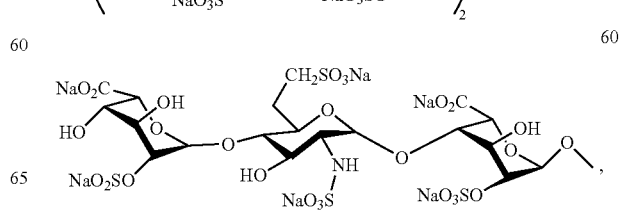

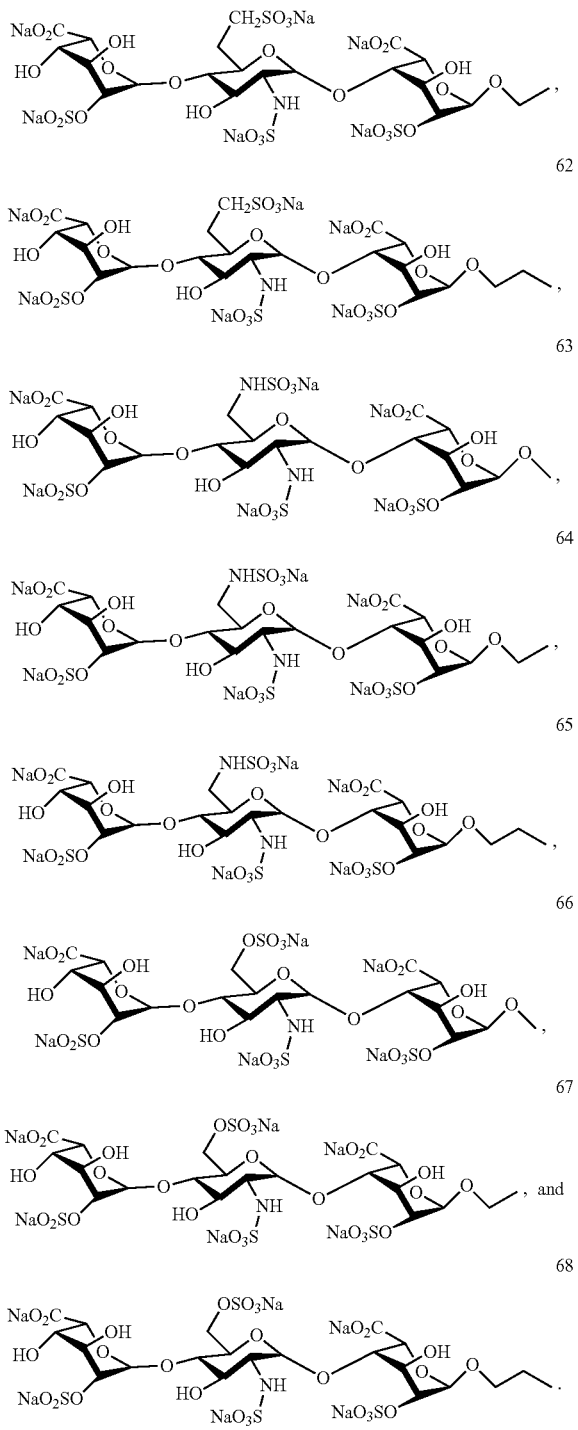

Examples of analgesic suitable for use in the present method include, but are not limited to, acetaminophen, codeine and the like.

Examples of NSAID suitable for use in the present method include, but are not limited to, aspirin, ibuprofen, naproxen, diclofenac, celecoxib, piroxicam, indomethacin, meloxicam, ketoprofen, sulindac, diflunisal, nabumetone, oxaprozin, tolmetin, salsalate, etodolac, fenoprofen, flurbiprofen, ketorolac, meclofenamate, and mefenamic acid.

Example of corticosteroid suitable for use in the present method includes, but is not limited to, cortisol.

The present invention will now be described more specifically with reference to the following embodiments, which are provided for the purpose of demonstration rather than limitation. While they are typically of those that might be used, other procedures, methodologies, or techniques known to those skilled in the art may alternatively be used.

EXAMPLES

Materials and Methods

Competition assay with 4-MUS substrate. A solution containing 320 μM substrate was incubated with Sulf-1 and 4-MUS in 50 mM Tris, 15 mM HEPES, 225 mM NaCl, 5 mM $CaCl_2$, and 5 mM $MgCl_2$ (pH 7.4) for 1 h at 37° C., the fluorescent intensity was measured at 355/460 nm. A control mixture without the competing substrate was defined as 100% fluorescent intensity, and the sample with substrate was determined as percentage of fluorescent intensity: (Fluorescent intensity of substrate sample)/(Fluorescent intensity of control sample).

Sulf-1 activity assay. Human Sulf-1 was overexpressed and purified according to the procedure reported previously.[48] The activity of Sulf-1 was determined by incubating 4-MUS (4.35 mM) with Sulf-1 in 50 mM Tris, 15 mM HEPES, 225 mM NaCl, 5 mM $CaCl_2$, and 5 mM $MgCl_2$ (pH 7.4) for 1 h at 37° C., and the fluorescent intensity was measured at 460 nm following excitation at 355 nm in ELISA reader (CLARIOstar plate reader).

HPLC assay. A solution of the substrate (480 μM) was incubated with or without Sulf1 in 50 mM Tris, 15 mM HEPES, 225 mM NaCl, 5 mM $CaCl_2$, and 5 mM $MgCl_2$ (pH 7.4) for 16 h at 37° C. Release of the sulfate ion from the substrate was quantified via HPLC. Each sample (5 μL) was injected to AS9HC anion-exchange column (Dionex), and the sulfate ion was eluted by 9 mM $Na_2CO_3$ then analyzed by a conductivity detector (PROD, AERS500, 4 mm, Thermal) with reagent-free controller (PROD, RFC-10) and compared with a standard curve with $Na_2SO_4$ (Merck) from 0 to 500 μM.

Sulf-1 inhibition assay. The inhibition activity was measured by the released 4-MU from 4-MUS in the presence of human Sulf-1 and the inhibitor. Sulf-1 was incubated with the inhibitor (0-10 μM) and 4-MUS (0-20 mM) in 50 mM Tris, 15 mM HEPES, 225 mM NaCl, 5 mM $CaCl_2$, and 5 mM $MgCl_2$ (pH 7.4) for 1 h at 37° C. The initial rates of 4-MUS hydrolysis were determined by measuring the fluorescent intensity at 460 nm following excitation at 355 nm (CLARIOstar, BMG LABTECH). The data obtained were fitted to the Michaelis-Menten equation using the GraphPad to determine the enzyme inhibition parameters.

Determination of dissociation constant ($K_D$) using surface plasmon resonance. Compound 46 was immobilized on the surface of a Biacore sensor chip (GE Healthcare) according to the manufacturer's guidelines using Biacore T200 system. The kinetic analysis study was performed at different concentrations of hSulf1$_{d417-726}$ protein upon serial dilution to 250, 125, 63, 31 and 15 nM in running buffer [20 mM NaOAc (pH 5.0), 150 mM NaCl, and 0.05% Tween 20] and injected on to the chip surface with a flow rate of 25 μL/min at 25° C. In each run, the chip sensor surface was regenerated by injecting 4 M NaCl. The titration curves fit well to a 1:1 Langmuir binding model for calculations of equilibrium constants.

Example 1 Chemical Synthesis of the HS Oligosaccharides and Screening of Sulf-1 Substrates

1.1 Synthesis of the Di- and Tetrasaccharide Donors 4 and 7

The synthesis of the glycosyl donors 4 and 7 was commenced from a common disaccharide 3 (Scheme 1), which was generated by -stereoselective glycosylation from the individual monosaccharides 1 and 2 according to a previous report (Zulueta M. M. L. et al., *J Am Chem Soc* 2012, 134, 8988-8995). Cu(OTf)$_2$-catalyzed acetolysis of compound 3 followed by addition of trimethylsilyl p-toluenyl thioether (TMSSTol) in the presence of ZnI$_2$ yielded the thioglycoside donor 4 (77% in two steps). Cleavage of the 2-naphthylmethyl (2-NAP) group at the 4'-O position of 3 with 2,3-dichloro-5,6-dicyano-1,4-benzoquinone (DDQ) furnished the 4'-alcohol 5 (75%). Coupling with compound 4 upon N-iodosuccinimide/trifluoromethanesulfonic acid (NIS/TfOH) activation provided the expected tetrasaccharide 6 (80%). The -glycosidic bond was formed by neighboring group (2-O-Bz) participation. Compound 6 was then subjected to acetolysis and thioglycoside formation, affording the desired donor 7 (78%) in two steps.

Scheme 1. Preparation of the Di- and Tetrasaccharide Donors 4 and 7

Reagents and conditions: (a) (1) 1.5 mol % Cu(OTf)$_2$, Ac$_2$O, 0 C, 2 h; (2) TMSSTol, ZnI$_2$, CH$_2$Cl$_2$, 2 h; 4: 77% (2 steps), 7: 78% (2 steps); (b) DDQ, CH$_2$Cl$_2$/H$_2$O (18/1, v/v), rt, 4 h; 75%; (c) 4, NIS, TfOH, 3 Å molecular sieves, CH$_2$Cl$_2$, 60 C to-40 C, 4 h; 80%. Ac, acetyl; Bn, benzyl; Bz, benzoyl; 2-NAP, 2-naphthylmethyl; PBB, p-bromobenzyl; TBDPS, tert-butyldiphenylsilyl; Tf, trifluoromethylsulfonyl; TMS, trimethylsilyl; Tol, 4-methylphenyl.

1.2 Synthesis of HS Oligosaccharides 18, 19, and 20.

With the orthogonally protected thioglycoside donors 4 and 7 in hand, HS oligosaccharides with various chain lengths were prepared in accordance with procedures described in Scheme 2. The synthesis of the linker-attached disaccharide 8 began by coupling compound 4 with 5-(N-benzyl-N-benzyloxycarbonyl)amino-1-pentanol [HO(CH$_2$)$_5$N(Bn)Cbz] under a combination of NIS and TfOH. The corresponding α-form product 8 was obtained in 77% yield. Treatment of compound 8 with DDQ afforded the disaccharide acceptor 9 (75%), which was subsequently coupled with the donors 4 and 7 in exclusive -stereoselectivity to form the tetrasaccharide 10 (81%) and hexasaccharide 11 (82%), respectively. Removal of all Ac and Bz groups in compounds 8, 10, and 11 using sodium methoxide followed by oxidation with (2,2,6,6-tetramethylpiperidin-1-yl)oxyl (TEMPO) gave the lactones 12 (67%), 13 (70%), and 14 (80%), respectively. The cyclic ester was confirmed through

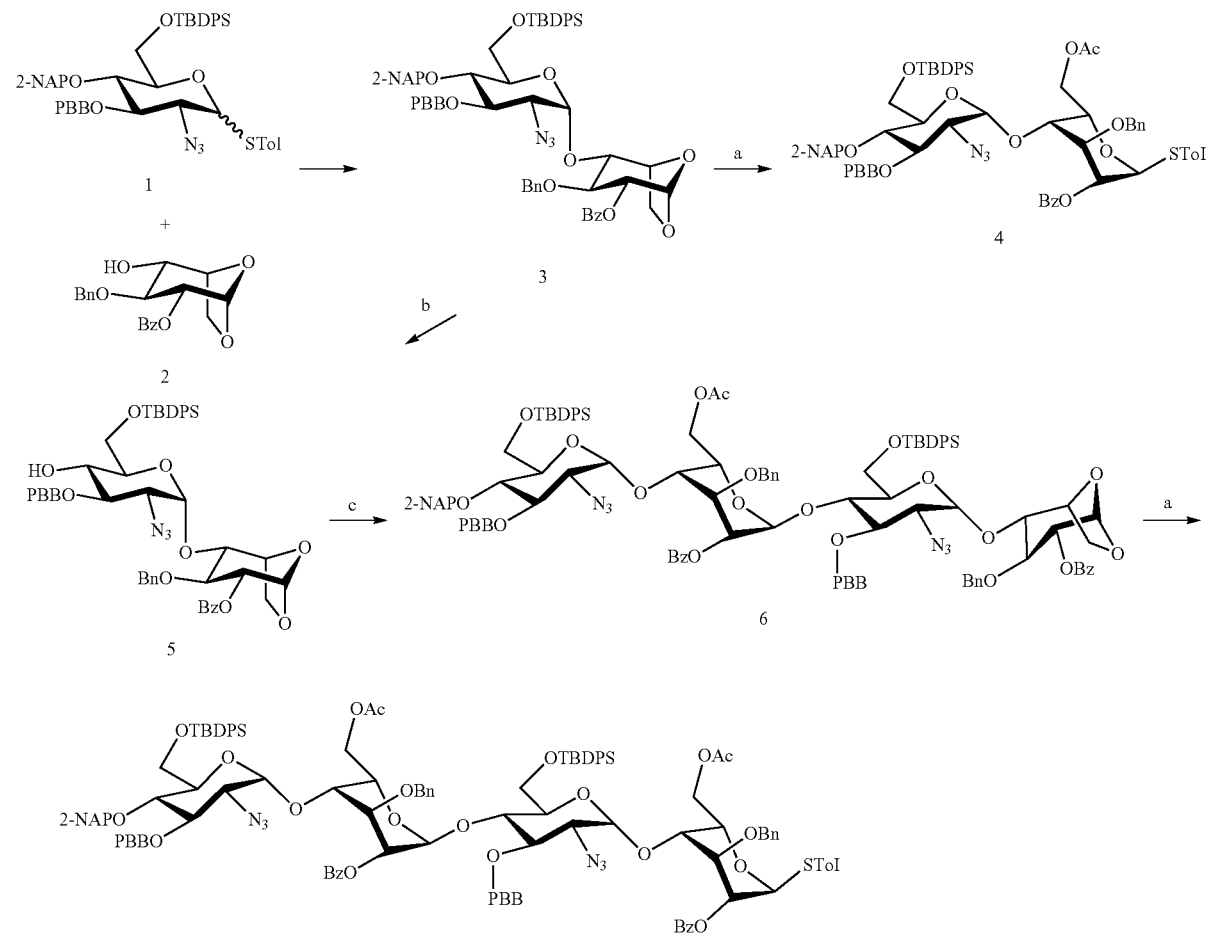

the correlation between the 2-H and 6-C of the internal L-iduronyl residue in the HMBC spectra and by the relatively high IR C=O stretching band observed around 1790 cm$^{-1}$. Further 6-O-desilylation by tetra-n-butylammonium fluoride (TBAF), lactone ring opening under basic conditions, and O-sulfonation of all free hydroxy groups with SO$_3$.Et$_3$N furnished the sulfate derivatives 15, 16, and 17 in three steps in 66%, 78%, and 30% overall yields, respectively. Finally, the individual target compounds 18 (90%), 19 (85%), and 20 (70%) were generated from 15-17 through a 3-step transformation including the Staudinger reduction of the azido groups to the amino groups, the N-sulfation of all primary amines, and the Pd(OH)$_2$/C-mediated hydrogenolysis to cleave all benzyl, PBB, 2-NAP, and Cbz groups. Due to frequent peak overlap, the direct assignments of protons in the NMR spectra for the tetrasaccharide 19, and hexasaccharide 20 were difficult. The molecular weights of compounds 18 (M+H$^+$, calculated for C$_{17}$H$_{29}$N$_2$O$_{20}$S$_3$Na$_4^+$ 769.0067, found 769.0076), 19 (M+H$^+$, calculated for C$_{29}$H$_{44}$N$_3$O$_{39}$S$_6$Na$_8^+$ 1433.9058, found 1433.9055) and 20 (M−4H$^{4-}$, calculated for C$_{41}$H$_{66}$N$_4$O$_{58}$S$_9^{4-}$ 457.4951, found 457.4981) were further confirmed by high resolution electrospray ionization mass spectra.

Scheme 2 Synthesis of HS oligosaccharides 18, 19 and 20

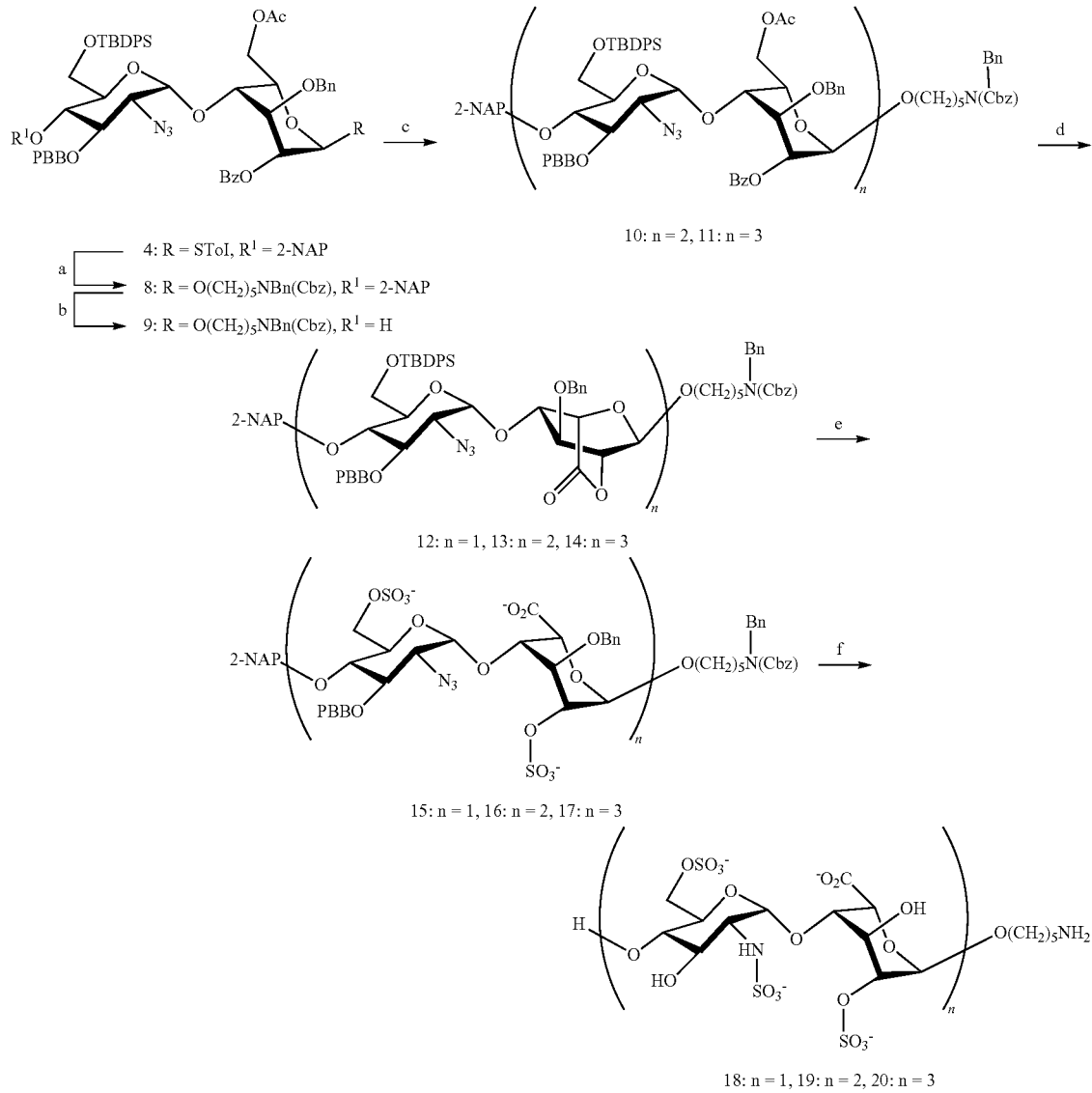

Reagents and conditions: (a) HO(CH$_2$)$_5$N(Bn)Cbz, NIS, TfOH, 3 Å MS, CH$_2$Cl$_2$/CH$_3$CN (1/2, v/v), 78 C to −40 C, 3 h; 77%; (b) DDQ, CH$_2$Cl$_2$/H$_2$O (18/1, v/v), 4 h; 75%; (c) NIS, TfOH, 3 Å molecular sieves, CH$_2$Cl$_2$, 78 C to −40 C, 3 h; 10 (n=2, from 4+9): 81%, 11 (n=3, from 7+9): 82%; (d) (1) NaOMe, CH$_2$Cl$_2$/MeOH (1/1, v/v), rt, 18 h; (2) TEMPO, BAIB, H$_2$O/CH$_2$Cl$_2$ (1/2, v/v), rt, 16 h; 12: 67% (2 steps), 13: 70% (2 steps), 14: 80% (2 steps); (e) (1) 1M TBAF, THF, 50° C., 1 d; (2) LiOH, rt, 3 h; (3) SO$_3$.Et$_3$N, DMF, 16 h; 15: 66% (3 steps), 16: 78% (3 steps), 17: 30% (3 steps); (f) (1) 1 M PMe$_3$/THF, THF, NaOH$_{(aq)}$, rt, 5 h; (2) SO$_3$.pyridine, Et$_3$N, NaOH$_{(aq)}$, MeOH, rt, 1 d; (3) Pd(OH)$_2$/C, H$_2$ (balloon), MeOH, phosphate buffer (pH=7), rt, 2 d; 18: 90% (3 steps), 19: 85% (3 steps), 20: 70% (3 steps). BAIB, [bis(acetoxy)iodo]benzene; Cbz, benzylooxycarbonyl; THF, tetrahydrofuran.

The chemical data of HS oligosaccharides of the present disclosure are provided bellowed.

Compound 7.

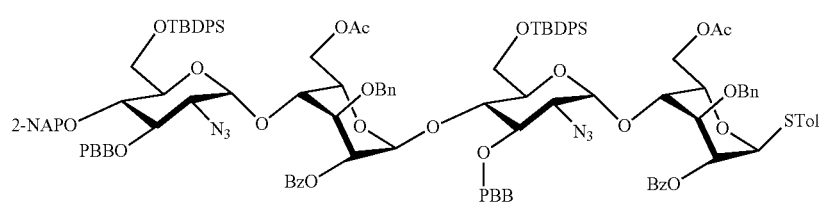

¹H NMR (600 MHz, CDCl₃) δ 8.11-8.08 (m, 2H, Bz-H), 8.00-7.97 (m, 2H, Bz-H), 7.85 (dd, J=6.0, 3.4 Hz, 1H, Ar—H), 7.78-7.73 (m, 2H, Ar—H), 7.67 (dd, J=7.9, 1.2 Hz, 2H, Ar—H), 7.65-7.62 (m, 2H, Ar—H), 7.60 (dd, J=7.9, 1.1 Hz, 2H, Ar—H), 7.58-7.54 (m, 3H, Ar—H), 7.52-7.48 (m, 2H, Ar—H), 7.48-7.44 (m, 4H, Ar—H), 7.43-7.35 (m, 13H, Ar—H), 7.35-7.32 (m, 3H, Ar—H), 7.32-7.28 (m, 4H, Ar—H), 7.28-7.24 (m, 5H, Ar—H), 7.24-7.20 (m, 4H, Ar—H), 7.15 (t, J=7.5 Hz, 2H, Ar—H), 7.11 (d, J=8.0 Hz, 2H, Ar—H), 7.00 (d, J=8.4 Hz, 2H, Ar—H), 6.86 (d, J=8.4 Hz, 2H, Ar—H), 5.54 (s, 1H, H-1), 5.36-5.33 (m, 2H, H-2, H-1″), 5.14 (bs, 1H, H-2″), 4.96 (d, J=11.6 Hz, 1H, ArCH₂), 4.85 (m, 4H, H-5, ArCH₂), 4.71 (d, J=11.4 Hz, 2H, ArCH₂), 4.65 (d, J=3.5 Hz, 1H, H-1‴), 4.51 (d, J=11.4 Hz, 1H, ArCH₂), 4.43 (d, J=3.8 Hz, 1H, H-1′), 4.36-4.31 (m, 2H, H-6a, ArCH₂), 4.28 (dt, J=7.0, 2.0 Hz, 1H, H-5″), 4.11-3.98 (m, 7H, H-3, H-6b, H-4′, H-6′a, H-3″, H-6″a, ArCH₂), 3.93 (dd, J=10.9, 7.0 Hz, 1H, H-6″b), 3.89-3.84 (m, 2H, H-6′b, ArCH₂), 3.82 (d, J=10.6 Hz, 1H, H-4‴), 3.77-3.72 (m, 2H, H-6‴), 3.72-3.68 (m, 1H, H-5‴), 3.67-3.62 (m, 1H, H-3‴), 3.62-3.58 (m, 1H, H-5′), 3.51-3.48 (m, 2H, H-4, H-4″), 3.45 (t, J=9.0 Hz, 1H, H-3′), 3.28 (dd, J=10.2, 3.5 Hz, 1H, H-2‴), 3.20 (dd, J=10.0, 3.8 Hz, 1H, H-2′), 2.33 (s, 3H, CH₃), 1.87 (s, 3H, CH₃), 1.69 (s, 3H, CH₃), 1.06 (s, 9H, 3 TBDPS), 0.97 (s, 9H, 3 TBDPS).

¹³C NMR (150 MHz, CDCl₃) δ 170.2 (C), 170.0 (C), 165.7 (C), 165.5 (C), 137.7 (C), 137.4 (C), 137.2 (C), 136.9 (C), 136.7 (C), 135.83 (CH), 135.90 (CH), 135.6 (CH), 135.5 (CH), 135.4 (C), 133.3 (C), 133.2 (C), 133.1 (C, CH), 132.90 (C), 132.86 (C), 132.3 (CH), 131.5 (C), 131.4 (CH), 130.8 (CH), 129.80 (CH), 129.77 (CH), 129.71 (CH), 129.69 (CH), 129.66 (CH), 129.61 (CH), 129.59 (CH), 129.55 (CH), 129.5 (CH), 128.8 (CH), 128.6 (CH), 128.5 (CH), 128.4 (CH), 128.3 (CH), 128.22 (CH), 128.15 (CH), 128.1 (CH), 128.0 (CH), 127.8 (CH), 127.70 (CH), 127.65 (CH), 127.6 (CH), 127.4 (CH), 127.3 (CH), 126.3 (CH), 126.2 (CH), 126.0 (CH), 125.7 (CH), 98.4 (CH), 97.8 (CH), 96.9 (CH), 86.2 (CH), 80.3 (CH), 79.1 (CH), 77.6 (CH), 75.1 (CH₂), 74.22 (CH), 74.15 (CH₂), 73.9 (CH₂), 73.7 (CH), 73.1 (CH), 72.78 (CH, CH₂), 72.75 (CH₂), 72.5 (CH), 72.4 (CH), 71.4 (CH), 69.7 (CH), 68.4 (CH), 66.1 (CH), 64.6 (CH), 64.2 (CH), 63.9 (CH), 62.9 (CH), 62.2 (CH₂), 62.1 (CH), 61.9 (CH₂), 26.8 (CH₃), 26.7 (CH₃), 21.1 (CH₃), 20.59 (CH₃), 20.57 (CH₃), 19.4 (C), 19.3 (C); HRMS m/z (MALDI, M+Na⁺) C₁₂₀H₁₂₄N₆O₂₂SBr₂Si₂Na⁺ 2273.3711, found 2273.3811.

Compound 8

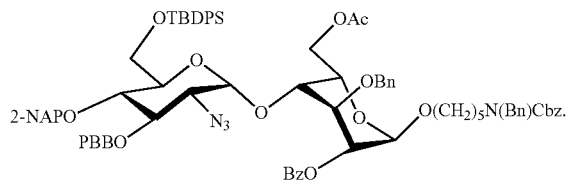

¹H NMR (600 MHz, CDCl₃) δ=8.18-8.15 (m, 2H, Ar—H), 7.88-7.86 (m, 1H, Ar—H), 7.81-7.79 (m, 2H, Ar—H), 7.72-7.69 (m, 4H, Ar—H), 7.62 (s, 1H, Ar—H), 7.55-7.53 (m, 2H, Ar—H), 7.43-7.34 (m, 26H, Ar—H), 7.18 (s, 1H, Ar—H), 7.04 (d, J=8.2 Hz, 2H, Ar—H), 5.22-5.18 (m, 3H, H-2, ArCH₂) 4.99-4.92 (m, 4H, H-1, ArCH₂), 4.80-4.76 (m, 2H, H-1′, ArCH₂), 4.54-4.50 (m, 3H, ArCH₂), 4.45-4.41 (m, 1H, H-6a), 4.38 (s, 1H, H-5), 4.21 (d, J=9.8 Hz, 1H, ArCH₂), 4.15 (dd, J=4.5, 11.1 Hz, 1H, H-6b), 4.12-4.11 (m, 1H, H-3), 4.07-4.05 (m, 1H, H-6′a), 3.92 (d, J=11.4 Hz, 1H, H-6′b), 3.87-3.78 (m, 5H, H-3′, H-4′, H-5′, H-4, linker CH₂), 3.48-3.43 (m, 1H, linker CH₂), 3.34 (dd, J=3.4, 10.1 Hz, 1H, H-2′), 3.28-3.21 (m, 2H, linker CH₂), 2.00-1.95 (m, 3H, OAc), 1.67-1.57 (m, 4H, linker CH₂), 1.36-1.31 (m, 2H, linker CH₂), 1.09 (s, 9H, TBDPS).

¹³C NMR (150 MHz, CDCl₃) δ=170.2 (C), 165.5 (C), 156.5 (C), 156.0 (C), 137.8 (C), 137.7 (C), 136.6 (C), 135.7 (CH), 135.4 (CH), 135.3 (C), 133.3 (C), 133.1 (C), 133.0 (CH), 132.89 (C), 132.87 (C), 131.3 (CH), 129.8 (CH), 129.7 (CH), 129.6 (CH), 129.5 (CH), 128.4 (CH), 128.3 (CH), 128.2 (CH), 128.1 (CH), 127.9 (CH), 127.8 (CH), 127.7 (CH), 127.6 (CH), 127.5 (CH), 127.2 (CH), 127.1 (CH), 127.0 (CH), 126.4 (CH), 126.2 (CH), 126.1 (CH), 125.9 (CH), 125.5 (CH), 121.6 (C), 98.3 (CH), 98.1 (CH), 80.5 (CH), 77.9 (CH), 77.8 (CH), 75.0 (CH₂), 74.3 (CH), 74.4 (CH₂), 72.9 (CH), 72.8 (CH), 72.3 (CH₂), 68.9 (CH), 67.8 (CH₂), 67.0 (CH₂), 65.5 (CH), 63.8 (CH), 62.8 (CH₂), 62.1 (CH₂), 50.4 (CH₂), 50.1 (CH₂), 47.0 (CH₂), 46.0 (CH₂), 26.7 (CH₃), 19.4 (C); HRMS m/z (ESI, M+Na⁺) calcd for C₈₂H₈₇N₄O₁₄SiBrNa⁺ 1481.5069, found 1481.5057.

Compound 9

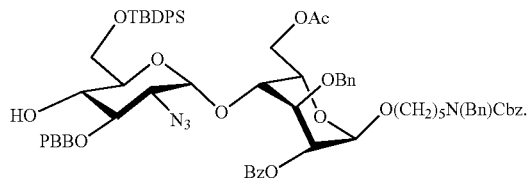

¹H NMR (600 MHz, CDCl₃) δ=8.14-8.11 (m, 2H, Ar—H), 7.66-7.63 (m, 4H, Ar—H), 7.51-7.38 (m, 21H, Ar—H), 7.23-7.20 (m, 4H, Ar—H), 7.14-7.11 (m, 3H, Ar—H), 5.19-5.13 (m, 3H, H-2, ArCH₂), 4.93 (d, J=10.5 Hz, 1H, H-1), 4.83 (d, J=11.1 Hz, 1H, ArCH₂), 4.72-4.67 (m, 2H, H-1', ArCH₂), 4.52 (d, J=11.0 Hz, 1H, ArCH₂), 4.47-4.44 (m, 2H, ArCH₂), 4.40-4.37 (m, 1H, H-6a), 4.34-4.31 (m, 1H, ArCH₂), 4.29-4.26 (m, 1H, H-5), 3.91-3.87 (m, 1H, H-6b), 4.04 (s, 1H, H-3), 3.91-3.87 (m, 1H, H-6'a), 3.81-3.77 (m, 1H, H-6'b), 3.73-3.68 (m, 4H, H-4, H-4', H-5', linker CH₂), 3.61-3.57 (m, 1H, H-3'), 3.44-3.37 (m, 1H, linker CH₂), 3.22-3.14 (m, 3H, H-2', linker CH₂), 1.95 (s, 3H, OAc), 1.53-1.47 (m, 4H, linker CH₂), 1.31-1.25 (m, 2H, linker CH₂), 1.02 (s, 9H, TBDPS).

¹³C NMR (150 MHz, CDCl₃) δ=170.4 (C), 165.7 (C), 156.7 (C), 156.1 (C), 137.9 (C), 137.7 (C), 137.0 (C), 135.6 (CH), 135.5 (CH), 133.2 (CH), 132.8 (C), 132.7 (C), 131.5 (CH), 129.97 (CH), 129.95 (CH), 129.8 (CH), 129.6 (CH), 128.55 (CH), 128.50 (CH), 128.3 (CH), 128.0 (CH), 127.89 (CH), 127.84 (CH), 127.2 (CH), 127.1 (CH), 121.7 (C), 98.2 (CH), 98.0 (CH), 80.2 (CH), 74.2 (CH₂), 73.9 (CH), 73.1 (CH), 72.5 (CH₂), 72.0 (CH), 69.4 (CH), 68.0 (CH₂), 67.1 (CH₂), 66.0 (CH), 64.0 (CH₂), 63.0 (CH), 50.5 (CH₂), 50.2 (CH₂), 47.1 (CH₂), 46.2 (CH₂), 29.1 (CH₂), 27.9 (CH₂), 27.5 (CH₂), 26.8 (CH₃), 23.4 (CH₂), 20.8 (CH₃), 19.4 (C); HRMS m/z (ESI, M+Na⁺) calcd for C₇₁H₇₉N₄O₁₄SiBrNa⁺ 1341.4436, found 1341.4443.

Compound 10

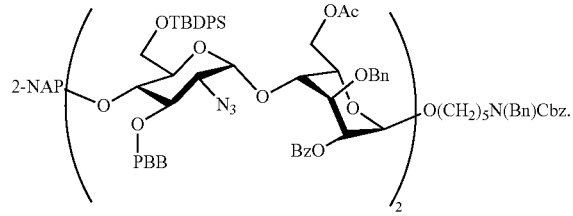

10

¹H NMR (600 MHz, CDCl₃) δ=8.24 (d, J=7.2 Hz, 2H, Ar—H), 8.13 (d, J=7.0 Hz, 2H, Ar—H), 7.93-7.80 (m, 12H, Ar—H), 7.57-7.41 (m, 45H, Ar—H), 7.12 (d, J=8.4 Hz, 2H, Ar—H), 7.05 (d, J=8.3 Hz, 2H, Ar—H), 5.54 (s, 1H, H-1″), 5.35-5.29 (m, 4H, H-2, H-2″, ArCH₂), 5.13-5.04 (m, 5H, H-1, ArCH₂), 4.87-4.77 (m, 5H, H-1', H-1‴, ArCH₂), 4.61-4.52 (m, 6H, H-6″a, ArCH₂), 4.26-4.12 (m, 12H, H-3, H-3″, H-5, H-5″, H-5‴, H-6, H-6', H-6″b, H-6‴), 3.92-3.78 (m, 8H, H-3', H-3‴, H-4, H-4', H-4″, H-4‴, H-5', linker CH₂), 3.59-3.52 (m, 1H, ArCH₂), 3.42 (dd, J=2.8, 10.3 Hz, 1H, H-2‴), 3.38-3.34 (m, 2H, H-2', linker CH₂), 3.30-3.25 (m, 1H, linker CH₂), 1.94 (d, J=9.3 Hz, 3H, OAc), 1.85 (s, 3H, OAc), 1.78-1.67 (m, 4H, linker CH₂), 1.48-1.41 (m, 2H, linker CH₂), 1.20 (s, 9H, TBDPS), 1.11 (s, 9H, TBDPS).

¹³C NMR (150 MHz, CDCl₃) δ=171.0 (C), 170.3 (C), 170.0 (C), 165.8 (C), 165.7 (C), 156.8 (C), 156.2 (C), 138.1 (C), 137.9 (C), 137.6 (C), 137.2 (C), 137.0 (C), 136.9 (C), 136.0 (CH), 136.0 (CH), 135.7 (CH), 135.6 (CH), 133.5 (C), 133.4 (C), 133.3 (C), 133.15 (C), 133.11 (C), 131.6 (CH), 131.4 (CH), 131.4 (CH), 131.1 (CH), 130.2 (CH), 130.0 (CH), 129.8 (CH), 129.8 (CH), 129.9 (CH), 129.9 (CH), 129.6 (CH), 129.1 (CH), 128.9 (CH), 128.7 (CH), 128.6 (CH), 128.6 (CH), 128.5 (CH), 128.4 (CH), 128.4 (CH), 128.3 (CH), 128.2 (CH), 128.0 (CH), 128.0 (CH), 127.9 (CH), 127.9 (CH), 127.8 (CH), 127.7 (CH), 127.6 (CH), 127.4 (CH), 127.3 (CH), 127.3 (CH), 126.6 (CH), 126.3 (CH), 126.2 (CH), 125.9 (CH), 121.8 (C), 121.1 (C), 98.6 (CH), 98.4 (CH), 97.6 (CH), 97.1 (CH), 80.5 (CH), 79.3 (CH), 77.9 (CH), 77.6 (CH), 77.4 (CH), 77.2 (CH), 75.3 (CH₂), 74.3 (CH₂), 74.1 (CH₂), 74.0 (CH), 73.8 (CH), 73.7 (CH), 73.2 (CH), 73.0 (CH₂), 72.9 (CH₂), 72.7 (CH), 72.6 (CH₂), 69.2 (CH), 68.6 (CH), 68.1 (CH₂), 67.2 (CH₂), 65.4 (CH), 64.8 (CH), 64.4 (CH), 64.2 (CH), 62.99 (CH₂), 62.94 (CH₂), 62.5 (CH₂), 62.2 (CH), 60.4 (CH₂), 50.7 (CH₂), 50.3 (CH₂), 47.3 (CH₂), 46.3 (CH₂), 29.2 (CH₂), 28.1 (CH₂), 27.6 (CH₂), 27.1 (CH₃), 26.9 (CH₃), 21.1 (CH₃), 20.8 (CH₃), 20.7 (CH₃), 19.6 (C), 19.5 (C), 14.4 (CH₃); HRMS m/z (ESI, M+2Na²⁺) calcd for C₁₃₃H₁₄₁N₇O₂₅Si₂Br₂Na₂²⁺ 1247.8839, found 1247.8829.

Compound 11

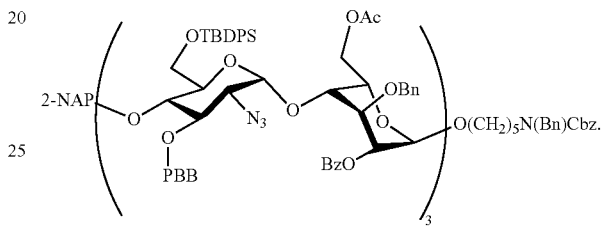

11

¹H NMR (600 MHz, CDCl₃) δ=8.12-8.10 (m, 2H, Ar—H), 8.00-7.98 (m, 4H, Ar—H), 7.86-7.84 (m, 1H, Ar—H), 7.78-7.75 (m, 2H, Ar—H), 7.68-7.67 (m, 2H, Ar—H), 7.63-7.60 (m, 11H, Ar—H), 7.55 (s, 1H, Ar—H), 7.51-7.50 (m, 2H, Ar—H), 7.43-7.38 (m, 24H, Ar—H), 7.31-7.28 (m, 21H, Ar—H), 7.22-7.17 (m, 13H, Ar—H), 7.00-6.99 (m, 2H, Ar—H), 6.92-6.90 (m, 4H, Ar—H), 5.40 (s, 1H), 5.35 (s, 1H), 5.19-5.14 (m, 5H), 4.96-4.94 (m, 1H), 4.89-4.84 (m, 5H), 4.70-4.62 (m, 8H), 4.49-4.47 (m, 2H), 4.36-4.30 (m, 5H), 4.12-4.04 (m, 13H), 3.90-3.85 (m, 5H), 3.76-3.61 (m, 12H), 3.38 (s, 1H), 3.28-3.20 (m, 5H), 1.85-1.82 (m, 3H), 1.68 (s, 3H), 1.64 (s, 3H), 1.61-1.53 (m, 4H), 1.33-1.28 (m, 2H), 1.06 (s, 9H), 0.99 (s, 9H), 0.97 (s, 9H).

¹³C NMR (150 MHz, CDCl₃) δ=170.2 (C), 170.0 (C), 169.9 (C), 165.79 (C), 165.70 (C), 165.5 (C), 156.7 (C), 156.2 (C), 138.0 (C), 137.7 (C), 137.38 (C), 137.36 (C), 137.09 (C), 137.00 (C), 136.8 (C), 135.9 (CH), 135.67 (CH), 135.63 (CH), 135.6 (CH), 135.5 (CH), 133.49 (CH), 133.40 (CH), 133.3 (CH), 133.26 (CH), 133.21 (CH), 133.1 (CH), 133.09 (CH), 133.00 (CH), 132.9 (CH), 131.5 (CH), 130.9 (CH), 129.87 (CH), 129.81 (CH), 129.78 (CH), 129.71 (CH), 129.6 (CH), 129.5 (CH), 129.0 (CH), 128.9 (CH), 128.8 (CH), 128.7 (CH), 128.6 (CH), 128.5 (CH), 128.46 (CH), 128.44 (CH), 128.3 (CH), 128.28 (CH), 128.26 (CH), 128.17 (CH), 128.11 (CH), 127.95 (CH), 127.91 (CH), 127.86 (CH), 127.80 (CH), 127.7 (CH), 127.67 (CH), 127.62 (CH), 127.5 (CH), 127.4 (CH), 127.28 (CH), 127.20 (CH), 126.4 (CH), 126.2 (CH), 126.0 (CH), 125.8 (CH), 121.7 (C), 121.09 (C), 121.02 (C), 98.5 (CH), 98.2 (CH), 97.4 (CH), 97.09 (CH), 97.02 (CH), 96.9 (CH), 80.4 (CH), 79.1 (CH), 78.9 (CH), 77.7 (CH), 75.2 (CH₂), 74.2 (CH₂), 74.0 (CH₂), 73.8 (CH), 73.7 (CH), 73.6 (CH), 73.03 (CH₂), 73.00 (CH), 72.9 (CH), 72.88 (CH₂), 72.83 (CH), 72.55 (CH₂), 72.51 (CH₂), 72.3 (CH), 72.2 (CH), 69.2 (CH), 68.8 (CH), 68.4 (CH), 68.0 (CH₂), 67.1 (CH₂), 65.5 (CH), 65.0 (CH), 64.5 (CH), 64.2 (CH), 64.0 (CH), 62.7 (CH), 62.38 (CH₂), 62.33 (CH₂), 62.18 (CH₂), 62.13 (CH₂), 62.0 (CH₂), 50.5 (CH₂), 50.2 (CH₂), 47.17 (CH₂), 46.19 (CH₂), 29.1

(CH₂), 27.9 (CH₂), 27.5 (CH₂), 26.9 (CH₃), 26.8 (CH₃), 26.8 (CH₃), 23.4 (CH₂), 20.7 (CH₂), 20.66 (CH₂), 20.60 (CH₂), 19.49 (C), 19.45 (C), 19.40 (C); HRMS m/z (ESI, M+H⁺) calcd for $C_{184}H_{196}Br_3N_{10}O_{36}Si_3^+$ 3442.4810, found 3442.4816.

Compound 12

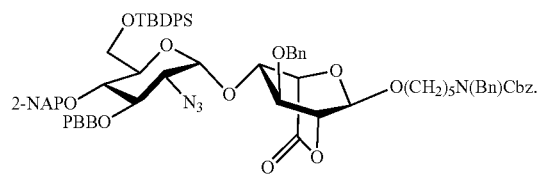

¹H NMR (600 MHz, CDCl₃) δ=7.86-7.84 (m, 1H, Ar—H), 7.79-7.75 (m, 4H, Ar—H), 7.70-7.65 (m, 3H, Ar—H), 7.52-7.50 (m, 2H, Ar—H), 7.45-7.43 (m, 2H, Ar—H), 7.41-7.34 (m, 21H, Ar—H), 7.22-7.19 (m, 3H, Ar—H), 5.24-5.19 (m, 2H, ArCH₂) 5.13-5.07 (m, 2H, H-1, H-1'), 4.98-4.88 (m, 4H, ArCH₂), 4.77-4.71 (m, 2H, ArCH₂), 4.60-4.53 (m, 3H, H-2, ArCH₂), 4.41 (d, J=3.1 Hz, 1H, H-5), 4.28-4.24 (m, 1H, H-4), 4.04-4.00 (m, 2H, H-6'), 3.95-3.92 (m, 2H, H-3, H-3'), 3.88-3.81 (m, 3H, H-4', H-5', linker CH₂), 3.52-3.43 (m, 2H, H-2', linker), 3.31.-3.24 (m, 2H, linker), 1.72-1.59 (m, 4H, linker CH₂), 1.42-1.32 (m, 2H, linker CH₂), 1.09 (s, 9H, TBDPS).

¹³C NMR (150 MHz, CDCl₃) δ=167.6 (C), 156.6 (C), 156.1 (C), 137.8 (C), 137.2 (C), 136.7 (C), 135.8 (CH), 135.5 (CH), 135.2 (C), 133.3 (C), 133.1 (C), 132.9 (C), 132.8 (C), 131.4 (CH), 129.6 (CH), 129.5 (CH), 128.6 (CH), 128.4 (CH), 128.3 (CH), 128.1 (CH), 127.9 (CH), 127.8 (CH), 127.7 (CH), 127.6 (CH), 127.4 (CH), 127.2 (CH), 127.0 (CH), 126.0 (CH), 125.8 (CH), 125.4 (CH), 121.7 (C), 99.7 (CH), 96.8 (CH), 80.3 (CH), 79.6 (CH), 79.4 (CH), 78.0 (CH), 74.9 (CH₂), 74.5 (CH₂), 72.6 (CH), 72.1 (CH), 72.0 (CH₂), 69.4 (CH₂), 69.3 (CH), 67.1 (CH₂), 63.2 (CH), 62.1 (CH₂), 50.4 (CH₂), 50.1 (CH₂), 47.0 (CH₂), 46.0 (CH₂), 29.0 (CH₂), 26.8 (CH₃), 19.2 (C); HRMS m/z (ESI, M+Na⁺) calcd for $C_{73}H_{77}N_4O_{12}SiBrNa^+$ 1331.4388, found 1331.4397.

Compound 13

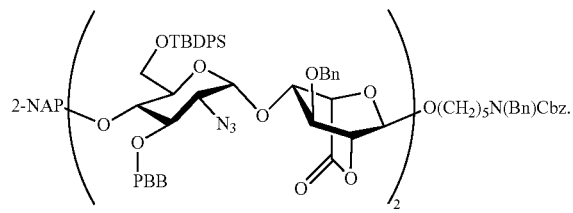

¹H NMR (600 MHz, CDCl₃) δ=7.91-7.88 (m, 1H, Ar—H), 7.84-7.81 (m, 4H, Ar—H), 7.75-7.71 (m, 7H, Ar—H), 7.57-7.54 (m, 4H, Ar—H), 7.50-7.45 (m, 20H, Ar—H), 7.39-7.35 (m, 13H, Ar—H), 7.29-7.25 (m, 6H, Ar—H), 5.50 (s, 1H, H-1''), 5.27-5.11 (m, 7H, H-1, H-1', ArCH₂), 4.90-4.71 (m, 10H, H-2, H-2'', ArCH₂), 4.38-4.31 (m, 5H, H-1''', H-3'', H-5, H-5'', ArCH₂), 4.13 (t, 1H, H-4''), 4.08-4.07 (m, 1H, H-6'a), 3.99-3.88 (m, 11H, H-3, H-3', H-3''', H-4, H-4''', H-5', H-5''', H-6'b, H-6''', linker CH₂), 3.73-3.72 (m, 1H, H-4'), 3.57-3.51 (m, 1H, linker CH₂), 3.44-3.42 (m, 1H, H-2'), 3.37 (dd, J=3.7, 10.2 Hz, 1H, H-2'''), 3.34-3.28 (m, 2H, linker CH₂), 1.75-1.64 (m, 4H, linker CH₂), 1.45-1.38 (m, 2H, linker CH₂), 1.16 (s, 9H, TBDPS), 1.11 (s, 9H, TBDPS).

¹³C NMR (150 MHz, CDCl₃) δ=167.8 (C), 167.1 (C), 156.2 (C), 137.9 (C), 137.6 (C), 137.2 (C), 136.9 (C), 136.8 (C), 136.7 (C), 136.0 (CH), 135.9 (CH), 135.6 (CH), 135.57 (CH), 135.52 (C), 133.6 (C), 133.3 (C), 133.0 (C), 132.8 (C), 132.7 (C), 131.64 (CH), 131.60 (CH), 130.0 (CH), 129.88 (CH), 129.80 (CH), 129.7 (CH), 129.7 (CH), 128.6 (CH), 128.58 (CH), 128.55 (CH), 128.50 (CH), 128.2 (CH), 128.08 (CH), 128.01 (CH), 127.9 (CH), 127.8 (CH), 127.79 (CH), 127.75 (CH), 127.69 (CH), 127.60 (CH), 127.3 (CH), 127.2 (CH), 126.2 (CH), 126.1 (CH), 125.9 (CH), 125.5 (CH), 121.9 (C), 121.2 (C), 99.8 (CH), 99.5 (CH), 97.1 (CH), 96.9 (CH), 80.7 (CH), 80.4 (CH), 79.8 (CH), 79.4 (CH), 78.4 (CH), 78.0 (CH), 77.8 (CH), 77.3 (CH), 77.1 (CH), 76.9 (CH), 76.4 (CH), 75.1 (CH₂), 74.7 (CH₂), 73.5 (CH₂), 72.7 (CH), 72.4 (CH), 72.3 (CH), 72.2 (CH), 72.1 (CH₂), 69.6 (CH₂), 69.5 (CH), 69.2 (CH), 67.2 (CH₂), 63.4 (CH), 63.1 (CH), 61.9 (CH₂), 61.7 (CH₂), 50.5 (CH₂), 50.2 (CH₂), 47.2 (CH₂), 46.1 (CH₂), 29.2 (CH₂), 26.99 (CH₃), 26.95 (CH₃), 23.2 (CH₂), 19.4 (C), 19.2 (C); HRMS m/z (ESI, M+Na⁺) calcd for $C_{115}H_{121}N_7O_{21}Si_2Br_2Na^+$ 2175.6434, found 2175.6418.

Compound 14

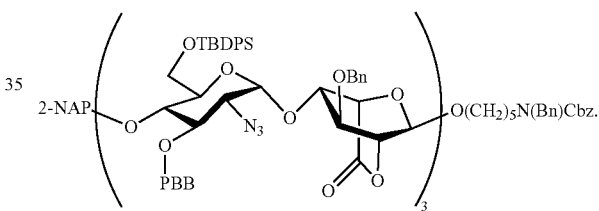

¹H NMR (600 MHz, CDCl₃) δ=7.70 (s, 1H, Ar—H), 7.64-7.57 (m, 16H, Ar—H), 7.37-7.35 (m, 5H, Ar—H), 7.31-7.27 (m, 29H, Ar—H), 7.20-7.13 (m, 23H, Ar—H), 5.34 (s, 2H), 5.09-5.00 (m, 4H), 4.87-4.83 (m, 4H), 4.72-4.64 (m, 4H), 4.54-4.44 (m, 10H), 4.20-4.12 (m, 8H), 3.96-3.91 (m, 3H), 3.81-3.75 (m, 6H), 3.65-3.58 (m, 11H), 3.45-3.43 (m, 1H), 3.26-3.16 (m, 5H), 1.50-1.43 (m, 4H), 1.25-1.19 (m, 2H), 0.99-0.96 (m, 27H).

¹³C NMR (150 MHz, CDCl₃) δ=167.7 (C), 167.1 (C), 167.0 (C), 156.6 (C), 156.1 (C), 137.8 (C), 137.5 (C), 137.4 (C), 137.1 (C), 136.8 (C), 136.79 (C), 136.75 (CH), 135.9 (CH), 135.8 (CH), 135.7 (CH), 135.5 (CH), 135.45 (CH), 135.43 (CH), 133.5 (C), 133.2 (C), 132.89 (C), 132.86 (C), 132.83 (C), 132.7 (C), 132.5 (C), 132.4 (C), 131.5 (CH), 131.49 (CH), 131.45 (CH), 129.9 (CH), 129.8 (CH), 129.79 (CH), 129.70 (CH), 129.6 (CH), 128.5 (CH), 128.46 (CH), 128.44 (CH), 128.3 (CH), 128.1 (CH), 128.1 (CH), 127.9 (CH), 127.89 (CH), 127.87 (CH), 127.7 (CH), 127.67 (CH), 127.63 (CH), 127.60 (CH), 127.57 (CH), 127.50 (CH), 127.2 (CH), 127.09 (CH), 126.07 (CH), 125.8 (CH), 125.4 (CH), 121.7 (C), 121.18 (C), 121.13 (C), 99.7 (CH), 99.37 (CH), 99.32 (CH), 97.0 (CH), 96.9 (CH), 96.8 (CH), 80.6 (CH), 80.4 (CH), 80.2 (CH), 79.7 (CH), 79.2 (CH), 78.3 (CH), 78.2 (CH), 77.9 (CH), 76.9 (CH), 76.7 (CH), 76.36 (CH), 76.32 (CH), 75.0 (CH₂), 74.6 (CH₂), 73.5 (CH₂), 73.4 (CH₂), 72.6 (CH), 72.2 (CH), 72.17 (CH), 72.14 (CH), 72.0

(CH$_2$), 69.5 (CH$_2$), 69.3 (CH), 69.0 (CH), 67.1 (CH$_2$), 63.3 (CH), 63.1 (CH), 63.0 (CH), 61.7 (CH$_2$), 61.6 (CH$_2$), 61.3 (CH$_2$), 50.4 (CH$_2$), 50.1 (CH$_2$), 47.0 (CH$_2$), 46.0 (CH$_2$), 29.1 (CH$_2$), 27.7 (CH$_2$), 27.2 (CH$_2$), 26.86 (CH$_3$), 26.83 (CH$_3$), 23.1 (CH$_2$), 19.2 (C), 19.1 (C), 19.0 (C); HRMS m/z (ESI, M+Na$^+$) calcd for C$_{157}$H$_{165}$Br$_3$N$_{10}$O$_{30}$Si$_3$Na$^+$ 3019.0520, found 3019.0515.

Compound 18

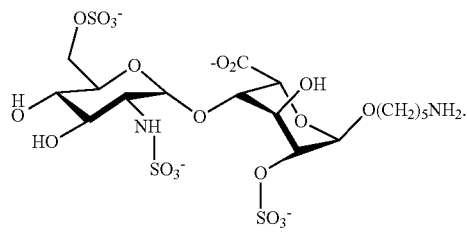

$^1$H NMR (600 MHz, D$_2$O) δ=5.39 (s, 1H, H-1'), 5.17 (s, 1H, H-1), 4.53 (s, 1H, H-5), 4.46-4.39 (m, 1H, H-6'b), 4.33-4.24 (m, 3H, H-2, H-3, H-6'a), 4.08 (m, 2H, H-4), 4.04-3.98 (m, 1H, H-5'), 3.81-3.69 (m, 4H, H-3', H-4', linker CH$_2$), 3.36-3.28 (m, 1H, H-2'), 3.11-3.03 (m, 2H, linker CH$_2$), 1.85-1.71 (m, 4H, linker CH$_2$), 1.58-1.47 (m, 2H, linker CH$_2$).

$^{13}$C NMR (150 MHz, D$_2$O) δ=174.8 (C), 98.6 (CH), 97.0 (CH), 75.7 (CH), 75.6 (CH), 70.9 (CH), 69.6 (CH), 69.1 (CH), 68.3 (CH), 68.3 (CH), 68.1 (CH$_2$), 66.4 (CH$_2$), 57.9 (CH), 39.4 (CH$_2$), 27.8 (CH$_2$), 26.2 (CH$_2$), 22.2 (CH$_2$); HRMS m/z (ESI, M+H$^+$) calcd for C$_{17}$H$_{29}$N$_2$O$_{20}$S$_3$Na$_4^+$ 769.0067, found 769.0076.

Compound 19

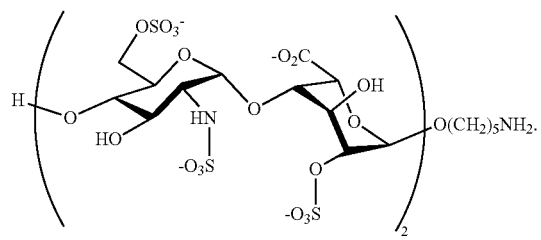

$^1$H NMR (600 MHz, D$_2$O) δ=5.49-5.43 (m, 2H, H-1', H-1'''), 5.26 (s, H-1''), 5.16 (s, 1H, H-1), 4.87 (s, 1H, H-5''), 4.53 (s, 1H, H-5), 4.45-4.34 (m, 8H, H-2, H-2'', H-3, H-3'', H-6', H-6'''), 4.15-4.12 (m, 2H, H-4, H-4''), 4.07-4.04 (m, 2H, H-5', H-5'''), 3.83-3.70 (m, 6H, H-3', H-3''', H-4', H-4''', linker CH$_2$), 3.36-3.31 (m, 2H, H-2', H-2'''), 3.09-3.04 (m, 2H, linker CH$_2$), 1.75-1.69 (m, 4H, linker CH$_2$), 1.54-1.50 (m, 2H, linker CH$_2$).

$^{13}$C NMR (150 MHz, D$_2$O) δ=174.8 (C), 174.7 (C), 99.1 (CH), 98.9 (CH), 96.8 (CH), 96.7 (CH), 76.2 (CH), 75.8 (CH), 75.78 (CH), 75.72 (CH), 71.0 (CH), 69.9 (CH), 69.5 (CH), 69.2 (CH), 68.9 (CH), 68.7 (CH), 68.6 (CH), 68.1 (CH$_2$), 66.4 (CH$_2$), 66.3 (CH$_2$), 57.95 (CH), 57.92 (CH), 39.4 (CH$_2$), 27.8 (CH$_2$), 26.2 (CH$_2$), 22.2 (CH$_2$); HRMS m/z (ESI, M+H$^+$) C$_{29}$H$_{44}$N$_3$O$_{39}$Na$_8$S$_6^+$ 1433.9058, found 1433.9055.

Compound 20

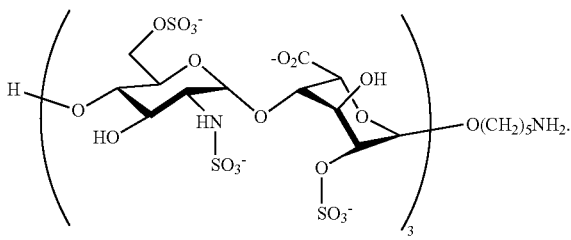

$^1$H NMR (600 MHz, D$_2$O) δ=5.44 (s, 3H), 5.24 (s, 2H), 5.12 (d, J=2.7 Hz, 1H), 4.85 (d, J=2.5 Hz, 1H), 4.84 (d, J=2.5 Hz, 1H), 4.52 (d, J=2.9 Hz, 1H), 4.45-4.40 (m, 5H), 4.31-4.29 (m, 2H), 4.26-4.23 (m, 2H), 4.26-4.23 (m, 5H), 4.15-4.12 (m, 3H), 4.08-4.04 (m, 3H), 3.83-3.80 (m, 3H), 3.72-3.69 (m, 4H), 3.59 (t, J=9.7 Hz, 1H), 3.32-3.30 (m, 2H), 3.26 (dd, J=3.2, 10.3 Hz, 1H), 3.04-3.02 (m, 2H), 1.74-1.70 (m, 4H), 1.51-1.48 (m, 2H).

$^{13}$C NMR (150 MHz, D$_2$O) δ=174.8 (C), 174.58 (C), 174.51 (C), 99.2 (CH), 99.1 (CH), 99.0 (CH), 96.8 (CH), 96.5 (CH), 96.4 (CH), 76.8 (CH), 75.95 (CH), 75.91 (CH), 75.7 (CH), 75.6 (CH), 70.9 (CH), 69.8 (CH), 69.49 (CH), 69.44 (CH), 69.3 (CH), 69.2 (CH), 69.1 (CH), 69.1 (CH), 69.0 (CH), 67.9 (CH$_2$), 66.37 (CH$_2$), 66.31 (CH$_2$), 57.8 (CH$_2$), 39.3 (CH$_2$), 27.8 (CH$_2$), 26.1 (CH$_2$), 22.1 (CH$_2$); HRMS m/z (ESI, M-4H$^{4-}$) calcd for C$_{41}$H$_{66}$N$_4$O$_{58}$S$_9^{4-}$ 457.4951, found 457.4981.

1.3 Screening of Sulf-1 Substrates Based on Competition Assay with 4-MUS.

HS oligosaccharides of Example 1.2 were used as competing substrates in the presence of 4-MUS for the identification of Sulf-1 substrate. Compounds 18-20 as well as the commercially available heparin 3000 were independently assessed for their competing effect on 4-MUS cleavage by Sulf-1 to yield the fluorescent 4-methylumbelliferone (4-MU) (FIG. 1, (A)). The fluorescence intensity at the emission wavelength of 460 nm (excitation wavelength at 355 nm) was measured and the generic 4-MUS hydrolysis in pure water was considered as 100%. When purified Sulf-1 was incubated with the disaccharide 18 (320 μM) as a competitor of 4-MUS (4.35 mM), the resulting fluorescence (94.5%) was similar to that of the control, indicating that 18 was unable to block the entry of 4-MUS into the Sulf-1 active site (FIG. 1, (B)). On the other hand, results from tetrasaccharide 19, hexasaccharide 20, and heparin 3000 indicated that four or more sugar units strongly compete with 4-MUS.

To better understand the structural requirements by Sulf-1 in its substrates, an array of the HS tetrasaccharides (i.e., compounds 21-35, FIG. 1(C)) having N—Ac/SO$_3^-$ and (6-O—SO$_3^-$ at the GlcN units and 2-O—H/SO$_3^-$ at the GlcA/IdoA units was assayed as competing binders against 4-MUS. This systematic study revealed that compound 31 is also a good binder in addition to compound 19, indicating that the 2-O-sulfated IdoA unit near the nonreducing end is essential and the N-sulfate groups at GlcN and the 2-O-sulfate groups of GlcA/IdoA at the reducing end play important roles in the interaction with Sulf-1. Both 19 and 31 exhibited the EC$_{50}$ values of 87.8 μM and 151 μM, respectively.

Example 2 Synthesis of the HS Trisaccharide 36 and its Competition Assay

Based on the results of Example 1.3, the HS trisaccharide 36 (depicted below), lacking the GlcN unit at the nonreducing end of 19, was chosen for further investigation.

Compound 36

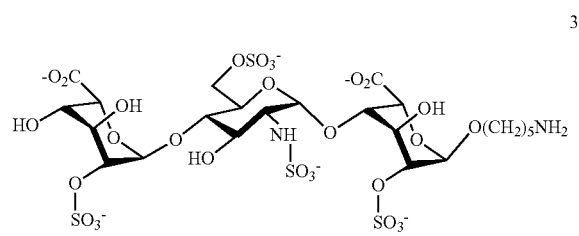

Compound 36 was prepared from our previously synthesized L-ido donor 37 and the disaccharide acceptor 9 in accordance with steps described in Scheme 3. Coupling of 37 and 9 in the presence of NIS and TfOH furnished the desired-linked trisaccharide 38 (82%), which then underwent sequential deacylation under Zemplén's conditions and TEMPO oxidation to afford the lactone 39 in 70% yield (2 steps). Ring opening of the lactone 39 in methanol and triethylamine delivered the methyl ester 40 (89%), which was subjected to O-sulfation with $SO_3.Et_3N$ yielding the 2,2''-di-O-sulfated derivative 41 (79%). Desilylation of 41 with HF.Pyr at the 6'-O position gave the desired 6'-alcohol 42 (87%), which was further 0-sulfated to provide the trisulfate 43 in 84% yield. A 3-step conversion of compound 43 via consecutive demethylation ($H_2O_2$/LiOH) of two carboxylic ester groups, Staudinger reduction ($PMe_3$) of the azido group, and sulfation ($SO_3$.Pyr) of the primary amino group afforded the corresponding N- and O-sulfated product 44 in 52% overall yield. Global deprotection of compound 44 under hydrogenolysis conditions was successfully carried out and the target molecule 36 was obtained in 74% yield after purification through Sephadex G25 and ion-exchange chromatography with Dowex 50WX8-$Na^+$ resin. The chemical structures of the final compound 36 and intermediates were confirmed by extensive two-dimensional NMR experiments (see the Supplementary Information). The evidence was further corroborated with high resolution ESI-MS ($[M-2H]^{2-}$, calculated for $C_{23}H_{38}N_2O_{29}S_4^{2-}$ 467.0216, found 467.0247).

Scheme 3. Preparation of Heparan Sulfate Trisaccharide 36.

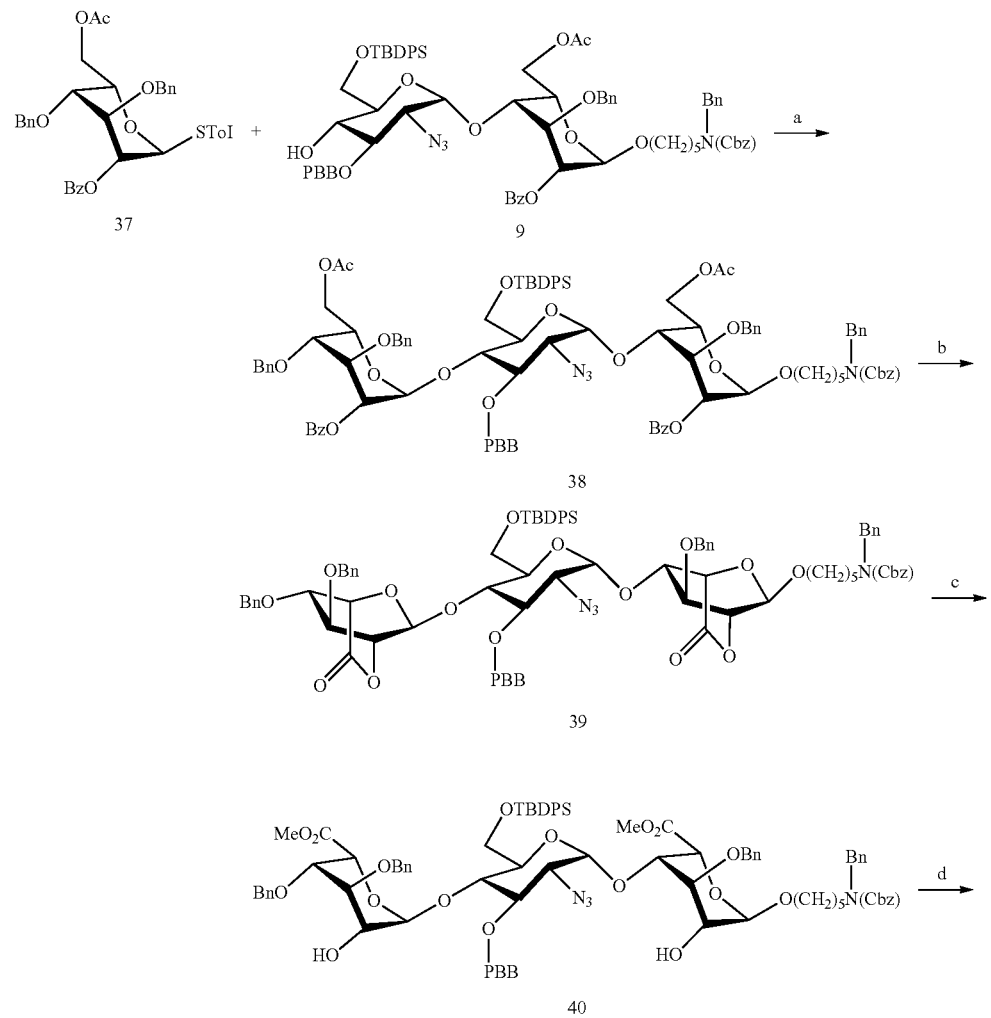

-continued
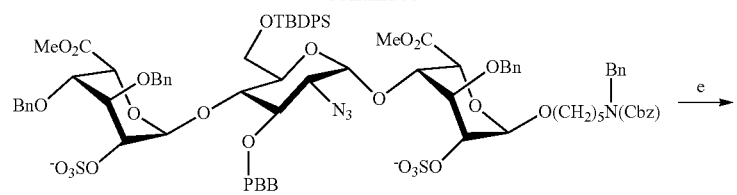
41
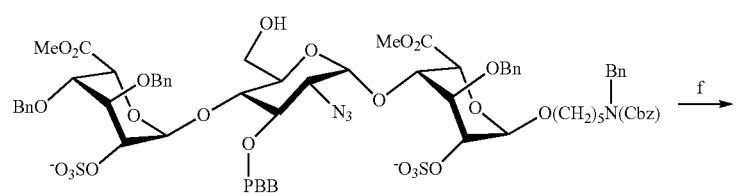
42
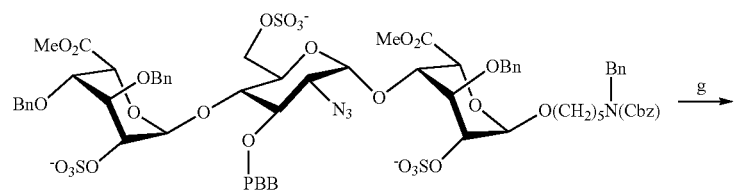
43
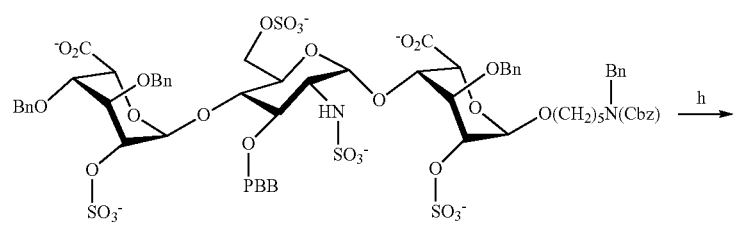
44
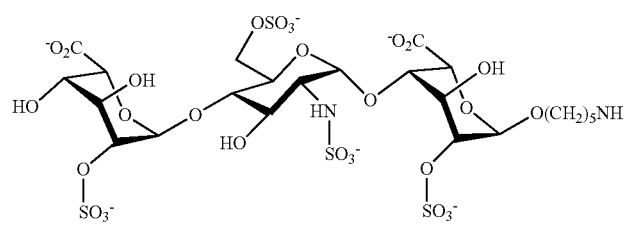
36

Reagents and conditions: (a) NIS, TfOH, 3 molecular sieves, CH$_2$Cl$_2$, 78 C to −40 C, 4 h, 82%; (b) (1) NaOMe, CH$_2$Cl$_2$/MeOH (1/1, v/v), rt, 18 h; (2) TEMPO, BAIB, H$_2$O/CH$_2$Cl$_2$ (1/2, v/v), rt, 16 h, 70% (2 steps); (c) MeOH, Et$_3$N, CH$_2$Cl$_2$, 40 C, 18 h, 89%; (d) SO$_3$.Et$_3$N, DMF, 60 C, 18 h, 79%; (e) HF.Pyr, Pyr, THF, 72 h, 87%; (f) SO$_3$.Et$_3$N, DMF, 60 C, 18 h, 84%; (g) (1) LiOH$_{(aq)}$, H$_2$O$_2$, THF, 37° C., 18 h; (2) PMe$_3$/THF, THF, NaOH$_{(aq)}$, rt, 14 h; (3) SO$_3$.Pyr, Et$_3$N, NaOH$_{(aq)}$, MeOH, rt, 18 h, 52% (3 steps); (h) Pd(OH)$_2$/C, H$_2$ (balloon), MeOH, phosphate buffer (pH=7), rt, 3 d, 7400.

Compound 38

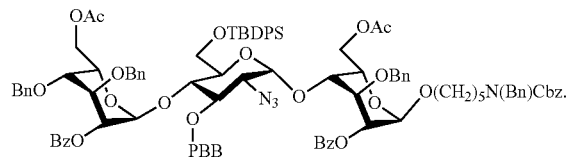

38

$^1$H NMR (600 MHz, CDCl$_3$) δ=8.20-8.14 (m, 2H, Ar—H), 7.94 (d, J=8.1 Hz, 2H, Ar—H), 7.65 (d, J=7.7 Hz, 2H, Ar—H), 7.60-7.56 (m, 3H, Ar—H), 7.46-7.35 (m, 33H, Ar—H), 7.21-7.17 (m, 5H, Ar—H), 6.96 (d, J=8.0 Hz, 2H, Ar—H), 5.37 (s, 1H, H-1''), 5.28-5.20 (m, 4H, H-2, H-2'', ArCH$_2$), 5.02-4.92 (m, 3H, H-1, ArCH$_2$), 4.76-4.67 (m, 4H, H-1', ArCH$_2$), 4.55-4.51 (m, 3H, ArCH$_2$), 4.43-4.36 (m, 4H, H-5, H-5'', H-6''b, ArCH$_2$), 4.19-4.05 (m, 8H, H-3, H-3'', H-4'', H-6, H-6'b, H-6''a, ArCH$_2$), 4.82-3.70 (m, 5H, H-3', H-4, H-5', H-6'a, linker CH$_2$), 3.53-3.43 (m, 2H, H-4', linker CH$_2$), 3.30-3.21 (m, 3H, H-2', linker CH$_2$), 1.92-1.83 (m, 6H, OAc), 1.68-1.58 (m, 4H, linker CH$_2$), 1.41-1.31 (m, 2H, linker CH$_2$), 0.99 (s, 9H, TBDPS).

$^{13}$C NMR (150 MHz, CDCl$_3$) δ=170.3 (C), 170.2 (C), 165.7 (C), 165.6 (C), 156.7 (C), 156.1 (C), 137.7 (C), 137.5 (C), 137.5 (C), 137.1 (C), 135.9 (CH), 135.5 (CH), 133.4 (CH), 133.2 (CH), 133.1 (CH), 130.9 (CH), 129.9 (CH), 129.8 (CH), 129.7 (CH), 129.69 (CH), 129.60 (CH), 129.5 (CH), 129.4 (CH), 128.9 (CH), 128.54 (CH), 128.51 (CH), 128.4 (CH), 128.34 (CH), 128.32 (CH), 128.1 (CH), 128.0 (CH), 127.9 (CH), 127.8 (CH), 127.5 (CH), 127.4 (CH), 127.3 (CH), 127.2 (CH), 127.1 (CH), 120.9 (C), 98.2 (CH), 97.3 (CH), 96.5 (CH), 79.0 (CH), 73.9 (CH$_2$), 73.5 (CH$_2$), 73.4 (CH), 73.1 (CH$_2$), 73.0 (CH), 72.8 (CH), 72.6 (CH), 72.5 (CH$_2$), 72.4 (CH), 72.0 (CH$_2$), 71.9 (CH), 69.2 (CH), 68.1 (CH), 68.0 (CH$_2$), 67.1 (CH$_2$), 65.6 (CH), 65.2 (CH), 64.2 (CH), 62.6 (CH$_2$), 62.5 (CH$_2$), 62.2 (CH$_2$), 50.5 (CH$_2$), 50.2 (CH$_2$), 47.1 (CH$_2$), 46.1 (CH$_2$), 29.1 (CH$_2$), 27.9 (CH$_2$), 27.5 (CH$_2$), 26.8 (CH$_3$), 26.7 (CH$_3$), 23.4 (CH$_2$), 20.7 (CH$_3$), 20.6 (CH$_3$), 19.4 (C); HRMS m/z (ESI, M+Na$^+$) calcd for C$_{100}$H$_{107}$N$_4$O$_{21}$SiBrNa$^+$ 1829.6278, found 1829.6244.

Compound 39

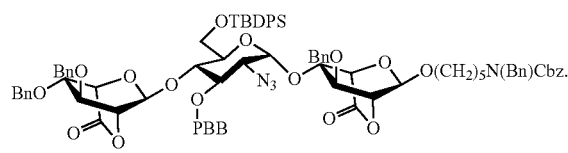

39

$^1$H NMR (600 MHz, CDCl$_3$) δ=7.66-7.62 (m, 4H, Ar—H), 7.45-7.34 (m, 27H, Ar—H), 7.23-7.22 (m, 2H, Ar—H), 7.20-7.14 (m, 6H, Ar—H), 5.42 (m, 1H, H-1''), 5.19-5.14 (m, 2H, ArCH$_2$), 5.08-5.02 (m, 2H, H-1', H-1''), 4.88-4.84 (m, 1H, ArCH$_2$), 4.70-4.60 (m, 4H, H-2, ArCH$_2$), 4.48-4.41 (m, 5H, H-5, H-5'', ArCH$_2$), 4.30-4.21 (m, 5H, H-2'', H-4', ArCH$_2$), 3.99-3.82 (m, 9H, H-3, H-3', H-3'', H-4, H-4'', H-5', H-6', linker CH$_2$), 3.46-3.39 (m, 1H, linker CH$_2$), 3.28-3.19 (m, 3H, H-2', linker CH$_2$), 1.64-1.54 (m, 4H, linker CH$_2$), 1.32-1.25 (m, 2H, linker CH$_2$), 1.02 (s, 9H, TBDPS).

$^{13}$C NMR (150 MHz, CDCl$_3$) δ=167.7 (C), 167.2 (C), 156.7 (C), 156.2 (C), 137.9 (C), 137.2 (C), 137.1 (C), 136.9 (C), 136.7 (C), 135.8 (CH), 135.6 (CH), 132.8 (C), 132.6 (C), 131.4 (CH), 130.0 (CH), 129.8 (CH), 129.1 (CH), 128.5 (CH), 128.4 (CH), 128.4 (CH), 128.2 (CH), 128.0 (CH), 128.0 (CH), 127.9 (CH), 127.8 (CH), 127.7 (CH), 127.6 (CH), 127.3 (CH), 127.1 (CH), 121.4 (C), 99.8 (CH), 98.2 (CH), 96.8 (CH), 80.6 (CH), 79.4 (CH), 79.3 (CH), 77.8 (CH), 77.7 (CH), 77.5 (CH), 73.8 (CH$_2$), 72.3 (CH), 72.2 (CH$_2$), 72.1 (CH$_2$), 71.9 (CH), 71.4 (CH$_2$), 69.6 (CH$_2$), 69.4 (CH), 68.5 (CH), 67.1 (CH$_2$), 63.0 (CH), 61.6 (CH$_2$), 50.5 (CH$_2$), 50.2 (CH$_2$), 47.1 (CH$_2$), 46.0 (CH$_2$), 29.1 (CH$_2$), 27.7 (CH$_2$), 27.3 (CH$_2$), 26.8 (CH$_3$), 19.2 (C); HRMS m/z (ESI, M+Na$^+$) calcd for C$_{82}$H$_{87}$N$_4$O$_{17}$SiBrNa$^+$ 1529.4917, found 1529.4907.

Compound 40

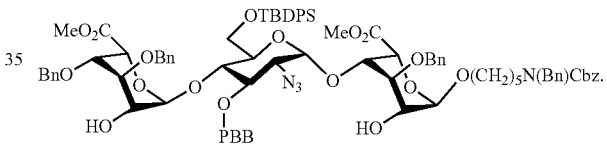

40

$^1$H NMR (600 MHz, CDCl$_3$) δ=7.71-7.69 (m, 4H, Ar—H), 7.39-7.32 (m, 28H, Ar—H), 7.22-7.14 (m, 7H, Ar—H), 5.32 (s, 1H, H-1''), 5.17-5.13 (m, 2H, ArCH$_2$), 4.97 (s, 1H, H-1), 4.91 (d, J=3.6 Hz, 1H, H-1'), 4.78-4.71 (m, 4H, H-2'', H-5, H-5'', ArCH$_2$), 4.56-4.48 (m, 8H, H-2, ArCH$_2$), 4.06-4.04 (m, 2H, H-3'', ArCH$_2$), 3.89-3.73 (m, 9H, H-3, H-3', H-4, H-4'', H-5', H-6', linker CH$_2$), 3.53-3.49 (m, 2H, H-2', H-4'), 3.42 (s, 3H, CO$_2$Me), 3.37 (s, 3H, CO$_2$Me), 3.21-3.15 (m, 2H, linker CH$_2$), 1.54-1.47 (m, 4H, linker CH$_2$), 1.28-1.24 (m, 2H, linker CH$_2$), 1.05 (s, 9H, TBDPS).

$^{13}$C NMR (150 MHz, CDCl$_3$) δ=169.8 (C), 169.3 (C), 156.7 (C), 156.1 (C), 137.8 (C), 137.5 (C), 137.4 (C), 136.8 (C), 136.6 (C), 135.9 (CH), 135.8 (CH), 133.3 (C), 133.2 (C), 131.1 (CH), 129.7 (CH), 129.6 (CH), 129.0 (CH), 128.6 (CH), 128.5 (CH), 128.5 (CH), 128.4 (CH), 128.3 (CH), 128.3 (CH), 128.2 (CH), 128.1 (CH), 127.9 (CH), 127.8 (CH), 127.8 (CH), 127.7 (CH), 127.6 (CH), 127.5 (CH), 127.3 (CH), 127.1 (CH), 121.1 (C), 99.8 (CH), 98.2 (CH), 96.8 (CH), 80.6 (CH), 79.4 (CH), 79.3 (CH), 73.8 (CH$_2$), 72.3 (CH), 72.8 (CH$_2$), 72.4 (CH$_2$), 72.2 (CH$_2$), 72.1 (CH$_2$), 71.9 (CH), 71.4 (CH$_2$), 69.6 (CH$_2$), 69.4 (CH), 67.1 (CH$_2$), 63.0 (CH), 61.6 (CH$_2$), 50.5 (CH$_2$), 50.2 (CH$_2$), 47.1 (CH$_2$), 46.0 (CH$_2$), 29.1 (CH$_2$), 27.7 (CH$_2$), 27.3 (CH$_2$), 26.8 (CH$_3$), 19.4 (C); HRMS m/z (ESI, M+Na$^+$) calcd for C$_{85}$H$_{95}$N$_4$O$_{19}$SiBrNa$^+$ 1593.5441, found 1593.5414.

Compound 41

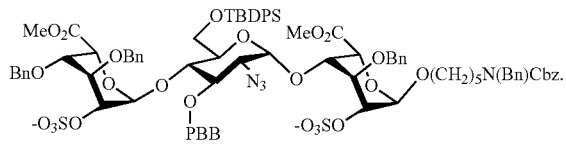

¹H NMR (600 MHz, CD₃OD) δ=7.83-7.80 (m, 4H, Ar—H), 7.47-7.44 (m, 6H, Ar—H), 7.39-7.32 (m, 16H, Ar—H), 7.25-7.17 (m, 13H, Ar—H), 5.54 (s, 1H, H-1″), 5.27 (d, J=3.5 Hz, 1H, H-1'), 5.19-5.14 (m, 3H, H-1, ArCH₂), 4.85-4.79 (m, 4H, H-5, H-5″, ArCH₂), 4.70-4.56 (m, 9H, H-2, H-2″, ArCH₂), 4.37-4.34 (m, 3H, H-3, H-3″, ArCH₂), 4.23 (dd, J=3.4, 12.1 Hz, 1H, H-6'a), 4.18 (t, J=9.4 Hz, 1H, H-4'), 4.06 (s, 1H, H-4″), 3.95 (d, J=11.2 Hz, 1H, H-6'b), 3.75-3.72 (m, 4H, H-3', CO₂Me), 3.65-3.62 (m, 3H, H-4, H-5', linker CH₂), 3.55-3.48 (m, 1H, linker CH₂), 3.31-3.28 (m, 4H, H-2', CO₂Me), 3.21-3.16 (m, 2H, linker CH₂), 1.62-1.52 (m, 4H, linker CH₂), 1.36-1.29 (m, 2H, linker CH₂), 1.06 (s, 9H, TBDPS).

¹³C NMR (150 MHz, CD₃OD) δ=170.2 (C), 169.9 (C), 157.0 (C), 156.5 (C), 137.9 (C), 137.8 (C), 137.4 (C), 137.3 (C), 136.6 (C), 135.9 (CH), 135.6 (CH), 133.5 (C), 133.3 (C), 130.6 (CH), 129.2 (CH), 129.2 (CH), 129.1 (CH), 128.4 (CH), 128.3 (CH), 128.2 (CH), 128.1 (CH), 128.0 (CH), 127.8 (CH), 127.7 (CH), 127.7 (CH), 127.6 (CH), 127.5 (CH), 127.4 (CH), 127.3 (CH), 127.2 (CH), 127.2 (CH), 127.1 (CH), 127.0 (CH), 126.8 (CH), 120.4 (C), 99.2 (CH), 98.3 (CH), 94.0 (CH), 78.4 (CH), 73.2 (CH₂), 72.7 (CH), 72.7 (CH), 72.3 (CH), 71.8 (CH₂), 71.7 (CH₂), 71.5 (CH), 71.3 (CH), 70.6 (CH₂), 70.3 (CH), 68.7 (CH), 67.9 (CH), 66.9 (CH), 66.9 (CH), 63.5 (CH), 62.2 (CH₂), 56.9 (CH₂), 51.7 (CH₃), 50.7 (CH₃), 50.1 (CH₂), 49.9 (CH₂), 28.8 (CH₂), 27.5 (CH₂), 27.0 (CH₂), 26.2 (CH₃), 23.1 (CH₂), 23.1 (CH₂), 18.9 (CH₃); HRMS m/z (ESI, M-2H²⁻) calcd for C₈₄H₉₅N₄O₂₅S₂BrSi²⁻ 864.2261, found 864.2258.

Compound 42

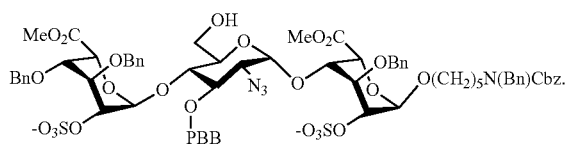

¹H NMR (600 MHz, CD₃OD) δ=7.43-7.40 (m, 4H, Ar—H), 7.31-7.23 (m, 20H, Ar—H), 7.13-7.10 (m, 3H, Ar—H), 7.01-6.98 (m, 2H, Ar—H), 5.30 (s, 1H, H-1″), 5.19 (d, J=3.6 Hz, 1H, H-1'), 5.15-5.09 (m, 3H, H-1, ArCH₂), 4.77-4.75 (m, 4H, H-5, ArCH₂), 4.69 (d, J=1.9 Hz, 1H, H-5″), 4.57-4.52 (m, 7H, H-2, H-2″, ArCH₂), 4.30 (s, 2H, H-3, ArCH₂), 4.22 (d, J=11.8 Hz, 1H, ArCH₂), 4.18 (s, 1H, H-3″), 4.09 (s, 1H, H-4), 3.92-3.89 (m, 2H, H-4', H-6'a), 3.81-3.78 (m, 1H, H-6'b), 3.74 (s, 3H, CO₂Me), 3.68-3.66 (m, 1H, H-3'), 3.56-3.54 (m, 3H, H-4″, H-5', linker CH₂), 3.48-3.42 (m, 1H, linker CH₂), 3.30-3.28 (m, 1H, H-2'), 3.18 (s, 3H, CO₂Me), 3.16-3.10 (m, 2H, linker CH₂), 1.60-1.48 (m, 4H, linker CH₂), 1.30-1.23 (m, 2H, linker CH₂).

¹³C NMR (150 MHz, CD₃OD) δ=170.5 (C), 170.4 (C), 157.0 (C), 156.5 (C), 147.9 (C), 137.9 (C), 137.8 (C), 137.5 (C), 137.2 (C), 137.0 (C), 136.7 (C), 136.6 (C), 130.7 (CH), 129.1 (CH), 128.5 (CH), 128.4 (CH), 128.2 (CH), 128.1 (CH), 128.0 (CH), 127.9 (CH), 127.7 (CH), 127.6 (CH), 127.5 (CH), 127.4 (CH), 127.3 (CH), 127.0 (CH), 127.0 (CH), 126.9 (CH), 120.5 (C), 99.3 (CH), 98.0 (CH), 95.1 (CH), 78.4 (CH), 73.4 (CH₂), 72.5 (CH), 72.4 (CH), 72.2 (CH), 71.8 (CH₂), 71.6 (CH₂), 70.7 (CH₂), 70.7 (CH), 70.4 (CH), 70.0 (CH), 69.9 (CH), 68.1 (CH₂), 68.0 (CH₂), 67.1 (CH), 67.0 (CH), 66.9 (CH), 63.7 (CH), 59.7 (CH₂), 57.0 (CH₂), 51.7 (CH₃), 51.2 (CH₃), 50.1 (CH₂), 49.9 (CH₂), 47.0 (CH₂), 46.1 (CH₂), 28.8 (CH₂), 27.6 (CH₂), 27.1 (CH₂), 23.1 (CH₂), 23.1 (CH₂), 17.0 (CH₃); HRMS m/z (ESI, M-2H⁺ 3Na⁺) calcd for C₆₈H₇₅N₄O₂₅S₂BrNa₃⁺ 1559.3026, found 1559.3038.

Compound 43

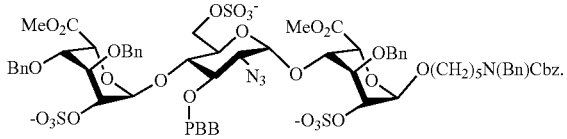

¹H NMR (600 MHz, CD₃OD) δ=7.48-7.40 (m, 9H, Ar—H), 7.29-7.23 (m, 15H, Ar—H), 7.14-7.11 (m, 3H, Ar—H), 7.03-7.00 (m, 2H, Ar—H), 5.43 (s, 1H, H-1″), 5.20-5.13 (m, 4H, H-1, H-1', ArCH₂), 4.87-4.82 (m, 4H, H-5″, ArCH₂), 4.76-4.74 (m, 1H, ArCH₂), 4.61-4.55 (m, 7H, H-2, H-2″, H-5, ArCH₂), 4.43 (d, J=11.8 Hz, 2H, ArCH₂), 4.34-4.27 (m, 5H, H-3, H-3″, H-4, H-6'), 4.11-4.04 (m, 2H, H-4', H-4″), 3.87-3.75 (m, 6H, H-3', H-5', CO₂Me, linker CH₂), 3.49-3.44 (m, 1H, linker CH₂), 3.31-3.30 (m, 1H, H-2'), 3.27-3.26 (m, 3H, CO₂Me), 3.20-3.15 (m, 2H, linker CH₂), 1.64-1.52 (m, 4H, linker CH₂), 1.31-1.25 (m, 2H, linker CH₂).

¹³C NMR (150 MHz, CD₃OD) δ=170.9 (C), 170.5 (C), 157.1 (C), 156.5 (C), 137.9 (C), 137.4 (C), 137.2 (C), 136.7 (C), 130.7 (CH), 129.3 (CH), 128.9 (CH), 128.6 (CH), 128.4 (CH), 128.2 (CH), 128.1 (CH), 128.1 (CH), 128.0 (CH), 128.0 (CH), 127.8 (CH), 127.7 (CH), 127.6 (CH), 127.4 (CH), 127.3 (CH), 127.0 (CH), 126.9 (CH), 120.6 (C), 99.5 (CH), 97.3 (CH), 95.9 (CH), 78.2 (CH), 73.6 (CH₂), 72.1 (CH), 71.8 (CH₂), 71.6 (CH₂), 71.4 (CH), 71.2 (CH), 71.1 (CH), 70.8 (CH₂), 70.5 (CH), 70.4 (CH), 69.7 (CH), 69.4 (CH), 68.0 (CH₂), 67.1 (CH), 67.0 (CH), 66.8 (CH), 65.8 (CH₂), 63.9 (CH), 56.9 (CH₂), 51.9 (CH₃), 51.4 (CH₃), 50.1 (CH₂), 49.9 (CH₂), 47.0 (CH₂), 46.1 (CH₂), 29.4 (CH₂), 28.8 (CH₂), 27.6 (CH₂), 27.1 (CH₂), 23.1 (CH₂); HRMS m/z (ESI, M-3H+Na²⁻) calcd for C₆₈H₇₄N₄O₂₈S₂BrNa²⁻ 796.1367, found 796.1370.

Compound 44

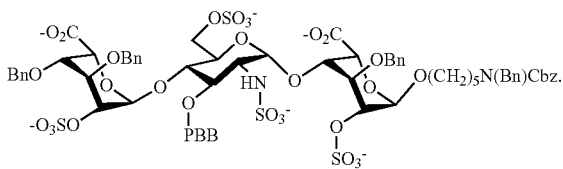

$^1$H NMR (600 MHz, CD$_3$OD) δ=7.41-7.39 (m, 2H, Ar—H), 7.34-7.32 (m, 2H, Ar—H), 7.27-7.17 (m, 25H, Ar—H), 5.83 (s, 1H, H-1"), 5.30-5.24 (m, 3H, H-1, H-1', ArCH$_2$), 5.06 (d, J=13.0 Hz, 2H, ArCH$_2$), 4.84-4.83 (m, 1H, H-5"), 4.73-4.68 (m, 2H, ArCH$_2$), 4.57-4.37 (m, 13H, H-2, H-2", H-3", H-5, H-6', ArCH$_2$), 4.07-3.99 (m, 6H, H-3', H-4, H-4', H-4", H-5', H-3), 3.63-3.56 (m, 2H, H-2', linker CH$_2$), 3.47-3.39 (m, 1H, linker CH$_2$), 3.14-3.08 (m, 2H, linker CH$_2$), 1.54-1.45 (m, 4H, linker CH$_2$), 1.27-1.23 (m, 2H, linker CH$_2$).

$^{13}$C NMR (150 MHz, CD$_3$OD) δ=177.5 (C), 174.0 (C), 157.1 (C), 156.6 (C), 139.0 (C), 138.0 (C), 137.9 (C), 137.7 (C), 137.6 (C), 136.7 (C), 136.6 (C), 130.5 (CH), 129.8 (CH), 128.8 (CH), 128.2 (CH), 128.0 (CH), 127.8 (CH), 127.7 (CH), 127.6 (CH), 127.5 (CH), 127.4 (CH), 127.2 (CH), 127.1 (CH), 126.9 (CH), 120.2 (C), 98.8 (CH), 95.1 (CH), 94.3 (CH), 76.1 (CH), 75.2 (CH), 74.6 (CH), 72.8 (CH$_2$), 72.7 (CH$_2$), 71.5 (CH$_2$), 70.8 (CH$_2$), 70.5 (CH), 70.1 (CH), 69.5 (CH), 68.1 (CH$_2$), 67.9 (CH$_2$), 67.0 (CH$_2$), 58.6527, 50.0 (CH$_2$), 49.8 (CH$_2$), 46.8 (CH$_2$), 46.1 (CH$_2$), 29.4 (CH$_2$), 28.8 (CH$_2$), 27.6 (CH$_2$), 27.0 (CH$_2$), 23.2 (CH$_2$); HRMS m/z (ESI, M-5H$^+$ 3Na$^{2-}$) calcd for C$_{66}$H$_{70}$N$_2$O$_{31}$S$_4$BrNa$_3{}^{2-}$ 831.0861, found 831.0869.

Compound 36

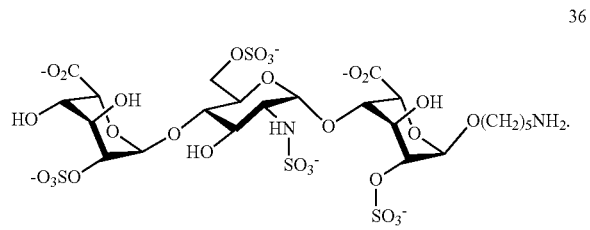

36

$^1$H NMR (600 MHz, D$_2$O) δ=5.43 (d, J=3.5 Hz, 1H, H-1'), 5.21 (s, 1H, H-1), 5.12 (d, J=2.9 Hz, 1H, H-1"), 4.87 (s, 1H, H-5), 4.52 (d, J=3 Hz, 1H, H-5"), 4.35-4.34 (m, 2H, H-2, H-6'a), 4.30-4.28 (m, 1H, H-6'b), 4.26-4.25 (m, 1H, H-2"), 4.23-4.22 (m, 1H, H-3"), 4.13-4.12 (m, 2H, H-3, H-4"), 4.09-4.08 (m, 1H, H-5'), 4.01 (s, 1H, H-4), 3.80-3.75 (m, 4H, H-3', H-4', linker CH$_2$), 3.29 (dd, J=3.4, 10.3 Hz, 1H, H-2'), 3.05-3.03 (m, 2H, linker CH$_2$), 1.73-1.69 (m, 4H, linker CH$_2$), 1.52-1.49 (m, 2H, linker CH$_2$).

$^{13}$C NMR (150 MHz, D$_2$O) δ=99.1 (CH), 99.0 (CH), 96.5 (CH), 76.9 (CH), 76.6 (CH), 75.8 (CH), 74.1 (CH), 69.6 (CH), 69.3 (CH), 69.1 (CH), 69.1 (CH), 69.0 (CH), 68.9 (CH), 68.0 (CH$_2$), 66.3 (CH$_2$), 57.9 (CH), 39.4 (CH$_2$), 27.8 (CH$_2$), 26.1 (CH$_2$), 22.2 (CH$_2$); HRMS m/z (ESI, M-2H$^{2-}$) calcd for C$_{23}$H$_{38}$N$_2$O$_{29}$S$_4{}^{2-}$ 467.0216, found 467.0247.

2.2 Compound 36 Inhibited Sulf-1 Activity

In this example, fluorogenic assay was carried out to assess the trisaccharide 36 (0.32 mM) as a competing substrate for Sulf-1. The data revealed that 36 has significant potential to reduce the hydrolysis of 4-MUS (4.35 mM) in the substrate mixture (FIG. 2, (A)). The EC$_{50}$ value of 36 measured by ELISA was 3.8 μM, indicating that 36 possessed a relatively higher affinity toward Sulf-1 as compared to that of 19.

An HPLC-based assay for the measurement of sulfate ions after digestion of HS with Sulf-1 in vitro was also developed. To directly calculate the contribution of sulfate release, compound 36 (480 μM) was treated with human Sulf-1 and the amount of the sulfate analyte was compared with that of untreated 36 as a control (FIG. 2, (B)). The sulfate concentration (381.1 μM) was determined by HPLC using the strong AS9-HC anion exchange column and a conductivity detector. Based on this assay, the sulfate concentrations upon the hydrolysis of disaccharide 18 and tetrasaccharide 19 were determined as 5.9 μM and 46.2 μM, respectively. Moreover, 480 μM of 36 was treated with varying amounts of Sulf-1 (1, 2, and 5 μL) for 16 h, and 49.9, 93.5, and 155.8 μM SO$_4{}^{2-}$ were obtained, respectively. As observed, 2 μL of Sulf-1 could hydrolyze the 6-O-sulfate group of 36 (FIG. 2, (C)) to a notable extent. The kinetic character of the specific 6-desulfation phenomenon was further evaluated by treating 480 μM of 36 with 2 μL of Sulf-1 at different time points. Here, the Sulf-1 activity reached a maximum at 2 h (FIG. 2, (D)). The amounts of released sulfate ions at different substrate concentrations were analyzed, and the kinetic parameters V$_{max}$ and K$_m$ (FIG. 2, (E)) were determined as 14.1 M/h and 25.8 μM, respectively. These data indicate that compound 36 has markedly higher activity compared with the artificial substrate 4-MUS (K$_m$ value was measured as 10 mM). These findings also suggest that binding of the HS substrate blocks the entry of 4-MUS to the enzyme active site and emphasize that the trisaccharide 36 is an excellent substrate for human Sulf-1.

Example 3 Design and Synthesis of Sulf-1's Inhibitors and their Inhibitory Activity 3.1 Design and Synthesis of Sulf-1's Inhibitor Based on results from Examples 1 and 2, the di-, tri-, and tetrasaccharide analogues 45-47 were rationally designed and synthesized in accordance with steps described in Schemes 4 and 5.

In Scheme 4, treatment of the 6'-alcohol 42 with ClSO$_2$NHBn in pyridine afforded compound 48 (95%), which underwent a 3-step conversion (ester demethylation, Staudinger reduction, and N-sulfation) to give the desired N-sulfate 49 in 32% overall yield. Hydrogenolysis of compound 49 led to the target compound 46, which was isolated in 43% yield after purification through Sephadex G25 and ion-exchange with Dowex 50WX8-Na$^+$ resin.

Scheme 4. Preparation of the trisaccharide sulfonamide 46

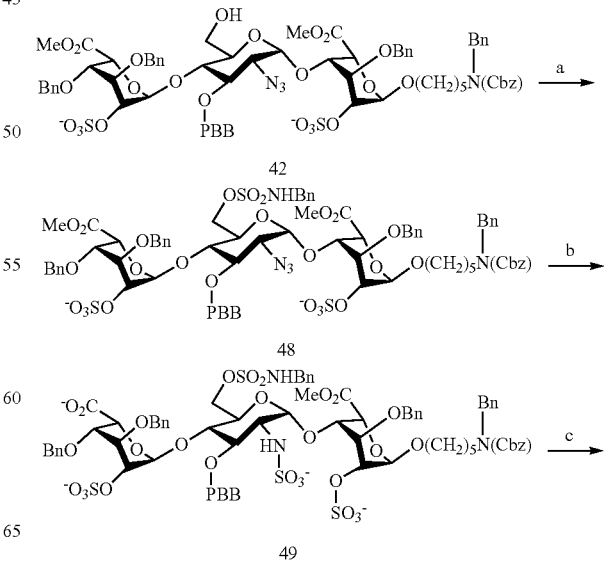

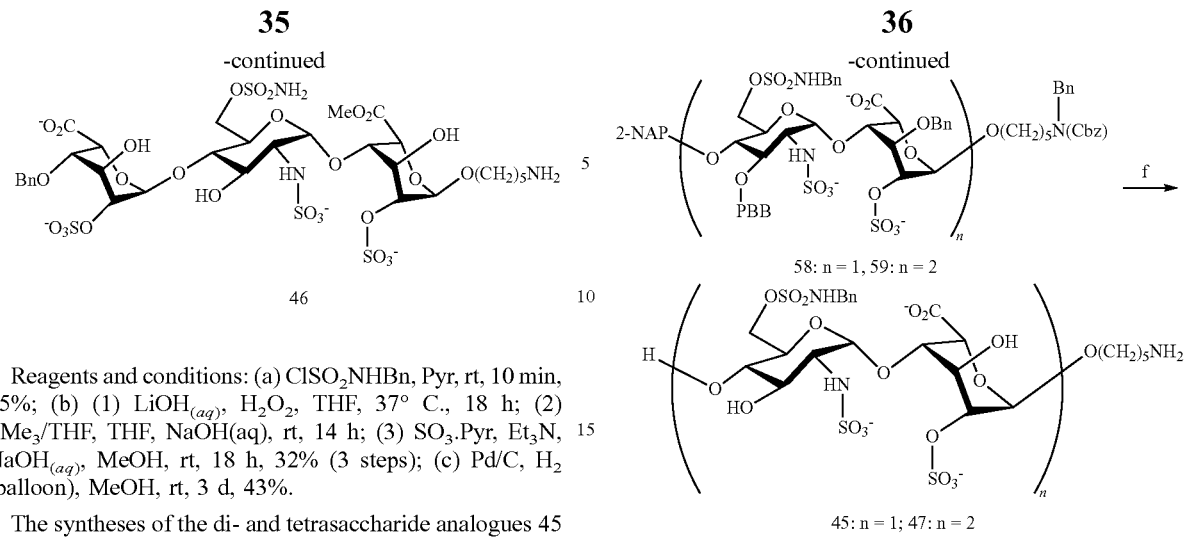

Reagents and conditions: (a) MeOH, Et$_3$N, CH$_2$Cl$_2$, 40 C, 18 h, 50: 83%, 51: 97%; (b) SO$_3$.Et$_3$N, DMF, 60 C, 18 h, 52: 75%, 53: 68%; (c) HF.Pyr, Pyr, THF, 72 h, 54: 60%, 55: 76%; (d) ClSO$_2$NHBn, Pyr, rt, 10 min, 56: 61%, 57: 87%; (e) (1) LiOH(aq), H$_2$O$_2$, THF, 37° C., 18 h; (2) PMe$_3$/THF, THF, NaOH(aq), rt, 14 h; (3) SO$_3$.Pyr, Et$_3$N, NaOH(aq), MeOH, rt, 18 h, 58: 56% (3 steps), 59: 39% (3 steps); (f) Pd/C, H$_2$ (balloon), MeOH, rt, 3 d, 45: 29%, 47: 22%.

Compound 48

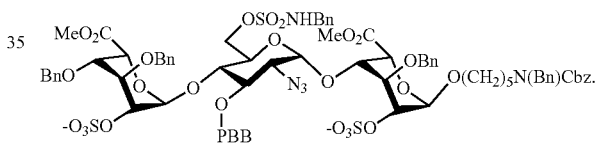

$^1$H NMR (600 MHz, CD$_3$OD) δ=7.39-7.38 (m, 2H, Ar—H), 7.36-7.35 (m, 1H, Ar—H), 7.35-7.34 (m, 4H, Ar—H), 7.32-7.31 (m, 5H, Ar—H), 7.30-7.29 (m, 2H, Ar—H), 7.25-7.24 (m, 3H, Ar—H), 7.21-7.20 (m, 4H, Ar—H), 7.19-7.17 (m, 6H, Ar—H), 7.15-7.14 (m, 1H, Ar—H), 7.13-7.12 (m, 2H, Ar—H), 7.10-7.09 (m, 2H, Ar—H), 7.01-6.98 (m, 2H, Ar—H), 5.22 (s, 1H, H-1″), 5.10-5.06 (m, 4H, H-1, H-1′, ArCH$_2$), 4.75-4.73 (m, 3H, H-5″, ArCH$_2$), 4.63 (d, J=2.4 Hz, 1H, H-5), 4.58-4.51 (m, 6H, H-2″, ArCH$_2$), 4.42 (s, 1H, H-2), 4.38-4.36 (m, 3H, H-3″, H-6′b, ArCH$_2$), 4.28-4.22 (m, 6H, H-6′a, H-3, ArCH$_2$), 4.13-4.11 (m, 1H, H-4″), 4.00 (m, 3H, CO$_2$Me), 3.84-3.82 (m, 1H, H-5′), 3.76-3.73 (m, 4H, H-4′, CO$_2$Me), 3.66-3.59 (m, 3H, H-3′, H-4, linker CH$_2$), 3.45-3.37 (m, 1H, linker CH$_2$), 3.22-3.21 (m, 1H, H-2′), 3.14-3.09 (m, 2H, linker CH$_2$), 1.57-1.46 (m, 4H, linker CH$_2$), 1.30-1.11 (m, 2H, linker CH$_2$).

$^{13}$C NMR (150 MHz, CD$_3$OD) δ=170.2 (C), 170.1 (C), 157.0 (C), 156.5 (C), 137.9 (C), 137.7 (C), 137.6 (C), 137.3 (C), 137.2 (C), 136.7 (C), 133.1 (C), 130.7 (CH), 129.1 (CH), 128.7 (CH), 128.4 (CH), 128.3 (CH), 128.2 (CH), 128.2 (CH), 128.0 (CH), 127.9 (CH), 127.9 (CH), 127.8 (CH), 127.8 (CH), 127.5 (CH), 127.5 (CH), 127.2 (CH), 127.0 (CH), 126.9 (CH), 120.5 (CH), 99.5 (CH), 98.6 (CH), 95.3 (CH), 78.1 (CH), 73.5 (CH), 73.3 (CH$_2$), 72.5 (CH), 71.8 (CH$_2$), 71.6 (CH$_2$), 71.3 (CH), 71.1 (CH), 71.0 (CH), 70.8 (CH$_2$), 70.7 (CH), 70.4 (CH), 70.1 (CH), 67.9 (CH$_2$),

Reagents and conditions: (a) ClSO$_2$NHBn, Pyr, rt, 10 min, 95%; (b) (1) LiOH(aq), H$_2$O$_2$, THF, 37° C., 18 h; (2) PMe$_3$/THF, THF, NaOH(aq), rt, 14 h; (3) SO$_3$.Pyr, Et$_3$N, NaOH(aq), MeOH, rt, 18 h, 32% (3 steps); (c) Pd/C, H$_2$ (balloon), MeOH, rt, 3 d, 43%.

The syntheses of the di- and tetrasaccharide analogues 45 and 47 are outlined in Scheme 5. Ring opening of the lactones 12 and 13 under basic conditions in MeOH and Et$_3$N yielded the methyl esters 50 (83%) and 51 (97%), respectively. O-Sulfation of compounds 50 and 51 individually provided the corresponding O-sulfates 52 (75%) and 53 (68%), which were subjected to desilylation, affording the alcohols 54 and 55 in 60% and 76% yields, respectively. Sulfamoylation of compounds 54 and 55 at the primary hydroxy groups resulted in the successful formation of the benzyl sulfamates 56 (61%) and 57 (87%), which underwent a similar 3-step transformation as 48→49 to furnish the N-sulfated derivatives 58 and 59 in 56% and 39% overall yields, respectively. Finally, hydrogenolysis to remove all Bn, Cbz, 2-NAP, and PBB groups concomitantly gave the expected target products 45 (29%) and 47 (22%).

Scheme 5. Synthesis of the di- and tetrasaccharide analogs 45 and 47

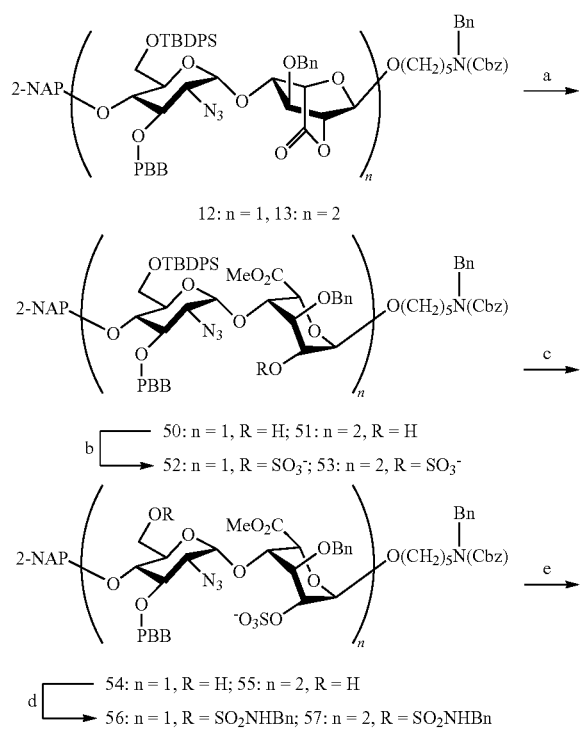

67.8 (CH), 67.7 (CH$_2$), 67.1 (CH), 67.0 (CH$_2$), 66.9 (CH$_2$), 63.3 (CH), 51.7 (CH$_3$), 50.9 (CH$_3$), 50.1 (CH$_2$), 49.9 (CH$_2$), 48.1 (CH), 47.0 (CH$_2$), 46.7 (CH$_2$), 46.1 (CH$_2$), 43.1 (CH$_2$), 29.2 (CH$_3$), 28.7 (CH$_2$), 27.5 (CH$_2$), 27.1 (CH$_2$), 23.0 (CH$_2$); HRMS m/z (ESI, M-2H$^{2-}$) calcd for C$_{75}$H$_{84}$N$_5$O$_{27}$S$_3$Br$^{2-}$ 829.6771, found 829.6764.

Compound 49

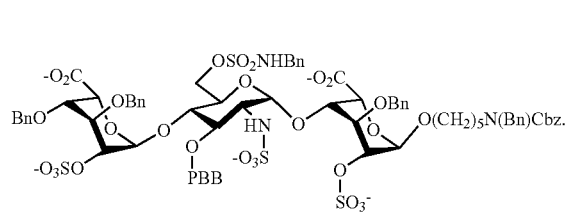

49

$^1$H NMR (600 MHz, CD$_3$OD) δ=7.45-7.42 (m, 2H, Ar—H), 7.37-7.35 (m, 2H, Ar—H), 7.30-7.27 (m, 5H, Ar—H), 7.23-7.18 (m, 17H, Ar—H), 7.11-7.08 (m, 8H, Ar—H), 5.74 (s, 1H, H-1"), 5.30-5.25 (m, 3H, H-1, H-1', ArCH$_2$), 5.10-5.07 (m, 2H, ArCH$_2$), 4.85-4.84 (m, 1H, ArCH$_2$), 4.75-4.74 (m, 1H, H-5"), 4.66-4.60 (m, 5H, H-2", H-5, ArCH$_2$), 4.43-4.39 (m, 6H, H-2, ArCH$_2$), 4.25-4.21 (m, 2H, H-6'a, H-6'b), 4.15-4.09 (m, 6H, H-3', H-3", H-4', H-5', ArCH$_2$), 3.99 (s, 1H, H-4), 3.94 (s, 1H, H-4"), 3.85 (t, J=10.3 Hz, 1H, H-3), 3.58-3.53 (m, 2H, H-2', linker CH$_2$), 3.45-3.39 (m, 1H, linker CH$_2$), 3.16-3.09 (m, 2H, linker CH$_2$), 1.58-1.47 (m, 4H, linker CH$_2$), 1.31-1.21 (m, 2H, linker CH$_2$).

$^{13}$C NMR (150 MHz, CD$_3$OD) δ=175.9 (C), 174.6 (C), 157.0 (C), 156.5 (C), 139.0 (C), 138.2 (C), 137.8 (C), 137.69 (C), 137.61 (C), 130.5 (CH), 130.0 (CH), 128.5 (CH), 128.1 (CH), 128.0 (CH), 127.9 (CH), 127.9 (CH), 127.7 (CH), 127.5 (CH), 127.4 (CH), 127.3 (CH), 127.2 (CH), 127.1 (CH), 127.0 (CH), 126.9 (CH), 126.9 (CH), 120.2 (C), 98.7 (CH), 96.3 (CH), 93.6 (CH), 75.3 (CH), 74.7 (CH), 73.3 (CH), 72.9 (CH$_2$), 72.4 (CH$_2$), 71.3 (CH), 71.3 (CH$_2$), 71.0 (CH), 70.7 (CH$_2$), 70.3 (CH), 70.0 (CH), 68.7 (CH), 68.0 (CH$_2$), 67.2 (CH), 67.0 (CH$_2$), 66.5 (CH), 59.1 (CH$_2$), 50.0 (CH$_2$), 49.8 (CH$_2$), 28.9 (CH$_2$), 27.6 (CH$_2$), 27.1 (CH$_2$), 23.2 (CH$_2$); HRMS m/z (ESI, M-5H$^+$ 2Na$^{3-}$) calcd for C$_{73}$H$_{77}$N$_3$O$_{30}$S$_4$BrNa$_2{}^{3-}$ 576.0818, found 576.0826.

Compound 46

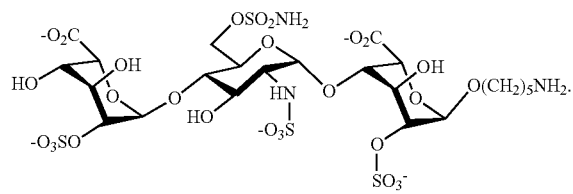

46

$^1$H NMR (600 MHz, D$_2$O) δ=5.40 (d, J=3.5 Hz, 1H, H-1'), 5.25-5.18 (m, 2H, H-1, H-1"), 4.88-4.86 (m, 1H, H-5), 4.56-4.49 (m, 3H, H-5", H-6'), 4.34 (d, J=2.4 Hz, 1H, H-2), 4.28-4.25 (m, 2H, H-2", H-3"), 4.17-4.08 (m, 4H, H-3, H-4, H-4", H-5'), 3.81-3.77 (m, 3H, H-3', H-4', linker CH$_2$), 3.71-3.65 (m, 1H, linker CH$_2$), 3.29 (dd, 1H, J=3.1, 9.5 Hz, H-2'), 3.08-3.03 (m, 2H, linker CH$_2$), 1.75-1.68 (m, 4H, linker CH$_2$), 1.53-1.48 (m, 2H, linker CH$_2$).

$^{13}$C NMR (150 MHz, D$_2$O) δ=176.2 (C), 174.7 (C), 99.3 (CH), 98.8 (CH), 97.1 (CH), 77.4 (CH), 76.3 (CH), 76.0 (CH), 74.0 (CH), 69.5 (CH), 68.9 (CH), 68.8 (CH), 68.7 (CH), 68.6 (CH), 68.3 (CH$_2$), 68.0 (CH$_2$), 67.9 (CH), 58.0 (CH), 49.0 (CH), 46.6 (CH), 39.4 (CH$_2$), 27.7 (CH$_2$), 26.1 (CH$_2$), 24.8 (CH$_2$), 22.1 (CH$_2$); HRMS m/z (ESI, M-4H$^+$ 5Na$^+$) calcd for C$_{23}$H$_{37}$N$_3$O$_{28}$S$_4$Na$_5{}^+$ 1045.9935, found 1045.9938.

Compound 46-1

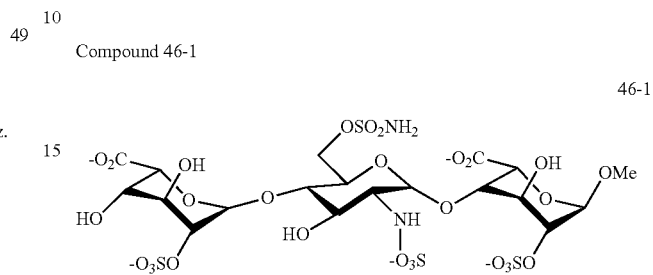

46-1

$^1$H NMR (600 MHz, D$_2$O) δ=5.33 (d, J=3.4, 1H, H-1'), 5.14 (s, 1H, H-1"), 5.03 (s, 1H, H-1), 4.89-4.87 (m, 1H, H-5), 4.48-4.43 (m, 3H, H-5", H-6'), 4.30-4.21 (m, 3H, H-2, H-2", H-3"), 4.10-3.97 (m, 4H, H-3, H-4, H-4", H-5'), 3.75-3.70 (m, 2H, H-3', H-4'), 3.40 (s, 3H, OCH$_3$), 3.25 (dd, 1H, J=3.3, 12.2 Hz, H-2').

$^{13}$C NMR (150 MHz, D$_2$O) δ=176.3 (C), 175.0 (C), 99.5 (CH), 99.4 (CH), 97.5 (CH), 77.6 (CH), 76.1 (CH), 74.5 (CH), 73.9 (CH), 69.4 (CH), 68.9 (CH), 68.8 (CH), 68.7 (CH), 68.6 (CH), 68.3 (CH$_2$), 67.5 (CH), 67.3 (CH), 58.1 (CH), 55.4 (OCH$_3$)

HRMS m/z (ESI, M-6H$^+$ 5Na$^+$) calcd for C$_{19}$H$_{26}$N$_2$O$_{28}$S$_4$Na$_5{}^-$ 972.9049, found 972.9021.

Compound 50

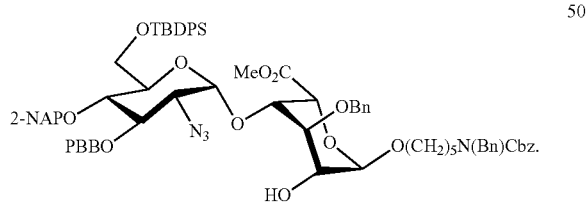

50

$^1$H NMR (600 MHz, CD$_3$OD) δ=7.76-7.75 (m, 1H, Ar—H), 7.66-7.64 (m, 2H, Ar—H), 7.59 (d, J=6.9 Hz, 2H, Ar—H), 7.54 (d, J=7.2 Hz, 2H, Ar—H), 7.5 (s, 1H, Ar—H), 7.42-7.40 (m, 2H, Ar—H), 7.34-7.33 (m, 2H, Ar—H), 7.30-7.21 (m, 23H, Ar—H), 7.06 (s, 1H, Ar—H), 5.13 (d, J=3.4 Hz, 1H, H-1'), 5.04 (d, J=18.3 Hz, 2H, ArCH$_2$), 4.89-4.86 (m, 2H, H-1, ArCH$_2$), 4.76-4.71 (m, 6H, ArCH$_2$), 4.59 (d, J=11.1 Hz, 1H, ArCH$_2$), 4.37 (s, 2H, H-2, H-5), 4.04 (m, 1H, H-3), 3.88 (t, J=5.1 Hz, 1H, H-4), 3.82-3.78 (m, 3H, H-3', H-6'), 3.65-3.60 (m, 6H, H-4', H-5' OCH$_3$, linker CH$_2$), 3.45-3.38 (m, 2H, H-2', linker CH$_2$), 3.15-3.11 (m, 2H, linker CH$_2$), 1.54-1.45 (m, 4H, linker CH$_2$), 1.27-1.22 (m, 2H, linker CH$_2$), 0.95 (s, 9H, TBDPS).

$^{13}$C NMR (150 MHz, CD$_3$OD) δ=171.7 (C), 139.8 (C), 138.8 (C), 137.1 (CH), 136.9 (CH), 134.8 (C), 134.7 (C), 134.6 (C), 134.5 (C), 132.6 (C), 131.0 (CH), 129.7 (CH), 129.5 (CH), 129.4 (CH), 129.1 (CH), 129.0 (CH), 128.9 (CH), 128.5 (CH), 127.4 (CH), 127.2 (CH), 126.8 (CH), 122.7 (C), 102.9 (CH), 97.8 (CH), 81.8 (CH), 79.6 (CH), 79.5 (CH), 77.0 (CH), 76.2 (CH$_2$), 75.5 (CH$_2$), 74.3 (CH$_2$), 74.2 (CH), 74.0 (CH$_2$), 70.8 (CH), 70.7 (CH$_2$), 69.9 (CH), 68.5 (CH), 65.2 (CH), 64.2 (CH$_2$), 52.9 (CH), 27.6 (CH$_3$), 20.3 (C); HRMS m/z (ESI, M+Na$^+$) calcd for C$_{74}$H$_{81}$N$_4$O$_{13}$SiBrNa$^+$ 1363.4650, found 1363.4653.

Compound 52

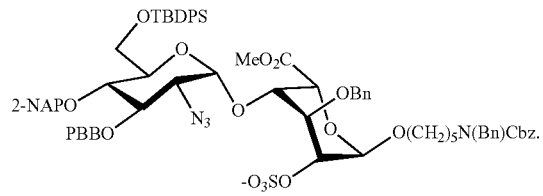

52

$^1$H NMR (600 MHz, CD$_3$OD) δ=7.72-7.71 (m, 1H, Ar—H), 7.63-7.61 (m, 4H, Ar—H), 7.54 (d, J=7.6 Hz, 2H, Ar—H), 7.48 (s, 1H, Ar—H), 7.37-7.35 (m, 2H, Ar—H), 7.29-7.28 (m, 2H, Ar—H), 7.24-7.16 (m, 23H, Ar—H), 7.04-7.02 (m, 1H, Ar—H), 5.17 (d, J=3.0 Hz, 1H, H-1'), 5.09 (s, 1H, H-1), 5.01 (d, J=25.5 Hz, 2H, ArCH$_2$), 4.84-4.81 (m, 2H, ArCH$_2$), 4.75-4.72 (m, 4H, H-5, ArCH$_2$), 4.51-4.48 (m, 2H, H-2, ArCH$_2$), 4.34-4.31 (m, 3H, H-3, ArCH$_2$), 4.11 (s, 1H, H-4), 3.92-3.90 (m, 1H, H-5'), 3.86-3.82 (m, 2H, H-6'), 3.71-3.69 (m, 2H, H-3', H-4'), 3.62-3.55 (m, 4H, linker, CO$_2$Me), 3.41-3.36 (m, 1H, linker CH$_2$), 3.25-3.24 (m, 1H, H-2'), 3.08-3.05 (m, 2H, linker CH$_2$), 1.51-1.40 (m, 4H, linker CH$_2$), 1.24-1.20 (m, 1H, linker CH$_2$), 1.13-1.10 (m, 1H, linker CH$_2$), 0.96 (s, 9H, TBDPS).

$^{13}$C NMR (150 MHz, CD$_3$OD) δ=171.7 (C), 158.5 (C), 157.9 (C), 139.5 (C), 139.1 (C), 138.2 (C), 137.2 (C), 137.1 (CH), 136.8 (CH), 134.79 (C), 134.72 (C), 134.5 (C), 134.4 (C), 132.5 (CH), 131.08 (CH), 131.05 (CH), 131.0 (CH), 129.7 (CH), 129.6 (CH), 129.3 (CH), 129.2 (CH), 129.1 (CH), 129.0 (CH), 128.9 (CH), 128.7 (CH), 128.5 (CH), 128.4 (CH), 127.3 (CH), 127.2 (CH), 127.1 (CH), 126.7 (CH), 122.5 (C), 100.9 (CH), 97.5 (CH), 81.4 (CH), 79.6 (CH), 79.5 (CH), 76.0 (CH$_2$), 75.3 (CH$_2$), 74.1 (CH), 73.19 (CH$_2$), 73.12 (CH$_2$), 72.5 (CH), 72.4 (CH), 69.5 (CH$_2$), 69.4 (CH$_2$), 68.7 (CH), 68.5 (CH$_2$), 68.4 (CH$_2$), 65.2 (CH), 64.1 (CH$_2$), 52.9 (CH), 51.6 (CH$_2$), 51.4 (CH$_2$), 48.5 (CH$_2$), 48.0 (CH$_2$), 47.6 (CH), 30.3 (CH$_2$), 29.0 (CH$_2$), 28.6 (CH$_2$), 27.6 (CH$_3$), 24.6 (CH), 24.6 (CH), 20.2 (C), 9.4 (CH$_3$); HRMS m/z (ESI, M–H$^-$) calcd for C$_{74}$H$_{80}$N$_4$O$_{16}$SiSBr$^-$ 1419.4243, found 1419.4247.

Compound 54

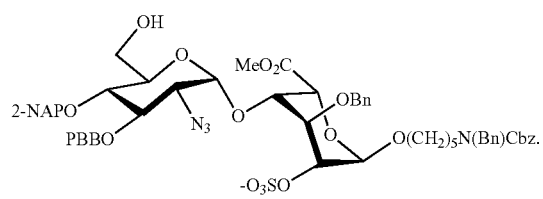

54

$^1$H NMR (600 MHz, CD$_3$OD) δ=7.78-7.73 (m, 3H, Ar—H), 7.62 (m, 1H, Ar—H), 7.40-7.23 (m, 22H, Ar—H), 5.12-5.06 (m, 4H, H-1, H-1', ArCH$_2$), 4.83-4.81 (m, 2H, ArCH$_2$), 4.77-4.72 (m, 4H, H-5, ArCH$_2$), 4.54 (d, J=11.4 Hz, 1H, ArCH$_2$), 4.44 (s, 1H, H-2), 4.47-4.44 (m, 1H, ArCH$_2$), 4.26 (s, 2H, ArCH$_2$), 4.08 (s, 1H, H-3), 3.92 (s, 1H, H-4), 3.95-3.92 (m, 1H, H-3'), 3.75-3.70 (m, 6H, H-5', H-6', CO$_2$Me), 3.64-3.59 (m, 2H, H-4', linker CH$_2$), 3.44-3.38 (m, 1H, linker CH$_2$), 3.26-3.25 (m, 1H, H-2'), 3.15-3.10 (m, 2H, linker CH$_2$), 1.60-1.47 (m, 4H, linker CH$_2$), 1.29-1.23 (m, 2H, linker CH$_2$).

$^{13}$C NMR (150 MHz, CD$_3$OD) δ=171.8 (C), 158.4 (C), 157.9 (C), 139.5 (C), 139.2 (C), 138.1 (C), 137.4 (C), 134.8 (C), 134.4 (C), 132.3 (CH), 130.8 (CH), 129.6 (CH), 129.5 (CH), 129.3 (CH), 129.1 (CH), 129.0 (CH), 128.7 (CH), 128.4 (CH), 128.3 (CH), 127.2 (C), 127.23 (C), 127.0 (C), 126.8 (C), 122.3 (C), 101.0 (CH), 98.2 (CH), 81.1 (CH), 79.2 (CH), 75.7 (CH$_2$), 75.2 (CH$_2$), 73.9 (CH), 73.7 (CH), 73.1 (CH), 73.0 (CH$_2$), 72.6 (CH), 69.4 (CH$_2$), 69.3 (CH$_2$), 68.5 (CH), 68.4 (CH$_2$), 68.3 (CH$_2$), 65.0 (CH), 61.6 (CH$_2$), 52.9 (CH), 51.5 (CH$_2$), 51.3 (CH$_2$), 48.4 (CH), 48.0 (CH$_2$), 47.6 (CH), 30.2 (CH$_3$), 29.0 (CH$_2$), 28.5 (CH$_2$), 24.6 (CH$_2$), 24.5 (CH$_2$), 9.3 (CH$_3$); HRMS m/z (ESI, M–H$^+$ 2Na$^+$) calcd for C$_{58}$H$_{62}$N$_4$O$_{16}$Na$_2$SBr$^+$ 1227.2860, found 1227.2854.

Compound 56

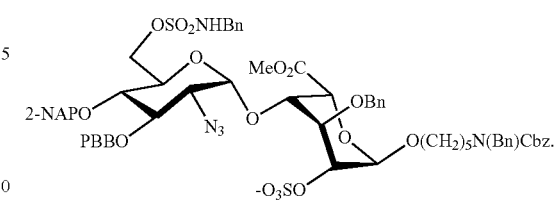

56

$^1$H NMR (600 MHz, CD$_3$OD) δ=7.75-7.72 (m, 3H, Ar—H), 7.62 (s, 1H, Ar—H), 7.39-7.37 (m, 2H, Ar—H), 7.33-7.18 (m, 25H, Ar—H), 5.11-5.05 (m, 4H, H-1', H-1, ArCH$_2$), 4.82-4.80 (m, 2H, ArCH$_2$), 4.75-4.71 (m, 4H, H-5, ArCH$_2$), 4.52 (d, J=11.4 Hz, 1H, ArCH$_2$), 4.43 (s, 1H, H-2), 4.40-4.36 (m, 2H, ArCH$_2$), 4.26-4.22 (m, 3H, H-3, H-6'), 4.13-4.08 (m, 3H, H-4, ArCH$_2$), 3.99-3.94 (m, 2H, H-3', H-5'), 3.66 (s, 3H, OCH$_3$), 3.64-3.58 (m, 1H, linker CH$_2$), 3.46 (t, J=9.4 Hz, 1H, H-4'), 3.43-3.37 (m, 1H, linker CH$_2$), 3.26-3.25 (m, 1H, H-2'), 3.14-3.08 (m, 2H, linker CH$_2$), 1.60-1.46 (m, 4H, linker CH$_2$), 1.29-1.18 (m, 2H, linker CH$_2$).

$^{13}$C NMR (150 MHz, CD$_3$OD) δ=171.9 (C), 158.5 (C), 158.0 (C), 139.4 (C), 139.1 (C), 138.6 (C), 138.1 (C), 137.1 (C), 134.8 (C), 134.5 (C), 132.4 (CH), 130.9 (CH), 129.6 (CH), 129.5 (CH), 129.3 (CH), 129.2 (CH), 129.16 (CH), 129.12 (CH), 129.07 (CH), 129.00 (CH), 128.79 (CH), 128.76 (CH), 128.49 (CH), 128.40 (CH), 127.3 (CH), 127.2 (CH), 127.0 (CH), 126.8 (CH), 122.3 (C), 101.1 (CH), 98.8 (CH), 81.1 (CH), 79.5 (CH), 79.0 (CH), 75.7 (CH$_2$), 75.3 (CH$_2$), 74.3 (CH), 74.1 (CH), 73.0 (CH$_2$), 72.2 (CH), 72.2 (CH), 71.4 (CH), 69.4 (CH$_2$), 69.3 (CH$_2$), 69.2 (CH$_2$), 68.5 (CH$_2$), 68.3 (CH$_2$), 68.3 (CH), 65.0 (CH), 53.7 (CH), 53.1 (CH$_3$), 51.5 (CH$_2$), 51.3 (CH$_2$), 49.6 (CH$_2$), 48.4 (CH$_2$), 48.2 (CH$_2$), 47.9 (CH$_2$), 47.7 (CH$_2$), 47.6 (CH$_2$), 30.3 (CH$_2$), 30.2 (CH$_2$), 29.0 (CH$_2$), 28.5 (CH$_2$), 24.6 (CH$_2$), 24.5 (CH$_2$); HRMS m/z (ESI, M–H$^-$) calcd for C$_{65}$H$_{69}$N$_5$O$_{18}$S$_2$Br$^-$ 1350.3262, found 1350.3259.

Compound 58

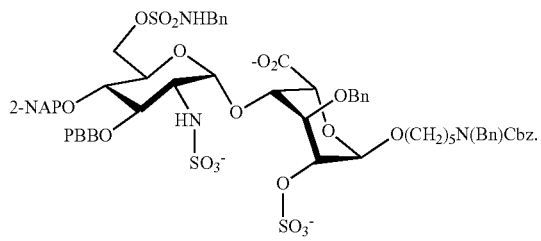

¹H NMR (600 MHz, CD₃OD) δ=7.78-7.71 (m, 3H, Ar—H), 7.57 (s, 1H, Ar—H), 7.40-7.37 (m, 2H, Ar—H), 7.31-7.17 (m, 25H, Ar—H), 5.32 (d, J=3.5 Hz, 1H, H-1'), 5.19 (s, 1H, H-1), 5.11-5.05 (m, 3H, ArCH₂), 4.82-4.81 (m, 1H, ArCH₂), 4.72-4.69 (m, 2H, ArCH₂), 4.63-4.61 (m, 2H, ArCH₂), 4.57-4.54 (m, 1H, H-5), 4.47-4.43 (m, 2H, H-2, H-6'a), 4.39-4.36 (m, 3H, H-6'b, ArCH₂), 4.27 (s, 1H, H-3), 4.20-4.14 (m, 1H, H-4, ArCH₂), 4.05 (d, J=10.1 Hz, 1H, H-5'), 3.73 (t, J=9.6 Hz, 1H, H-3'), 3.62-3.55 (m, 3H, H-2', H-4', linker CH₂), 3.42-3.35 (m, 1H, linker CH₂), 3.12-3.05 (m, 2H, linker CH₂), 1.59-1.44 (m, 4H, linker CH₂), 1.27-1.17 (m, 2H, linker CH₂).

¹³C NMR (150 MHz, CD₃OD) δ=174.1 (C), 157.1 (C), 156.5 (C), 138.8 (C), 138.5 (C), 138.0 (C), 137.8 (C), 137.3 (C), 135.9 (C), 133.3 (C), 133.0 (C), 130.8 (CH), 129.8 (CH), 128.2 (CH), 128.1 (CH), 127.7 (CH), 127.6 (CH), 127.5 (CH), 127.28 (CH), 127.21 (CH), 127.1 (CH), 127.0 (CH), 126.9 (CH), 126.3 (CH), 125.8 (CH), 125.6 (CH), 125.5 (CH), 120.5 (C), 98.9 (CH), 98.8 (CH), 80.3 (CH), 77.3 (CH), 74.8 (CH), 74.6 (CH₂), 74.1 (CH), 71.4 (CH₂), 70.6 (CH), 69.0 (CH), 67.9 (CH₂), 67.5 (CH₂), 67.0 (CH), 66.9 (CH), 58.9 (CH), 50.1 (CH₂), 49.9 (CH₂), 46.8 (CH₂), 46.2 (CH₂), 28.9 (CH₂), 27.6 (CH₂), 23.2 (CH₂). HRMS m/z (ESI, M-3H⁺ 4Na⁺) calcd for $C_{164}H_{67}N_3O_{21}Na_4S_3Br^+$ 1480.2203, found 1480.2207.

Compound 45

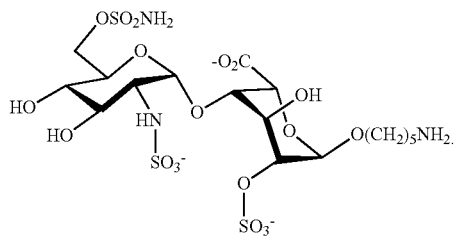

¹H NMR (600 MHz, D₂O) δ=5.38 (d, J=2.9 Hz, 1H, H-1'), 5.16 (s, 1H, H-1), 4.55-4.51 (m, 2H, H-5, H-6'a), 4.44-4.39 (m, 1H, H-6'b), 4.26 (s, 2H, H-2, H-3), 4.10-4.06 (m, 2H, H-4, H-5'), 3.83-3.79 (m, 1H, linker CH₂), 3.72-3.68 (m, 2H, H-3', linker CH₂), 3.56 (t, J=9.4 Hz, 1H, H-4'), 3.26 (dd, J=3.2, 10.3 Hz, 1H, H-2'), 3.07-3.03 (m, 2H, linker CH₂), 1.77-1.70 (m, 4H, linker CH₂), 1.53-1.48 (m, 2H, linker CH₂).

¹³C NMR (150 MHz, D₂O) δ=174.9 (C), 98.6 (CH), 97.3 (CH), 76.1 (CH), 75.6 (CH), 70.9 (CH), 69.6 (CH), 69.2 (CH), 68.3 (CH), 68.2 (CH₂), 68.1 (CH), 68.08 (CH₂), 68.00 (CH), 57.9 (CH), 49.0 (CH₂), 39.4 (CH₂), 32.6 (CH), 27.7 (CH₂), 26.2 (CH₂), 24.9 (CH₂), 22.2 (CH₂); HRMS m/z (ESI, M-2H²⁻) calcd for $C_{17}H_{33}N_3O_{19}S_3^{2-}$ 338.5357, found 338.5359.

Compound 51

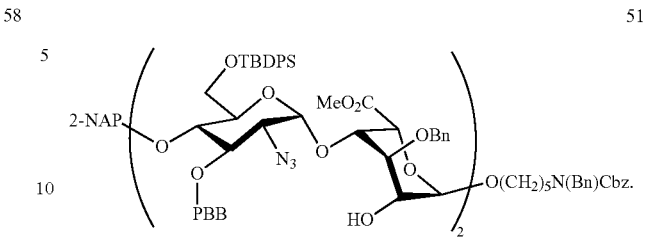

¹H NMR (600 MHz, CDCl₃) δ=7.87-7.81 (m, 9H, Ar—H), 7.70 (d, J=7.2 Hz, 2H, Ar—H), 7.64 (s, 1H, Ar—H), 7.54-7.52 (m, 2H, Ar—H), 7.46-7.37 (m, 36H, Ar—H), 7.25-7.24 (m, 1H, Ar—H), 7.19-7.18 (m, 2H, Ar—H), 7.10-7.08 (m, 2H, Ar—H), 5.42 (s, 1H, H-1"), 5.21 (d, J=15.9 Hz, 2H, ArCH₂), 5.10-5.01 (m, 5H, H-1, H-1', H-1'", ArCH₂), 4.88-4.69 (m, 12H, H-2, H-2", H-3", H-5, H-5", ArCH₂), 4.17-4.13 (m, 2H, H-3, H-4'), 4.04-3.93 (m, 10H, H-4, H-5'", H-6', H-6'", linker CH₂, ArCH₂), 4.78-4.73 (m, 3H, H-3'", H-4'", H-5'), 3.60-3.57 (m, 7H, H-2', H-2'", H-3', linker CH₂, CO₂Me), 3.46-3.44 (m, 1H, H-4'), 3.32 (s, 3H, CO₂Me), 3.29-3.24 (m, 2H, linker CH₂), 1.67-1.59 (m, 4H, linker CH₂), 1.39-1.33 (m, 2H, linker CH₂), 1.18-1.14 (m 18H, TBDPS).

¹³C NMR (150 MHz, CDCl₃) δ=169.9 (C), 169.0 (C), 156.7 (C), 156.2 (C), 137.6 (C), 137.2 (C), 136.8 (C), 136.7 (C), 136.05 (CH), 136.00 (CH), 135.9 (C), 135.67 (C), 135.63 (CH), 133.4 (C), 133.39 (C), 133.30 (C), 133.1 (C), 133.0 (C), 131.6 (CH), 131.2 (CH), 129.89 (CH), 129.86 (CH), 129.7 (CH), 129.1 (CH), 128.8 (CH), 128.6 (CH), 128.5 (CH), 128.4 (CH), 128.3 (CH), 128.2 (CH), 128.0 (CH), 127.99 (CH), 127.94 (CH), 127.85 (CH), 127.81 (CH), 127.6 (CH), 127.4 (CH), 127.3 (CH), 127.2 (CH), 126.3 (CH), 126.0 (CH), 125.9 (CH), 125.3 (CH), 121.9 (C), 121.2 (C), 101.6 (CH), 100.9 (CH), 95.4 (CH), 94.9 (CH), 80.9 (CH), 79.6 (CH), 77.7 (CH), 75.0 (CH₂), 74.2 (CH₂), 74.0 (CH₂), 72.9 (CH), 72.7 (CH₂), 72.6 (CH), 71.8 (CH), 71.6 (CH), 68.6 (CH₂), 68.5 (CH₂), 67.4 (CH), 67.2 (CH₂), 66.9 (CH), 66.8 (CH), 66.2 (CH), 66.1 (CH), 64.2 (CH), 63.8 (CH), 62.3 (CH₂), 62.0 (CH₂), 52.1 (CH), 51.8 (CH), 50.5 (CH₂), 50.2 (CH₂), 47.1 (CH₂), 46.1 (CH₂), 29.2 (CH₂), 28.0 (CH₂), 27.5 (CH₂), 23.5 (CH₂), 23.4 (CH₂), 19.52 (CH₃), 19.50 (CH₃) HRMS m/z (ESI, M+Na⁺) calcd for $C_{117}H_{129}N_7O_{23}Si_2Br_2Na^+$ 2236.6943, found 2236.6885.

Compound 53

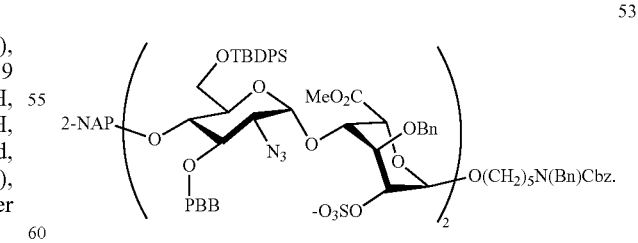

¹H NMR (600 MHz, CD₃OD) δ=7.72-7.70 (m, 5H, Ar—H), 7.65-7.59 (m, 6H, Ar—H), 7.44 (s, 1H, Ar—H), 7.35-7.31 (m, 9H, Ar—H), 7.26-7.21 (m, 16H, Ar—H), 7.14-7.07 (m, 16H, Ar—H), −6.90 (d, J=8.2 Hz, 2H, Ar—H), 5.52 (s, 1H, H-1"), 5.18-5.09 (m, 5H, H-1, H-1', H-1'", ArCH₂), 4.81-4.80 (m, 2H, ArCH₂), 4.77-4.70 (m,

7H, H-5, H-5″, ArCH$_2$), 4.56-4.50 (m, 5H, H-2, H-2″, ArCH$_2$), 4.37-4.32 (m 5H, H-3, H-3″, H-4″, ArCH$_2$), 4.14-4.10 (m, 2H, H-6‴), 3.98-3.85 (m, 7H, H-3′, H-4′, H-4, H-5′, H-5‴, H-6′), 3.66-3.63 (m, 5H, H-3‴, H-4‴, CO$_2$Me), 3.54-3.52 (m, 1H, linker CH$_2$), 3.44-3.37 (m, 1H, linker CH$_2$), 3.25-3.23 (m, 2H, H-2′, H-2‴), 3.19 (s, 3H, CO$_2$Me), 3.10-3.04 (m, 2H, linker CH$_2$), 1.54-1.42 (m, 4H, linker CH$_2$), 1.23-1.17 (m, 2H, linker CH$_2$), 0.96 (s, 9H, TBDPS), 0.91 (s, 9H, TBDPS).

$^{13}$C NMR (150 MHz, CD$_3$OD) δ=170.3 (C), 169.4 (C), 157.0 (C), 156.5 (C), 137.9 (C), 137.79 (C), 137.72 (C), 137.6 (C), 137.3 (C), 136.68 (C), 136.63 (C), 135.9 (CH), 135.8 (CH), 135.79 (CH), 135.73 (CH), 135.4 (CH), 133.5 (C), 133.3 (C), 133.29 (C), 133.22 (C), 133.0 (C), 132.9 (C), 131.0 (CH), 130.7 (CH), 129.6 (CH), 129.56 (CH), 129.53 (CH), 129.3 (CH), 129.2 (CH), 128.4 (CH), 128.3 (CH), 128.2 (CH), 128.1 (CH), 127.8 (CH), 127.7 (CH), 127.6 (CH), 127.5 (CH), 127.4 (CH), 127.37 (CH), 127.33 (CH), 127.1 (CH), 127.0 (CH), 126.9 (CH), 125.7 (CH), 125.6 (CH), 125.5 (CH), 125.3 (CH), 120.9 (C), 120.5 (C), 99.2 (CH), 98.2 (CH), 96.3 (CH), 94.0 (CH), 79.7 (CH), 78.6 (CH), 78.1 (CH), 77.9 (CH), 74.2 (CH$_2$), 73.9 (CH$_2$), 73.4 (CH$_2$), 72.6 (CH), 72.3 (CH), 72.1 (CH), 71.8 (CH$_2$), 71.1 (CH), 70.4 (CH), 70.2 (CH), 70.1 (CH), 68.9 (CH), 68.08 (CH$_2$), 68.00 (CH$_2$), 67.0 (CH$_2$), 66.9 (CH$_2$), 66.7 (CH), 63.8 (CH), 63.7 (CH), 62.48 (CH$_2$), 62.42 (CH$_2$), 51.8 (CH), 51.0 (CH), 50.1 (CH$_2$), 49.9 (CH$_2$), 47.0 (CH$_2$), 46.5 (CH$_2$), 46.1 (CH$_2$), 28.8 (CH$_2$), 26.3 (CH$_3$), 26.2 (CH$_3$), 23.1 (C), 19.0 (C), 18.8 (C) HRMS m/z (ESI, M-2H$^{2-}$) calcd for C$_{117}$H$_{127}$N$_7$O$_{29}$Si$_2$Br$_2$$^{2-}$ 1186.3027, found 1186.3027.

Compound 55

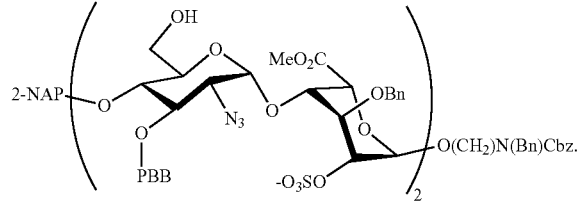

$^1$H NMR (600 MHz, CD$_3$OD) δ=7.73-7.70 (m, 3H, Ar—H), 7.59 (s, 1H, Ar—H), 7.41-7.37 (m, 6H, Ar—H), 7.29-7.26 (m, 10H, Ar—H), 7.22-7.17 (m, 11H, Ar—H), 7.10-7.08 (m, 2H, Ar—H), 6.95 (d, J=8.4 Hz, 2H, Ar—H), 5.31 (s, 1H, H-1″), 5.10-5.03 (m, 5H, H-1, H-1′, H-1‴, ArCH$_2$), 4.76-4.71 (m, 7H, H-5, H-5″, ArCH$_2$), 4.59-4.50 (m, 7H, H-2, H-2″, ArCH$_2$), 4.38-4.36 (m, 2H, ArCH$_2$), 4.24-4.22 (m, 2H, H-3, H-3‴), 4.07 (s, 1H, H-4″), 3.92-3.87 (m, 4H, H-3‴, H-4, H-6‴), 3.75-3.73 (m, 1H, H-6′a), 3.70-3.67 (m, 6H, H-3′, H-5″, H-6′b, CO$_2$Me), 3.60-3.57 (m 4H, H-4′, H-4‴, H-5′, linker CH$_2$), 3.42-3.37 (m, 4H, linker CH$_2$, CO$_2$Me), 3.22-3.19 (m, 2H, H-2′, H-2‴), 3.14-3.09 (m, 2H, linker CH$_2$), 1.53-1.44 (m, 4H, linker CH$_2$), 1.26-1.20 (m, 2H, linker CH$_2$).

$^{13}$C NMR (150 MHz, CD$_3$OD) δ=170.1 (C), 170.0 (C), 157.1 (C), 156.5 (C), 138.0 (C), 137.77 (C), 137.75 (C), 137.4 (C), 135.9 (C), 133.3 (C), 133.0 (C), 130.9 (CH), 130.7 (CH), 129.4 (CH), 129.1 (CH), 128.4 (CH), 128.3 (CH), 128.2 (CH), 128.1 (CH), 127.9 (CH), 127.8 (CH), 127.6 (CH), 127.5 (CH), 127.36 (CH), 127.31 (CH), 126.9 (CH), 125.8 (CH), 125.7 (CH), 125.5 (CH), 125.4 (CH), 120.8 (C), 120.5 (C), 99.4 (CH), 98.3 (CH), 97.1 (CH), 95.7 (CH), 79.7 (CH), 78.2 (CH), 77.6 (CH), 74.2 (CH$_2$), 73.8 (CH$_2$), 73.2 (CH$_2$), 73.0 (CH), 72.5 (CH), 72.4 (CH), 72.0 (CH$_2$), 71.6 (CH$_2$), 70.9 (CH), 70.5 (CH), 67.9 (CH$_2$), 67.3 (CH$_2$), 67.2 (CH), 67.1 (CH$_2$), 66.9 (CH$_2$), 63.8 (CH), 63.5 (CH), 60.0 (CH$_2$), 59.8 (CH$_2$), 51.6 (CH$_3$), 51.2 (CH$_3$), 50.1 (CH$_2$), 49.9 (CH$_2$), 48.4 (CH), 48.2 (CH), 47.1 (CH), 47.0 (CH), 46.1 (CH$_2$), 28.8 (CH$_2$), 27.5 (CH$_2$), 27.1 (CH$_2$), 23.2 (CH$_2$), 23.1 (CH$_2$); HRMS m/z (ESI, M-2H$^{2-}$) calcd for C$_{85}$H$_{91}$N$_7$O$_{29}$S$_2$Br$_2$$^{2-}$ 948.1851, found 948.1830.

Compound 57

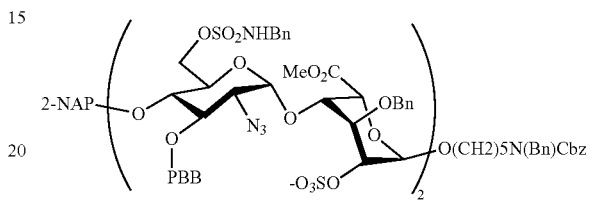

$^1$H NMR (600 MHz, CD$_3$OD) δ=7.75-7.73 (m, 1H, Ar—H), 7.70-7.68 (m, 2H, Ar—H), 7.58 (s, 1H, Ar—H), 7.44-7.42 (m, 2H, Ar—H), 7.39-7.36 (m, 4H, Ar—H), 7.32-7.30 (m, 8H, Ar—H), 7.27-7.26 (m, 2H, Ar—H), 7.25-7.23 (m, 5H, Ar—H), 7.20-7.16 (m, 14H, Ar—H), 7.11-7.07 (m, 4H, Ar—H), 6.99 (d, J=8.2 Hz, 2H, Ar—H), 5.26 (s, 1H, H-1″), 5.13 (d, J=3.4 Hz, 1H, H-1‴), 5.11-5.06 (m, 3H, H-1, ArCH$_2$), 4.96 (d, J=3.1 Hz, 1H, H-1′), 4.81-4.80 (m, 1H, ArCH$_2$), 4.74-4.72 (m, 4H, H-5″, ArCH$_2$), 4.69-4.66 (m, 3H, H-5, ArCH$_2$), 4.62-4.57 (m, 4H, H-2″, ArCH$_2$), 4.48 (d, J=11.3 Hz, 1H, ArCH$_2$), 4.45-4.40 (m, 4H, H-6‴b, ArCH$_2$), 4.29-4.25 (m, 5H, H-2, H-3″, H-6′b, H-6‴a, ArCH$_2$), 4.19-4.13 (m, 5H, H-3, H-4″, H-6′a, ArCH$_2$), 3.95 (s, 1H, H-4), 3.91-3.84 (m, 4H, H-3′, H-4‴, H-5′, H-5‴), 3.72 (s, 3H, CO$_2$Me), 3.67-3.61 (m, 2H, H-3‴, linker CH$_2$), 3.46-3.39 (m, 5H, H-4′, CO$_2$Me, linker CH$_2$), 3.27-3.25 (m, 1H, H-2‴), 3.21 (dd, J=3.1, 10.2 Hz, 1H, H-2′), 3.15-3.11 (m, 2H, linker CH$_2$), 1.59-1.47 (m, 4H, linker CH$_2$), 1.28-1.22 (m, 2H, linker CH$_2$).

$^{13}$C NMR (150 MHz, CD$_3$OD) δ=170.3 (C), 169.8 (C), 157.1 (C), 156.5 (C), 147.9 (C), 138.0 (C), 137.9 (C), 137.64 (C), 137.61 (C), 137.2 (C), 137.1 (C), 136.6 (C), 135.5 (C), 133.3 (C), 133.0 (C), 130.9 (CH), 130.8 (CH), 129.4 (CH), 129.1 (CH), 128.39 (CH), 128.31 (CH), 128.2 (CH), 128.1 (CH), 128.0 (CH), 127.9 (CH), 127.84 (CH), 127.82 (CH), 127.68 (CH), 127.62 (CH), 127.60 (CH), 127.3 (CH), 127.2 (CH), 127.0 (CH), 126.9 (CH), 125.9 (CH), 125.7 (CH), 125.5 (CH), 125.4 (CH), 120.8 (C), 120.6 (C), 99.4 (CH), 98.8 (CH), 97.2 (CH), 95.2 (CH), 79.7 (CH), 78.1 (CH), 77.4 (CH), 74.2 (CH$_2$), 73.9 (CH$_2$), 73.4 (CH$_2$), 73.3 (CH), 72.5 (CH), 72.3 (CH), 72.1 (CH$_2$), 71.7 (CH$_2$), 71.4 (CH), 71.0 (CH), 70.3 (CH), 70.23 (CH), 70.20 (CH), 69.9 (CH), 67.9 (CH), 67.8 (CH$_2$), 67.7 (CH), 67.19 (CH), 67.11 (CH), 67.0 (CH), 66.9 (CH$_2$), 63.6 (CH), 63.4 (CH), 51.7 (CH), 51.4 (CH), 50.1 (CH$_2$), 49.9 (CH$_2$), 46.78 (CH$_2$), 46.70 (CH$_2$), 46.5 (CH$_2$), 46.2 (CH$_2$), 46.1 (CH$_2$), 28.7 (CH$_2$), 27.5 (CH$_2$), 27.1 (CH$_2$), 23.0 (CH$_3$) HRMS m/z (ESI, M-2H$^{2-}$) calcd for C$_{99}$H$_{105}$N$_9$O$_{33}$Br$_2$ 1116.7032, found 1116.7029.

Compound 59

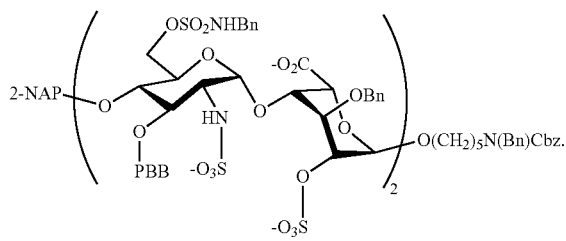

¹H NMR (600 MHz, Methanol-d4) δ=7.75-7.70 (m, 3H, Ar—H), 7.58 (s, 1H, Ar—H), 7.37-7.33 (m, 9H, Ar—H), 7.27-7.25 (m, 6H, Ar—H), 7.21-7.19 (m, 6H, Ar—H), 7.16-7.10 (m, 20H, Ar—H), 5.93 (s, 1H, H-1″), 5.31-5.24 (m, 4H, H-1, H-1′, H-1‴, ArCH$_2$), 5.14-5.08 (m, 3H, ArCH$_2$), 4.84-4.82 (m, 2H, H-5″, ArCH$_2$), 4.74-4.72 (m, 1H, H-5), 4.66-4.60 (m, 5H, H-2, H-2″, ArCH$_2$), 4.48-4.39 (m, 9H, H-3, H-3″, H-6‴, ArCH$_2$), 4.24-4.13 (m, 12H, H-4, H-4″, H-4‴, H-5′, H-5‴, H-6′, ArCH$_2$), 3.87-3.84 (m, 2H, H-3′, H-3‴), 3.58-3.53 (m, 4H, H-2′, H-2‴, H-4′, linker), 3.46-3.39 (m, 1H, linker CH$_2$), 3.12-3.06 (m, 2H, linker CH$_2$), 1.55-1.45 (m, 4H, linker CH$_2$), 1.27-1.18 (m, 2H, linker CH$_2$).

¹³C NMR (150 MHz, Methanol-d4) δ=175.9 (C), 174.3 (C), 157.0 (C), 156.5 (C), 138.9 (C), 138.8 (C), 138.19 (C), 138.16 (C), 137.9 (C), 137.7 (C), 137.5 (C), 137.3 (C), 136.7 (C), 135.7 (C), 133.3 (C), 133.0 (C), 130.8 (C), 130.5 (CH), 129.9 (CH), 129.7 (CH), 128.19 (CH), 128.14 (CH), 127.9 (CH), 127.7 (CH), 127.6 (CH), 127.59 (CH), 127.57 (CH), 127.2 (CH), 127.17 (CH), 127.10 (CH), 126.9 (CH), 126.8 (CH), 126.5 (CH), 126.0 (CH), 125.7 (CH), 125.5 (CH), 120.5 (C), 120.2 (C), 98.7 (CH), 98.5 (CH), 96.1 (CH), 93.3 (CH), 80.2 (CH), 77.4 (CH), 75.4 (CH), 74.9 (CH), 74.5 (CH), 73.9 (CH$_2$), 73.7 (CH), 73.2 (CH$_2$), 73.0 (CH), 71.3 (CH$_2$), 71.2 (CH$_2$), 70.7 (CH), 70.3 (CH), 68.0 (CH$_2$), 67.9 (CH$_2$), 67.7 (CH), 67.3 (CH$_2$), 67.0 (CH$_2$), 66.9 (CH), 66.6 (CH), 59.0 (CH), 58.7 (CH), 50.0 (CH$_2$), 49.8 (CH$_2$), 46.8 (CH$_2$), 46.5 (CH$_2$), 28.8 (CH$_2$), 27.6 (CH$_2$), 27.0 (CH$_2$), 23.1 (CH$_2$); HRMS m/z (ESI, M-4H$^+$ 1Na$^{3-}$) calcd for C$_{97}$H$_{103}$N$_5$O$_{39}$Br$_2$Na$^{3-}$ 778.0940, found 778.0941.

Compound 59

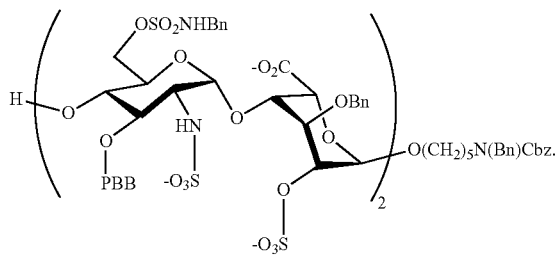

¹H NMR (600 MHz, D$_2$O) δ=5.32 (d, J=3.4 Hz, 1H, H-1‴), 5.28 (d, J=3.3 Hz, 1H, H-1′), 5.24 (s, 1H, H-1″), 5.04 (s, 1H, H-1), 4.81 (s, 1H, H-5″), 4.47-4.43 (m, 4H, H-5, H-6′a, H-6‴), 4.35-4.32 (m, 2H, H-2″, H-6′b), 4.19-4.16 (m, 3H, H-2, H-3, H-3″), 4.05-4.00 (m, 4H, H-4, H-4″, H-5′, H-5‴), 3.69-3.64 (m, 5H, H-3′, H-3‴, H-4′, H-4‴, linker CH$_2$), 3.47 (t, J=9.5 Hz, 1H, linker CH$_2$), 3.20-3.18 (m, 2H, linker CH$_2$), 2.94-2.92 (m, 2H, H-2′, H-2‴), 1.68-1.54 (m, 4H, linker CH$_2$), 1.48-1.26 (m, 2H, linker CH$_2$).

¹³C NMR (150 MHz, D$_2$O) δ=99.2 (CH), 98.9 (CH), 97.6 (CH), 96.9 (CH), 77.0 (CH), 76.2 (CH), 74.6 (CH), 70.8 (CH), 69.4 (CH), 68.9 (CH), 68.7 (CH), 68.6 (CH$_2$), 68.3 (CH$_2$), 68.0 (CH), 67.7 (CH), 57.9 (CH), 39.4 (CH$_2$), 27.8 (CH$_2$), 26.1 (CH$_2$), 22.1 (CH$_2$); HRMS m/z (ESI, M-3H$^{3-}$) calcd for C$_{29}$H$_{50}$N$_5$O$_{37}$S$_6^{3-}$ 417.3503, found 417.3505.

3.2 Screening of Compounds of Example 3.1 for Inhibitory Activity Toward Sulf-1

Figure 3:
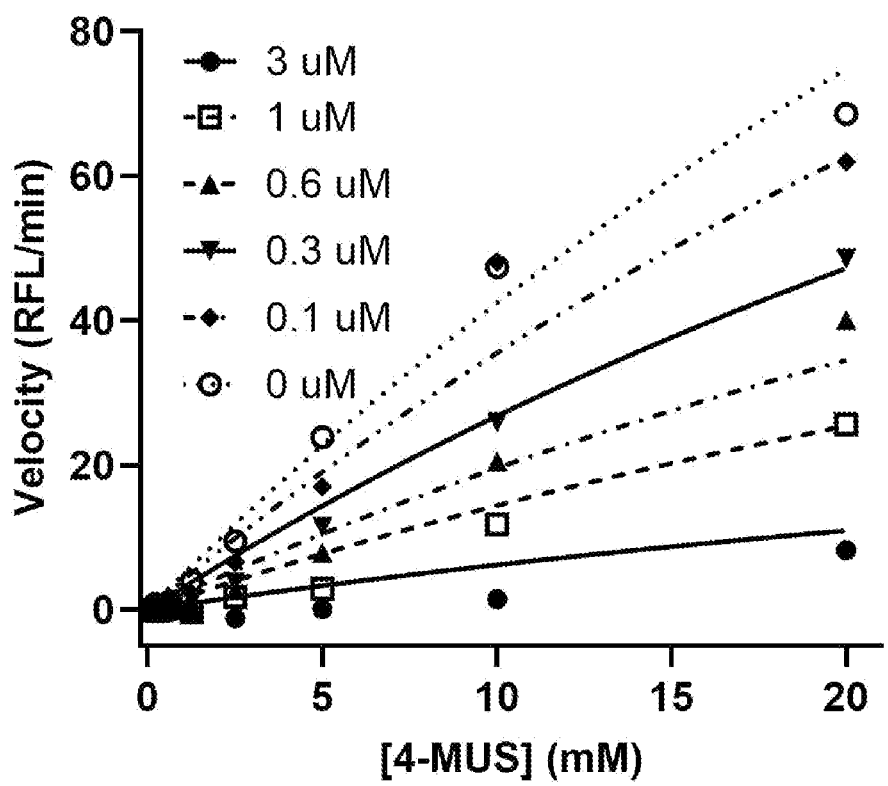
FIG. 3 depicts the kinetic measurements for determining the Ki value of compound 46 using the 4-MUS fluorogenic assay.

The inhibitory activity of compounds 45-47 toward Sulf-1 were further examined with the fluorescent assay by monitoring the hydrolysis of 4-MUS to 4-MU. Only 20% of Sulf-1 activity was inhibited with the disaccharide analog 45 at 0.7 mM. Conversely, the tri- and tetrasaccharide analogues 46 and 47 exhibited more potent inhibition with IC$_{50}$ values of 0.53 μM and 29.6 μM, respectively. In addition, using the 4-MUS activity assay, kinetic measurements were performed to determine the inhibitory activity of 46, confirming the selectivity and potency of this inhibitor. The kinetic studies of the inhibitory activity showed that the Ki value (0.36 μM, FIG. 3) is in good agreement with the IC$_{50}$ value (0.53 μM).

Figure 4:
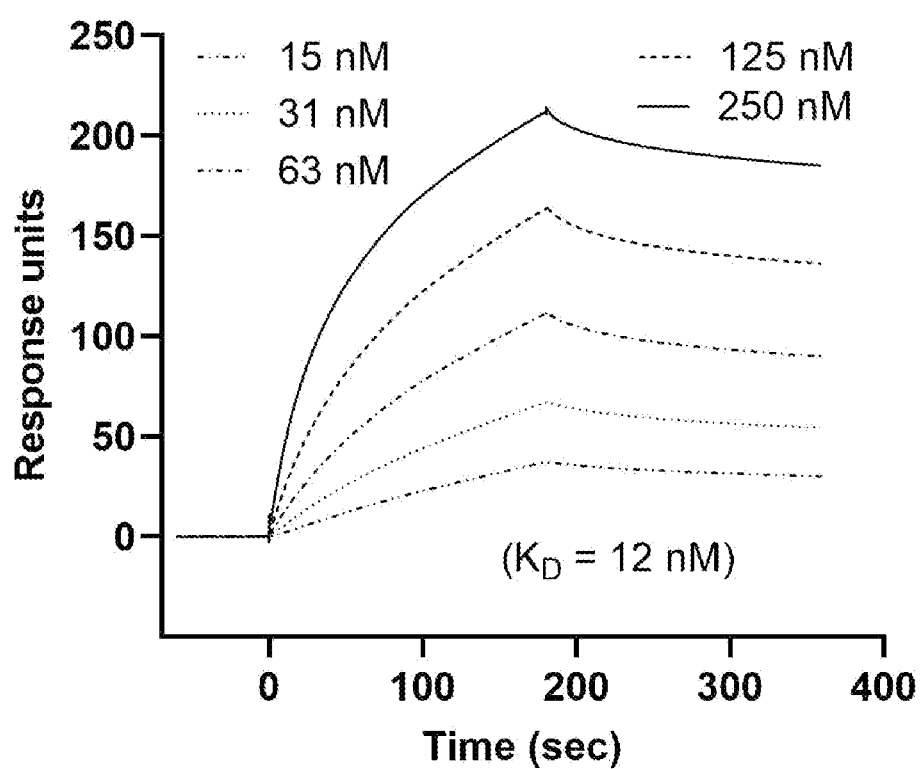
FIG. 4 depicts the binding kinetics of compound 46 in accordance with one embodiment of the present disclosure.

With highest inhibitory activity, the binding affinity of the inhibitor 46 with human Sulf-1 was further measured by surface plasmon resonance (SPR). The hydrophilic domain-deleted mutant of Sulf-1, namely human Sulf-1$_{d417-726}$, lacking two furin-type proteinase cleavage sites responsible for forming the disulfide-bonded heterodimers of 75- and 50-kDa subunits with retained enzyme activity was constructed according to the literature report. Compound 46 was immobilized on the CM5 sensor chip, and aliquots of human Sulf-1$_{d417-726}$ at gradient concentrations were applied onto the chip. From the concentration-dependent titration curves (FIG. 4) resulting from stable complexes upon fast association and very slow dissociation, the dissociation constant (K$_D$) was determined as 12 nM, indicating that 46 could be applied as a probe to identify new Sulfs and inhibitors through its attachment to the magnetic nanoparticles.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of the present disclosure.

What is claimed is:

1. A compound of formula (I), or a solvate thereof,

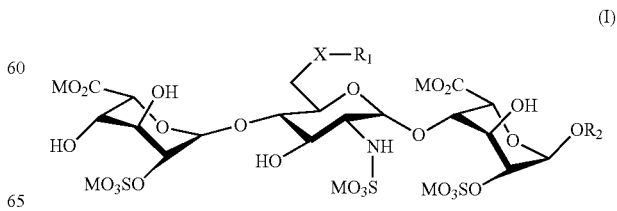

wherein:

X is methylene, O, or —NH;

R$_1$ is —SO$_3$M, or —SO$_2$NH$_2$;

R$_2$ is C$_{1-6}$ alkyl or C$_{1-6}$ alkylamine;

M is H or a monovalent cation selected from the group consisting of lithium, sodium, potassium, and ammonium; and in the case when X is O, R$_1$ is —SO$_3$Na, then R$_2$ is C$_{2-6}$ alkyl or C$_{1-6}$ alkylamine.

2. The compound of claim 1, wherein the compound is a human endo-O-sulfatase 1 (Sulf-1) inhibitor selected from the group consisting of

46

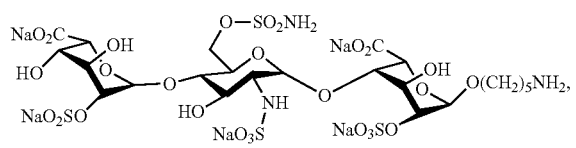

46-1

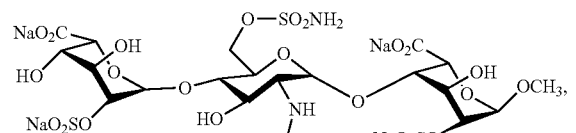

60

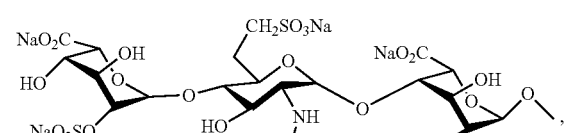

61

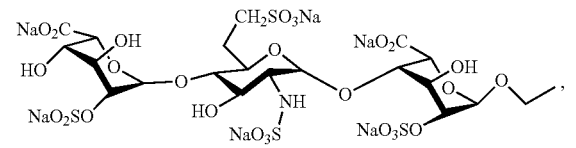

62

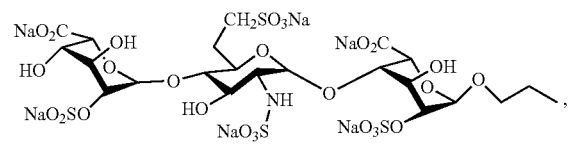

63

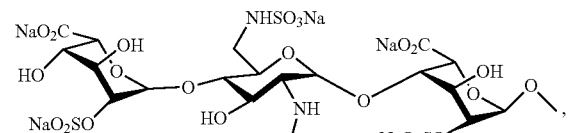

64

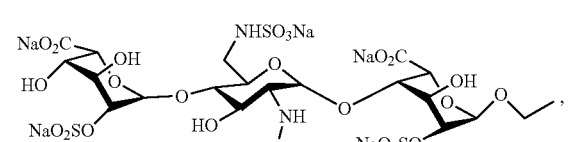

65

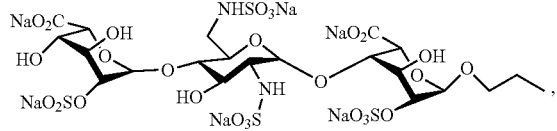

66

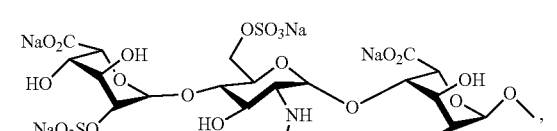

67

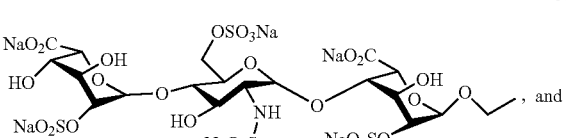

, and

68

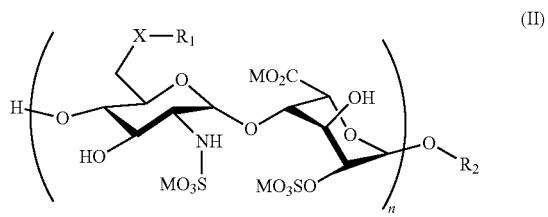

.

3. The compound of claim 1, wherein the compound is a substrate of Sulf-1, in which X is O, R$_1$ is —SO$_3$M, R$_2$ is —(CH$_2$)$_5$NH$_2$, and M is sodium.

4. A compound of formula (II), or a solvate thereof, (II)

wherein:

n is 2 or 3;

X is methylene, O, or —NH;

R$_1$ is —SO$_3$M, or —SO$_2$NH$_2$;

R$_2$ is C$_{1-6}$ alkyl or C$_{1-6}$ alkylamine; and

M is H or a monovalent cation selected from the group consisting of lithium, sodium, potassium, and ammonium.

5. The compound of claim 4, wherein the compound is a human endo-O-sulfatase 1 (Sulf-1) inhibitor, in which n is 2, X is O, R$_1$ is —SO$_2$NH$_2$, R$_2$ is —(CH$_2$)$_5$NH$_2$, and M is sodium.

6. The compound of claim 4, wherein the compound is a substrate of Sulf-1, in which n is 2, X is O, R$^1$ is —SO$_3$M, R$_2$ is —(CH$_2$)$_5$NH$_2$, and M is sodium.

7. The compound of claim 4, wherein the compound is a substrate of Sulf-1, in which n is 3, X is O, R$^1$ is —SO$_3$M, R$_2$ is —(CH$_2$)$_5$NH$_2$, and M is sodium.

8. A method for identifying and treating a subject having osteoarthritis comprising, (a) mixing a urine sample of the subject with 4-methylumbelliferyl sulfate (4-MUS) and a compound of any one of claim 2 or 5;

(b) determining a fluorescence intensity of the mixture of the step (a); and
(c) treating the subject with an analgesic, a non-steroidal anti-inflammatory drug (NSAID), or a corticosteroid when the determined fluorescence intensity of the step (b) is smaller than that of a control sample, which is a mixture of the urine sample and 4-MUS.

9. The method of claim 8, wherein the compound of any one of claim 2 or 5 is labeled with a tag molecule and coated on a surface of a membrane, and the 4-MUS is coated at one end of the membrane in the form of a line.

10. The method of claim 8, wherein the analgesic is acetaminophen or codeine.

11. The method of claim 8, wherein the NSAID is selected from the group consisting of aspirin, ibuprofen, naproxen, diclofenac, celecoxib, piroxicam, indomethacin, meloxicam, ketoprofen, sulindac, diflunisal, nabumetone, oxaprozin, tolmetin, salsalate, etodolac, fenoprofen, flurbiprofen, ketorolac, meclofenamate, and mefenamic acid.

12. The method of claim 8, wherein the corticosteroid is cortisol.

\* \* \* \* \*